US009598326B2

(12) United States Patent
Gaab et al.

(10) Patent No.: US 9,598,326 B2
(45) Date of Patent: Mar. 21, 2017

(54) PROCESS FOR THE CONVERSION OF OXYGENATES TO OLEFINS

(71) Applicant: BASF SE, Ludwigshafen (DE)

(72) Inventors: Manuela Gaab, Heidelberg (DE); Ulrich Müller, Neustadt (DE); Milan Kostur, Mutterstadt (DE); Kirsten Spannhoff, Ludwigshafen (DE); Kerem Bay, Ludwigshafen (DE); Andrei-Nicolae Parvulescu, Heidelberg (DE)

(73) Assignee: BASF SE, Ludwigshafen (DE)

( * ) Notice: Subject to any disclaimer, the term of this patent is extended or adjusted under 35 U.S.C. 154(b) by 523 days.

(21) Appl. No.: 14/076,723

(22) Filed: Nov. 11, 2013

(65) Prior Publication Data

US 2014/0142361 A1 May 22, 2014

Related U.S. Application Data

(60) Provisional application No. 61/725,518, filed on Nov. 13, 2012.

(51) Int. Cl.
C07C 1/22 (2006.01)
C07C 1/20 (2006.01)

(52) U.S. Cl.
CPC ............ C07C 1/20 (2013.01); *C07C 2529/40* (2013.01)

(58) Field of Classification Search
CPC ................ C07C 1/00; C07C 1/20; C07C 1/24
USPC ... 585/638, 639, 640; 502/60, 64, 67, 71, 77
See application file for complete search history.

(56) References Cited

U.S. PATENT DOCUMENTS

| 4,404,175 | A | 9/1983 | Marosi et al. |
| 4,480,145 | A | 10/1984 | Brennan et al. |
| 4,851,605 | A | 7/1989 | Bortinger et al. |
| 5,063,187 | A | 11/1991 | Burgfels et al. |
| 5,409,682 | A | 4/1995 | Mueller et al. |
| 7,608,746 | B2 * | 10/2009 | Setoyama ............... C07C 2/864 585/639 |
| 7,902,102 | B2 * | 3/2011 | Bosch ...................... B01J 29/40 423/700 |
| 2004/0138053 | A1 | 7/2004 | Burgfels et al. |
| 2007/0135637 | A1 | 6/2007 | Bosch et al. |
| 2011/0144335 | A1 | 6/2011 | Bosch et al. |

FOREIGN PATENT DOCUMENTS

| DE | 41 31 448 A1 | 3/1993 |
| DE | 103 56 184 A1 | 7/2005 |
| EP | 0 041 621 A1 | 12/1981 |
| EP | 0 123 449 A1 | 10/1984 |
| EP | 0 178 687 A2 | 4/1986 |
| EP | 0 369 364 A2 | 5/1990 |
| EP | 0 448 000 A1 | 9/1991 |
| EP | 1 424 128 A1 | 6/2004 |
| WO | WO-2005/053842 A1 | 6/2005 |
| WO | WO-2014/076032 A1 | 5/2014 |

OTHER PUBLICATIONS

Lee, Y.-J., et al., "Textural Properties and Catalytic Applications of ZSM-5 Monolith Foam for Methanol Conversion", Catalysis Letters, 2009, vol. 129, No. 3-4, pp. 408-415.
Choi, M., et al., "Stable Single-Unit-Cell Nanosheets of Zeolite MFI as Active and Long-Lived Catalysts", Nature, 2009, vol. 461, No. 7261, pp. 246-249.
Hammon, U., et al., "Formation of Ethene and Propene from Methanol on Zeolite ZSM-5 II. Preparation of Finished Catalysts and Operation of a Fixed-Bed Pilot Plant", Applied Catalysis, 1988, vol. 37, pp. 155-174.
Rownaghi, A. A., et al., "Yield of Gasoline-Range Hydrocarbons as a Function of Uniform ZSM-5 Crystal Size", Catalysis Communications, 2011, vol. 14, No. 1, pp. 37-41.
Liu, N., et al., "A New Synthesis Route for MWW Analogues Using Octyltrimethylammonium Cations as Structure-Directing Agents under Alkali-Free Conditions", Chemistry Letters, 2007, vol. 36, No. 7, pp. 916-917.
De Baerdemaeker, T., et al., "Alkali-Free Synthesis of AI-MTW Using 4-Cyclohexyl-1,1-Dimethylpiperazinium Hydroxide as Structure Directing Agent", Microporous and Mesoporous Materials, 2011, vol. 143, pp. 477-481.
Takeguchi, T., et al., "Synthesis and Characterization of Alkali-Free, Ga-Substituted MCM-41 and its Performance for n-Hexane Conversion", Journal of Catalysis, 1998, vol. 175, pp. 1-6.
Ahedi, R. K., et al., "Synthesis of FER Titanosilicates from a Non-Aqueous Alkali-Free Seeded System", J. Mater. Chem., 1998, vol. 8, No. 8, pp. 1685-1686.

(Continued)

*Primary Examiner* — Sharon Pregler
(74) *Attorney, Agent, or Firm* — Drinker Biddle & Reath LLP

(57) ABSTRACT

The present invention relates to a process for the conversion of oxygenates to olefins comprising
(i) providing a gas stream comprising one or more oxygenates; and
(ii) contacting the gas stream with a catalyst;
wherein the catalyst comprises a zeolitic material having an MFI, MEL, and/or MWW-type framework structure comprising $YO_2$ and $X_2O_3$, wherein Y is a tetravalent element, and X is a trivalent element,
said zeolitic material being obtainable and/or obtained according to a method comprising
(1) preparing a mixture comprising one or more sources for $YO_2$, one or more sources for $X_2O_3$, and one or more solvents; and
(2) crystallizing the mixture obtained in step (1) to obtain a zeolitic material having an MFI, MEL and/or MWW-type framework structure;
wherein the mixture crystallized in step (2) contains 3 wt.-% or less of the one or more elements M based on 100 wt.-% of $YO_2$, wherein M stands for sodium.

35 Claims, 18 Drawing Sheets

(56) References Cited

OTHER PUBLICATIONS

Dodwell, G. W., et al., "Crystallization of EU-1 and EU-2 in Alkali and Alkali-Free Systems", Zeolites, 1985, vol. 5, pp. 153-157.
Shibata, M., et al., "Synthesis of Alkali-Free MFI Borosilicates from Methylamine-$SiCl_4$ Media", Applied Catalysis A: General, 1997, vol. 162, pp. 93-102.
Reding, G., et al., "Comparing Synthesis Routes to Nano-Crystalline Zeolite ZSM-5", Microporous and Mesoporous Materials, 2003, vol. 57, pp. 83-92.
Van Grieken, R., et al., "Anomalous Crystallization Mechanism in the Synthesis of Nanocrystalline ZSM-5", Microporous and Mesoporous Materials, 2000, vol. 39, pp. 135-147.
Rivas-Cardona, A., et al., "A Systematic Investigation of Silicalite-1 Precursor Mixtures with Varying Degrees of Dilution", Microporous and Mesoporous Materials, 2012, vol. 155, pp. 56-64.

* cited by examiner

PROCESS FOR THE CONVERSION OF OXYGENATES TO OLEFINS

CROSS-REFERENCE TO RELATED APPLICATIONS

This application claims benefit (under 35 USC 119(e)) of U.S. Provisional Application No. 61/725,518, filed Nov. 13, 2012, which is incorporated by reference.

The present invention relates to a process for the conversion of oxygenates to olefins employing a catalyst comprising a zeolitic material having an MFI, MEL, and/or MWW-type framework structure, wherein said zeolitic material is obtainable and/or obtained according to a specific method employing 3 wt.-% or less of sodium based on 100 wt.-% of $YO_2$, Y standing for a tetravalent element.

INTRODUCTION

In view of the decreasing amount of oil reserves which constitute the raw material for the production of short-chain hydrocarbons and derivatives thereof, alternative processes for the production of such base chemicals are of a growing importance. In such alternative processes for the production of short-chain hydrocarbons and derivatives thereof, often highly specific catalysts are used therein for converting other raw materials and/or chemicals to hydrocarbons and their derivatives such as in particular short-chain olefins. A particular challenge involved in such processes not only relies in the optimal choice of reaction parameters but, more importantly, in the use of particular catalysts allowing for the highly efficient and selective conversion to a desired hydrocarbon or derivative thereof such as in particular olefinic fractions. In this respect, processes in which methanol is employed as the starting material, are of particular importance, wherein their catalytic conversion usually leads to a mixture of hydrocarbons and derivatives thereof, in particular olefins, paraffins, and aromatics.

Thus, the particular challenge in such catalytic conversions resides in the optimization and the fine tuning of the catalysts employed as well as the process architecture and parameters such that as high a selectivity towards as few products as possible may be achieved. For this reason, such processes are often named after the products for which a particularly high selectivity may be achieved in the process. Accordingly, processes which have been developed in the past decades towards the conversion of oxygenates to olefins and in particular of methanol to olefins which have gained increasing importance in view of dwindling oil reserves are accordingly designated as methanol-to-olefin-processes (MTO-processes for methanol to olefins).

Among the catalytic materials which have been found for use in such conversions, zeolitic materials have proven of high efficiency, wherein in particular zeolitic materials of the pentasil-type and more specifically those having an MFI- and MEL-type framework structures including such zeolites displaying an MFI-MEL-intergrowth type framework structure are employed. As regards the specific application of zeolitic materials and in particular zeolitic materials of the pentasil-type in catalysis and more particularly in processes for the conversion of oxygenates to olefins such as the MTO-processes discussed in the foregoing, EP 0 369 364 A2 relates to a crystalline aluminosilicate of the pentasil-type and its use in the conversion of methanol to olefins and gasoline. EP 0 448 000 B1 concerns a process for the production of lower olefins from methanol using crystalline aluminosilicates of the pentasil-type having an alkaline content of less than 380 ppm. EP 1 424 128 A, on the other hand, describes a catalyst based on a crystalline aluminosilicate of the pentasil-type characterized in that it contains primary crystals having an average diameter of at least 0.01 µm and less than 0.1 µm of which at least 20% are agglomerated to particles having an average particle size of 5 to 500 µm.

On the other hand, as regards the synthesis of zeolitic materials in general, efforts have been invested into their optimization for economical and increasingly also for environmental reasons. In this respect, it has been found that crystallizing an aluminosilicate in the absence of an alkali source allows to omit the ion-exchange procedures normally required after crystallization to obtain the so called H-form thereof, wherein the alkali metals present in the resulting material as non-framework element are exchanged against protons. The ion exchanges necessitate additional steps in the manufacturing process considerably reducing the space-time-yield of the zeolite, generating high volumes of waste water, consuming energy and thus increasing overall production costs. Alkali-free synthetic methodologies are thus highly beneficial as it makes the synthesis process simpler with fewer steps, thus more economical and industrially viable. Such a manufacturing process also generates less waste during catalyst production.

Thus, Liu et al. in Chemistry Letters 2007, vol. 36, pp. 916 and 917, for example, concerns a synthetic procedure for the preparation of MWW-type metallosilicates under alkali-free conditions. The De Baerdemaeker et al. in Microporous and Mesoporous Materials 2011, vol. 143, pp. 477-481 concerns the synthesis of MTW-type zeolites which is performed in an alkali-free and fluoride-free synthetic procedure. In Takeguchi et al. in Journal of Catalysis 1998, vol. 175, pp. 1-6 the synthesis of alkali-free Ga-substituted MCM-41 catalysts is described. Ahedi et al. in Journal of Materials Chemistry 1998, vol. 8, pp. 1685-1686 concerns the synthesis of FER titanosilicates from a non-aqueous alkali-free seeded system. Dodwell et al. in Zeolites 1985, vol. 5, pp. 153-157 concerns the crystallization of EU-1 and EU-2 in alkali and alkali-free systems. Shibata et al. in Applied Catalysis A: General 1997, vol. 162, pp. 93-102, on the other hand, describes routes for the synthesis of alkali-free MFI borosilicates.

Furthermore it is now known that the formation, in particular the diameter, of the zeolite crystals obtained via alkali-free processes can be tuned by adjusting the temperature, stirring rate, concentration of the synthesis mixture and the duration of the crystallization. This may be of importance to adjust the diffusion properties of the zeolite for specific catalytic applications and to allow for optimal shaping and properties of the resulting shaped bodies. In particular, appropriate shaped bodies often need to be prepared prior to the introduction of the catalyst into a reactor to carry out the catalytic transformation.

In this respect, DE 103 56 184 A1 relates to a zeolitic material of the pentasil type having a molar ratio of Si to Al of from 250 to 1500, wherein furthermore at least 90% of the primary particles of the zeolitic material are spherical, wherein 95% by weight thereof have a diameter of less than or equal to 1 µm. Furthermore, said document discloses a specific treatment of ZSM-5 powder with demineralized water under autogeneous pressure, wherein it is taught that both the activity and the selectivity would be improved by the water treatment of the ZSM-5 powder under hydrothermal conditions when employed in a process for the preparation of tetraethylenediamine from piperazine and ethylenediamine. DE 41 31 448 A1 on the other hand concerns essentially alkali-free borous silicate crystals having a zeolite structure and a size from 2 to 150 μm.

Reding et al. in Microporous and Mesoporous Materials 2003, vol. 57, pp. 83-92 investigates on synthetic procedures for obtaining nano-crystalline zeolite ZSM-5. Likewise, Van Grieken in Microporous and Mesoporous Materials 2000, vol. 39, pp. 135-147 investigates the crystallization mechanism in the synthesis of nanocrystalline ZSM-5. Rivas-Cardona in Microporous and Mesoporous Materials 2012, vol. 155, pp. 56-64, on the other hand, investigates silicalite-1 precursor mixtures having varying degrees of dilution.

Despite the considerable efforts related by the prior art relative to the synthesis of novel zeolitic materials by using new and improved synthetic procedures on the one hand, and their various applications such as in particular in the field of catalysis on the other hand, there remains an ongoing need to provide new processes for the conversion of oxygenates to olefins employing novel zeolitic materials with which the process efficiency may be improved.

DETAILED DESCRIPTION

It is therefore the object of the present invention to provide an improved process for the conversion of oxygenates to olefins. Thus, it has quite surprisingly been found that zeolitic materials having an MFI, MEL, and/or MWW-type framework structure as may be obtained from an alkali-free synthetic procedure display unexpected technical effects when used in a process for the conversion of oxygenates to olefins. More specifically, it has quite surprisingly been found that such zeolitic materials as described in the present invention lead to a considerable improvement in the conversion of oxygenates to olefins, in particular relative to the specific selectivities which may be achieved therein as well as with respect to the catalyst lifetime during which the catalyst displays a high and sustained level of activity.

Therefore, the present invention relates to a process for the conversion of oxygenates to olefins comprising
  (i) providing a gas stream comprising one or more oxygenates; and
  (ii) contacting the gas stream with a catalyst;
wherein the catalyst comprises a zeolitic material having an MFI, MEL, and/or MWW-type framework structure comprising $YO_2$ and $X_2O_3$, wherein Y is a tetravalent element, and X is a trivalent element,
said zeolitic material being obtainable and/or obtained according to a method comprising
  (1) preparing a mixture comprising one or more sources for $YO_2$, one or more sources for $X_2O_3$, and one or more solvents; and
  (2) crystallizing the mixture obtained in step (1) to obtain a zeolitic material having an MFI, MEL and/or MWW-type framework structure;
wherein the mixture crystallized in step (2) contains 3 wt.-% or less of the one or more elements M based on 100 wt.-% of $YO_2$, wherein M stands for sodium.

Thus, it has quite unexpectedly been found that by employing a zeolitic material in the process for the conversion of oxygenates to olefins according to the present invention, wherein the zeolitic material comprised in the catalyst is obtainable and/or obtained from a reaction mixture containing 3 wt.-% or less of sodium based on 100 wt.-% of $YO_2$ contained in the mixture, a process for the conversion of oxygenates to olefins may be provided which displays considerably improved selectivities relative to $C_3$ and $C_4$ olefinic products. Furthermore, it has surprisingly been found that the specific use of such zeolitic materials in the inventive process allows for sustained activity of the catalyst at a high conversion level thus allowing for increased yields in olefinic products which may be obtained for a given charge of the catalyst before its regeneration and/or replacement.

In the inventive process, the mixture prepared according to step (1) in the method from which the zeolitic material is obtainable and/or obtained is subsequently crystallized in step (2), wherein said mixture crystallized in step (2) contains 3 wt.-% or less of one or more elements M based on 100 wt.-% of $YO_2$. In general, M stands for sodium which may be present in the mixture prepared in step (2) of the method as defined in the present application. According to preferred embodiments of the inventive process, the mixture crystallized in step (2) of the method from which the zeolitic material is obtainable and/or obtained contains 3 wt.-% or less of both sodium and potassium based on 100 wt.-% of $YO_2$, M accordingly standing for sodium and potassium. According to particularly preferred embodiments of the inventive process, however, the mixture prepared in step (1) and crystallized in step (2) of the method displays a total amount of alkali metal elements which does not exceed 3 wt.-% based on 100 wt.-% of $YO_2$. Accordingly, embodiment of the inventive process are particularly preferred wherein the mixture provided in step (1) and crystallized in step (2) of the method according to which the zeolitic material comprised in the catalyst is obtainable and/or obtained contains 3 wt.-% or less of alkali metal elements based on 100 wt.-% of $YO_2$, wherein it is further preferred that said mixture contains 3 wt.-% or less of both alkali metal and alkaline earth metal elements based on 100 wt.-% of $YO_2$ contained in the mixture.

Therefore, according to preferred embodiments of the inventive process for the conversion of oxygenates to olefins, the mixture crystallized in step (2) of the method according to which the zeolitic material comprised in the catalyst is obtainable and/or obtained contains 3 wt.-% or less of one or more elements M based on 100 wt.-% $YO_2$, wherein M stands for sodium and potassium, and preferably for the group of alkali metal elements, wherein more preferably M stands for the group of alkali and alkaline earth metal elements.

According to embodiments of the present invention which are further preferred, the mixture provided in step (1) and crystallized in step (2) of the method according to which the zeolitic material comprised in the catalyst is obtainable and/or is obtained contains less than 1 wt.-% of the one or more elements M according to any of the particular or preferred embodiments of the present invention based on 100 wt.-% of $YO_2$, and more preferably 0.5 wt.-% or less of the one or more elements M, more preferably 0.1 wt.-% or less, more preferably 0.05 wt.-% or less, more preferably 0.01 wt.-% or less, more preferably 0.005 wt.-% or less, more preferably 0.001 wt.-% or less, and more preferably 0.0005 wt.-% or less. According to embodiments thereof which are particularly preferred, the mixture provided in step (1) and crystallized in step (2) of the method according to which the zeolitic material is obtainable and/or obtained contains 0.0003 wt.-% or less of the one or more elements M based on 100 wt.-% of $YO_2$, wherein it is yet further preferred that the mixture crystallized in step (2) of the method according to which the zeolitic material is obtainable and/or obtained contains less than 0.0001 wt.-% of the one or more elements M therein and is therefore substantially free of the one or more elements M according to any of the particular or preferred embodiments of the present invention.

Therefore, according to preferred embodiments of the inventive process, the mixture crystallized in step (2) of the method according to which the zeolitic material is obtainable and/or obtained contains 1 wt.-% or less of the one or more elements M based on 100 wt-% of $YO_2$.

Concerning the gas stream according to step (i), no particular restriction applies according to the present invention relative to the one or more oxygenates which may be contained therein, provided that said one or more oxygenates may be converted to at least one olefin upon contacting thereof with the catalyst comprising a zeolitic material according to the present invention and in particular according to any of the particular and preferred embodiments thereof as defined herein. According to the present invention, it is, however, preferred that the one or more oxygenates contained in the gas stream provided in step (i) comprise one or more oxygenates selected from the group consisting of aliphatic alcohols, ethers, carbonyl compounds, and mixtures of two or more thereof. According to the inventive process for the conversion of oxygenates to olefins, it is further preferred that the one or more oxygenates comprised in the gas stream is selected from the group consisting of $C_1$-$C_6$-alcohols, di-$C_1$-$C_3$-alkyl ethers, $C_1$-$C_6$-aldehydes, $C_2$-$C_6$-ketones, and mixtures of two or more thereof, more preferably from the group consisting of $C_1$-$C_4$-alcohols, di-$C_1$-$C_2$-alkyl ethers, $C_1$-$C_4$-aldehydes, $C_2$-$C_4$-ketones, and mixtures of two or more thereof. According to yet further preferred embodiments of the inventive process, the gas stream provided in step (i) comprises one or more oxygenates selected from the group consisting of methanol, ethanol, n-propanol, isopropanol, butanol, dimethyl ether, diethyl ether, ethyl methyl ether, diisopropyl ether, di-n-propyl ether, formaldehyde, dimethyl ketone, and mixtures of two or more thereof, wherein it is yet further preferred that the one or more oxygenates comprised in the gas stream according to (i) is selected from the group consisting of methanol, ethanol, n-propanol, isopropanol, butanol, dimethyl ether, diethyl, ethyl methyl ether, diisopropyl ether, di-n-propyl ether, formaldehyde, dimethyl ketone, and mixtures of two or more thereof, and more preferably from the group consisting of methanol, ethanol, dimethyl ether, diethyl ether, ethyl methyl ether, and mixtures of two or more thereof. According to particularly preferred embodiments of the inventive process for the conversion of oxygenates to olefins, the gas stream provided in step (i) comprises methanol and/or dimethyl ether, wherein it is particularly preferred that dimethyl ether is comprised as the one or more oxygenates in the gas stream according to (i).

Therefore, embodiments of the inventive process are preferred wherein the gas stream provided in step (i) contains one or more oxygenates selected from the group consisting of aliphatic alcohols, ethers, carbonyl compounds, and mixtures of two or more thereof.

Regarding the content of oxygenates in the gas stream according to (i) in the inventive process for the conversion of oxygenates to olefins, no particular restriction applies provided that the contacting of the gas stream according to (ii) with the catalyst comprising a zeolitic material according to the present invention allows for the conversion of at least one oxygenate to at least one olefin. According to a preferred embodiment of the inventive process, the content of oxygenates in the gas stream according to (i) lies in the range of from 30 to 100 vol.-% based on the total volume of the gas stream, wherein the content refers in particular to a gas stream at a temperature in the range of from 200 to 700° C. and at a pressure of 101.3 kPa, preferably at a temperature in the range of from 250 to 650° C., more preferably at a temperature of from 300 to 600° C., more preferably at a temperature of 350 to 560° C., more preferably at a temperature in the range of from 400 to 540° C., more preferably at a temperature in the range of from 430 to 520° C., and more preferably at a temperature in the range of from 450 to 500° C. at a pressure of 101.3 kPa. According to the present invention, it is further preferred that the content of oxygenates in the gas stream according to (i) is comprised in the range of from 30 to 99.9 vol.-% based on the total volume of the gas stream, and more preferably in the range of from 30 to 99 vol.-%, more preferably from 30 to 95 vol.-%, more preferably from 30 to 90 vol.-%, more preferably from 30 to 80 vol.-%, more preferably from 30 to 70 vol.-%, more preferably from 30 to 60 vol.-%, and more preferably from 30 to 50 vol.-%. According to a particularly preferred embodiment of the inventive process, the content of the one or more oxygenates in the gas stream according to (i) lies in the range of from 30 to 45 vol.-%.

Therefore, embodiments of the inventive process for the conversion of oxygenates to olefins are preferred, wherein the gas stream provided in step (i) contains from 30 to 100 vol.-% of oxygenates based on the total volume of the gas stream.

Regarding the further components which may be contained in the gas stream according to (i) of the inventive process, in principle there is no restriction neither with respect to the number nor with respect to the amount of said one or more further components to the one or more oxygenates, provided that when bringing said gas stream into contact with a zeolitic material according to the present invention in step (ii), at least one of the one or more oxygenates may be converted to at least one olefin. Accordingly, one or more inert gases may for example be contained in the gas stream according to (i) in addition to the one or more oxygenates such as for example one or more noble gases, nitrogen gas, carbon monoxide, carbon dioxide, water, and mixtures of two or more thereof. Alternatively, or in addition to these, the one or more inert gases may comprise unwanted side-products which are recycled such as paraffins, olefinic products with 5 or more carbon atoms, aromatics, or mixtures of two or more thereof, which are produced according to any of the particular and preferred embodiments of the inventive process for the conversion of oxygenates to olefins. According to particularly preferred embodiments of the present invention, the gas stream according to (i) of the inventive process further comprises water in addition to the one or more oxygenates.

According to the particularly preferred embodiments of the inventive process, wherein water is contained in the gas stream according to (i) in addition to the one or more oxygenates, no restriction applies in principle relative to the amount of water which may be contained in the gas stream, provided that at least one of the oxygenates may be converted in step (ii) to at least one olefin upon contacting of the gas stream with a catalyst according to the present invention. Thus, by way of example, the gas stream provided in step (i) may contain 60 vol.-% water or less based on the total volume of the gas stream, wherein according to particular embodiments which are preferred the water content in the gas stream ranges from 5 to 60 vol.-% based on the total volume of the gas stream, wherein it is preferred that the water content ranges from 10 to 55 vol. %, and more preferably from 20 to 50 vol.-%. According to particularly preferred embodiments of the present invention, water is contained in the gas stream according to (i) in an amount of 30 to 45 vol.-% in addition to the one or more oxygenates.

According to alternatively preferred embodiments, however, little to no water is contained in the gas stream provided in step (i) and in particular, the water content in the gas stream is 5 vol.-% or less, more preferably 3 vol.-% or less, more preferably 1 vol.-% or less, more preferably 0.5 vol.-% or less, more preferably 0.1 vol.-% or less, more preferably 0.05 vol.-% or less, more preferably 0.01 vol.-% or less, more preferably 0.005 vol.-% or less, and more preferably 0.001 vol.-% or less.

Therefore, embodiments of the inventive process are preferred wherein the gas stream provided in step (i) contains 60 vol.-% or less of water based on the total volume of the gas stream.

According to a particularly preferred embodiment of the inventive process for the conversion of oxygenates to olefins, the gas stream according to (i) originates from a pre-reaction, preferably from the conversion of one or more alcohols to one or more ethers, and in particular from the conversion of one or more alcohols selected from the group consisting of methanol, ethanol, n-propanol, isopropanol, and mixtures of two or more thereof, more preferably from the group consisting of methanol, ethanol, n-propanol, and mixtures of two or more thereof, wherein it is particularly preferred that the gas stream provided in (i) originates from a pre-reaction of methanol and/or ethanol and preferably from methanol which at least in part is converted to one or more di-$C_1$-$C_2$-alkyl ethers, preferably to one or more di-$C_1$-$C_2$-alkyl ethers selected from the group consisting of dimethylether, diethylether, ethylmethylether, and mixtures of two or more thereof. According to a particularly preferred embodiment of the inventive process, the gas stream provided in step (i) originates from a pre-reaction, wherein methanol is at least in part converted to dimethylether.

According to the particularly preferred embodiments of the present invention, wherein the gas stream provided in step (i) originates from a pre-reaction of one or more alcohols, there is principally no particular restriction relative to the reaction and to the reaction products of the conversion of one or more alcohols, provided that the pre-reaction leads to a gas stream comprising one or more oxygenates which upon contacting with a catalyst according to the invention in step (ii) may lead to the conversion of one of the oxygenates to at least one olefin. According to said preferred embodiments, it is further preferred that the pre-reaction for the conversion of at least one alcohol leads to at least one ether and in particular to at least one dialkyl ether, wherein it is particularly preferred that the pre-reaction is a dehydration reaction, wherein water is produced as a secondary product from the condensation reaction to one or more dialkyl ethers. According to the particular and preferred embodiments of the present invention wherein the gas stream provided in step (i) originates from a pre-reaction, it is particularly preferred according to the inventive process that a gas stream resulting from such a pre-reaction is directly provided in step (i) of the inventive process without having been subject to any type of workup.

As regards the particular conditions under which the gas stream is contacted with a catalyst according to the present invention in step (ii), no particular restriction applies in this respect provided that the conversion of at least one oxygenate to at least one olefin may be realized. This, for example, applies to the temperature at which the contacting in step (ii) takes place. Accordingly, said contacting of the gas stream in step (ii) may be conducted according to the inventive process at a temperature in the range of from 200 to 700° C., wherein it is preferred that the contacting is conducted at a temperature in the range of from 250 to 650° C., more preferably of from 300 to 600° C., more preferably of from 350 to 560° C., more preferably of from 400 to 540° C., and more preferably of from 430 to 520° C. According to a particularly preferred embodiment of the inventive process, the contacting of the gas stream in step (ii) is conducted at a temperature in the range of from 450 to 500° C.

Accordingly, embodiments of the inventive process are preferred wherein contacting of the gas stream with the zeolitic material in step (ii) is performed at a temperature in the range of 200 to 700° C.

Same applies accordingly relative to the pressure under which the gas stream is contacted with a catalyst according to the present invention in step (ii) of the inventive process. Thus, in principle, said contacting may be conducted at any conceivable pressure, provided that at least one oxygenate may be converted to at least one olefin upon contacting of the gas stream with the catalyst. Accordingly, by way of example, the contacting in step (ii) may be conducted at a pressure in the range of from 0.1 to 10 bar, wherein the pressure as defined in the present application designates the absolute pressure such that a pressure of 1 bar upon contacting of the gas stream with the catalyst corresponds to the normal pressure of 1.03 kPa. According to the inventive process, contacting in step (ii) is preferably performed at a pressure of from 0.3 to 7 bar, more preferably of from 0.5 to 5 bar, more preferably of from 0.7 to 3 bar, more preferably of from 0.8 to 2.5 bar, and more preferably of from 0.9 to 2.2 bar. According to a particularly preferred embodiment of the inventive process, contacting of the gas stream in step (ii) is conducted at a pressure of from 1 to 2 bar.

Therefore, embodiments of the present invention are preferred, wherein contacting of the gas stream with the zeolitic material in step (ii) is performed at a pressure in the range of 0.1 to 10 bar.

Furthermore, no particular restriction applies relative to the manner in which the inventive process for the conversion of oxygenates to olefins is conducted, such that both a non-continuous mode as well as a continuous mode may be applied to the inventive process, wherein the non-continuous process may for example be conducted as a batch-process. According to the present invention, it is, however, preferred that the inventive process for the conversion of oxygenates to olefins is at least in part performed in a continuous mode.

As regards the preferred embodiments of the inventive process, wherein it is at least in part performed in a continuous mode, in principle no restrictions apply relative to the weight hourly space velocity (WHSV) at which the process is conducted, provided that the conversion of at least one oxygenate to at least one olefin may be realized. Accordingly, weight hourly space velocities may be chosen for the contacting in step (ii) which lie in the range of from 0.5 to 50 $h^{-1}$, wherein preferably weight hourly space velocities of from 1 to 30 $h^{-1}$ are chosen, more preferably of from 2 to 20 $h^{-1}$, more preferably of from 3 to 15 $h^{-1}$, and more preferably of from 4 to 10 $h^{-1}$. According to a particularly preferred embodiment of the inventive process, wherein at least part is performed in a continuous mode, weight hourly space velocities ranging from 5 to 7 $h^{-1}$ are chosen for the contacting of the gas stream in step (ii) with a catalyst according to the present invention.

As regards the preferred weight hourly space velocities according to preferred embodiments of the inventive process for the conversion of oxygenates to olefins, said weight hourly space velocities are preferably adjusted in function of the conversion of the one or more oxygenates comprised in the gas stream provided in step (i) of the inventive process, and in particular adjusted such that a certain level of conversion comprised in a specific range is achieved. Thus, according to the particular and preferred embodiments of the inventive process, the weight hourly space velocities may be adjusted such that the conversion of the one or more oxygenates lies in the range of from 50 to 99.9%. According to the present invention, weight hourly space velocities are preferred according to the particular and preferred embodiments of the inventive process wherein the conversion of the oxygenates lies in the range of from 70 to 99.5%, more preferably from 90 to 99%, more preferably from 95 to 98.5%, more preferably from 96 to 98%, and even more preferably from 96.5 to 97.5%. According to the inventive process, it is however yet further preferred that the weight hourly space velocity under which the gas stream in step (ii) is contacted with a catalyst according to the present invention is adjusted to assure full conversion of the one or more oxygenates, i.e. a conversion of from 96.5 to 99.9% or more thereof, more preferably a conversion of the one or more oxygenates of from 97.5 to 99.9% or more thereof, more preferably of from 98 to 99.9% or more thereof, more preferably of from 99 to 99.9% or more thereof, and more preferably of from 99.5 to 99.9% or more relative to the conversion of the one or more oxygenates.

Therefore, embodiments of the inventive process are further preferred wherein the weight hourly space velocity (WHSV) of the gas stream in step (ii) ranges from 0.5 to 50 $h^{-1}$.

As to the zeolitic material which is obtainable and/or obtained according to a method as defined in any of the particular or preferred embodiments of the present application, said zeolitic material may be any suitable zeolitic material having an MFI, MEL, and/or MWW-type framework structure, provided that it may act as a catalyst in the conversion of at least one oxygenate to at least one olefin. According to preferred embodiments of the inventive process, the zeolitic material comprises one or more zeolites having the MFI-type framework structure. Among the preferred zeolitic materials comprising one or more zeolites having the MFI-type framework structure, there is no particular restriction neither with respect to the type and/or number thereof, nor with respect to the amount thereof in the zeolitic material, provided that said material is obtainable and/or obtained by a method according to any of the particular or preferred embodiments defined in the present application, and that it may act as a catalyst in the conversion of at least one oxygenate to at least one olefin.

According to embodiments of the inventive process wherein the zeolitic material which is obtainable and/or obtained according to the method of the present application comprises one or more zeolites having an MWW-type framework structure, there is also no particular restriction neither with respect to the type, nor with respect to the number of zeolites having an MWW-type framework structure which may be contained therein. Thus, by way of example, the one or more zeolites having MWW-type framework structure which are obtainable and/or obtained according to the method as described in the present application may include one or more zeolites selected from the group consisting of MCM-22, [Ga—Si—O]-MWW, [Ti—Si—O]-MWW, ERB-1, ITQ-1, PSH-3, SSZ-25, and mixtures of two or more thereof, wherein preferably the one or more zeolites comprised in the zeolitic material comprise MCM-22 and/or MCM-36.

Same applies accordingly with respect to the one or more zeolites having MEL-type framework structure which may be comprised in the zeolitic material which is obtainable and/or obtained according to the method as described in the present application. Thus, again, by mere way of example, said one or more zeolites having an MEL-type framework structure which may be comprised in the zeolitic material employed in the inventive process may include one or more zeolites selected from the group consisting of ZSM-11, [Si—B—O]-MEL, Bor-D (MFI/MEL-intergrowth), Boralite D, SSZ-46, Silicalite 2, TS-2, and mixtures of two or more thereof, wherein preferably the one or more zeolites contained in the zeolitic material as obtainable and/or obtained according to the method as defined in any of the particular or preferred embodiments of the present application comprises ZSM-11.

As mentioned above, however, it is particularly preferred that the zeolitic material obtainable and/or obtained according to the method of the present application comprises one or more zeolites having an MFI-type framework structure. Again, no particular restriction applies, neither with respect to the type of the one or more zeolites having an MFI-type framework structure which may be comprised in the zeolitic material, nor with respect to the number or different types thereof, provided that they are obtainable and/or obtained according to the method of the present application. Thus, by way of example, the zeolitic material employed for the conversion of oxygenates to olefins may comprise one or more zeolites having an MFI-type framework structure selected from the group consisting of ZSM-5, ZBM-10, [As—Si—O]-MFI, [Fe—Si—O]-MFI, [Ga—Si—O]-MFI, AMS-1B, AZ-1, Bor-C, Boralite C, Encilite, FZ-1, LZ-105, monoclinic H-ZSM-5, Mutinaite, NU-4, NU-5, Silicalite, TS-1, TSZ, TSZ-III, TZ-01, USC-4, USI-108, ZBH, ZKQ-1B, ZMQ-TB, and mixtures of two or more thereof, wherein preferably the zeolitic material comprises ZSM-5 and/or ZBM-10 as the one or more zeolites having an MFI-type framework structure preferably contained therein. As regards the zeolitic material ZBM-10 and its characterization, reference is made herewith to the disclosure of EP 0 007 081 A1 and EP 0 34 727 A2, respectively. According to particularly preferred embodiments of the inventive process, the zeolitic material obtainable and/or obtained according to the method of the present application comprises ZSM-5 as the preferred zeolite having an MFI-framework structure.

Therefore, embodiments of the inventive process are preferred wherein the zeolitic material obtainable and/or obtained according to a method as defined in the present application comprises ZSM-5.

As regards the zeolitic material which is comprised in the catalyst used in the inventive process and which is obtainable and/or obtained according to the method of the present application, said zeolitic material is accordingly characterized by having an MFI, MEL, and/or MWW-type framework structure comprising $YO_2$ and $X_2O_3$, wherein Y is a tetravalent element and X is a trivalent element, wherein the zeolitic material contains 3 wt.-% or less of one or more elements M, wherein M in general stands for sodium.

With respect to the zeolitic material having an MFI, MEL, and/or MWW-type framework structure which is obtainable and/or obtained according to the method as defined in the present application and which is employed in the inventive process, no particular restriction applies, neither relative to the particle size and particle size distribution thereof nor with respect to their crystal habit. According to preferred embodiments of the inventive process, however, 95% by weight or more of the primary particles of the zeolitic material obtainable and/or obtained according to the method of the present application have a diameter of less than or equal to 1 μm. According to the present invention, it is further preferred that 96% by weight or more of the primary particles of the zeolitic material obtainable and/or obtained according to the method of the present application have a diameter of less than or equal to 1 μm, and more preferably 97% by weight or more, more preferably 98% by weight or more, wherein it is particularly preferred that 99% by weight or more of the primary particles of the zeolitic material have a diameter of less than or equal to 1 μm.

Therefore, embodiments of the inventive process are preferred wherein 95% by weight or more of the primary particles of the zeolitic material obtainable and/or obtained according to a method as defined in the present application have a diameter of less than or equal to 1 μm. Regarding the primary particles of the present invention, as for the zeolitic material, there is no particular restriction as to their crystal habit, wherein according to the present invention it is preferred that at least a portion of the primary particles are spherical.

The term "spherical" as used in the context of the present invention denotes primary particles which, on investigation by scanning electron microscopy (SEM) at a magnification of from $0.5 \times 10^4$ to $2.0 \times 10^4$, and preferably of from $2.0 \times 10^4$ to $75 \times 10^4$ are substantially free of sharp edges. Accordingly, the term "spherical" denotes, for example, purely spherical or deformed spherical, for example elliptical or cuboid primary particles, wherein the edges are rounded and not sharp in the case of the cuboid primary particles in the abovementioned investigation method in said resolution range.

According to the preferred embodiments of the present invention wherein at least a portion of the primary particles are spherical, it is preferred that 50% or more of the primary particles are spherical, more preferably 60% or more, more preferably 70% or more, more preferably 80% or more, more preferably 85% or more, and more preferably 90% or more. According to yet further preferred embodiments of the present invention, 91% or more of the primary particles, more preferably 92% or more, more preferably 93% or more, more preferably 94% or more, more preferably 95% or more, more preferably 96% or more, and more preferably 97% of the primary particles of the zeolitic material are spherical.

According to preferred embodiments wherein at least a portion of the primary particles are spherical, it is particularly preferred that 95% by weight or more of the spherical primary particles have a diameter of less than or equal to 1 μm. More preferred are diameters of 900 nm or less, more preferably 800 nm or less, more preferably 700 nm or less, more preferably 600 nm or less, and more preferably 500 nm or less. More preferably, the primary particles of the zeolitic material have a diameter in the range of 5 nm or more, more preferably 10 nm or more, more preferably 20 nm or more, more preferably 30 nm or more, particularly preferably 50 nm or more. The diameters are particularly preferably in the range of from 5 to 800 nm, preferably from 10 to 500 nm, more preferably from 20 to 400 nm, more preferably from 30 to 300 nm, more preferably from 40 to 250 nm, and more preferably from 50 to 200 nm.

Therefore, embodiments of the present invention are further preferred, wherein 95% by weight of more of the primary particles of the zeolitic material obtainable and/or obtained according to a method as defined in the present application have a diameter of from 5 to 800 nm, preferably from 10 to 500 nm, more preferably from 20 to 400 nm, more preferably from 30 to 300 nm, more preferably from 40 to 250 nm, and more preferably from 50 to 200 nm.

Furthermore, embodiments of the present invention are preferred, wherein 90% or more of the primary particles are spherical, and wherein preferably 95% by weight or more of the spherical primary particles have a diameter of less than or equal to 1 μm, and more preferably of from 5 to 800 nm, more preferably from 10 to 500 nm, more preferably from 20 to 400 nm, more preferably from 30 to 300 nm, more preferably from 40 to 250 nm, and more preferably from 50 to 200 nm.

Therefore, embodiments of the inventive process are further preferred wherein 90% or more of the primary particles of the zeolitic material comprised in the catalyst used therein which is obtainable and/or obtained according to a method as defined in the present application are spherical, and wherein preferably 95% by weight or more of the spherical primary particles have a diameter of less than or equal to 1 μm.

The diameters of the primary particles as described in the context of the present invention may be determined, for example, via the electron microscopic methods SEM (scanning electron microscopy) and TEM (transmission electron microscopy). The diameters described in the context of the present invention were determined by SEM.

According to the present invention, the zeolitic material obtainable and/or obtained according to a method as defined in the present application having an MFI, MEL, and/or MWW-type framework structure contains 3 wt.-% or less of one or more elements M based on 100 wt.-% of $YO_2$, wherein M stands for sodium. As regards the amount of the one or more elements M calculated by weight according to the present invention, said amount refers to the weight of said one or more elements calculated as the element as opposed to being calculated as the oxide or the like. According to the invention, it is further preferred that the one or more elements M, of which the zeolitic material contains 3 wt.-% or less, stands for the group of alkaline metals and in particular for Li, Na, K, Rb, and Cs. According to yet further preferred embodiments, M stands for the group of both alkali and alkaline earth metals, wherein the alkaline earth metals wherein said alkaline earth metals refer in particular to the elements Mg, Ca, Sr, and Ba.

As regards the respective amounts of $YO_2$ and $X_2O_3$ comprised in the zeolitic material obtainable and/or obtained according to a method as defined in the present application having an MFI, MEL, and/or MWW-type framework structure, there is no particular restriction as to the amounts in which they may be respectively contained therein, nor with respect to the molar ratio of $YO_2$ to $X_2O_3$ displayed by the zeolitic material. Thus, by way of example, the zeolitic material may display a $YO_2$:$X_2O_3$ atomic ratio ranging anywhere from 10 to 1500, wherein preferably the atomic ratio ranges from 30 to 1200, more preferably from 50 to 900, more preferably from 70 to 700, more preferably from 80 to 500, and even more preferably from 90 to 300. According to particularly preferred embodiments of the present invention, the zeolitic material obtainable and/or obtained according to a method as defined in the present application having an MFI, MEL, and/or MWW-type framework structure displays a $YO_2$:$X_2O_3$ atomic ratio in the range of from 100 to 250.

Therefore, embodiments of the inventive process are preferred wherein the zeolitic material obtainable and/or obtained according to a method as defined in the present application displays a $YO_2$:$X_2O_3$ atomic ratio of from 10 to 1,500.

According to the present invention, the zeolitic material obtainable and/or obtained according to a method as defined in the present application having an MFI, MEL, and/or MWW-type framework structure comprises $YO_2$. In principle, Y stands for any conceivable tetravalent element, Y standing for either one or several tetravalent elements. Preferred tetravalent elements according to the present invention include Si, Sn, Ti, Zr, Ge, and mixtures of two or more thereof. According to the present invention, however, it is particularly preferred that Y comprises Si, wherein more preferably Y is Si.

Therefore, embodiments of the inventive process are preferred wherein with respect to the zeolitic material used therein which is obtainable and/or obtained according to a method as defined in the present application, the tetravalent element Y is selected from the group consisting of Si, Sn, Ti, Zr, Ge, and mixtures of two or more thereof, Y preferably being Si.

As regards $X_2O_3$ comprised in the zeolitic material having an MFI, MEL, and/or MWW-type framework structure according to the present invention, X may in principle stand for any conceivable trivalent element, wherein X stands for one or more several trivalent elements. Preferred trivalent elements according to the present invention include Al, B, In, Ga, and mixtures of two or more thereof. More preferably, X stands for Al, B, Ga, or mixtures of any two or more of said trivalent elements, wherein more preferably X comprises Al and/or Ga. According to particularly preferred embodiments of the present invention, X comprises Al, wherein more preferably X stands for Al.

Therefore, embodiments of the inventive process are preferred wherein with respect to the zeolitic material used therein which is obtainable and/or obtained according to a method as defined in the present application the trivalent X is selected from the group consisting of Al, B, In, Ga, and mixtures of two or more thereof, X preferably being Al and/or Ga, and more preferably being Al.

As concerns the specific zeolitic material having an MFI, MEL, and/or MWW-type framework structure comprised in the catalyst employed in the inventive process, there is no particular restriction as to the specific MFI and/or MEL and/or MWW-type material which may be used in the inventive process, such that any suitable one or more zeolites having an MFI and/or MEL and/or MWW-type framework structure may be contained therein provided that they are obtainable and/or obtained according to a method as defined in the present application, respectively, and provided that in the inventive process at least one of the oxygenates may be converted to at least one olefin.

Furthermore, there is no particular restriction according to the present invention as to the suitable physical and/or chemical characteristics of the zeolitic material, provided that it is obtainable and/or obtained according to a method as defined in the present application. Thus, as regards, for example, the porosity and/or surface area of the zeolitic material, these may adopt any conceivable values. In particular, as regards the BET surface area of the zeolitic material as determined according to DIN 66131, it may accordingly range anywhere from 200 to 900 $m^2/g$, wherein preferably the BET surface area ranges from 250 to 700 $m^2/g$, more preferably from 300 to 600 $m^2/g$, more preferably from 350 to 550 $m^2/g$, more preferably from 380 to 500 $m^2/g$, more preferably from 400 to 470 $m^2/g$, and more preferably from 420 to 450 $m^2/g$. According to particularly preferred embodiments of the present invention, the BET surface area of the zeolitic material obtainable and/or obtained according to a method as defined in the present application as determined according to DIN 66131 ranges from 425 to 445 $m^2/g$.

Therefore, embodiments of the inventive process are preferred wherein the BET surface area of the zeolitic material obtainable and/or obtained according to a method as defined in the present application is determined according to DIN 66131 ranges from 200 to 900 $m^2/g$.

According to the method of the present application according to which the zeolitic material is obtainable and/or obtained, one or more sources for $YO_2$ are provided in step (1). In principle, said one or more sources may be provided in any conceivable form provided that a zeolitic material having an MFI, MEL, and/or MWW-type framework structure comprising $YO_2$ can be crystallized in step (2). Preferably, $YO_2$ is provided as such and/or as a compound which comprises $YO_2$ as a chemical moiety and/or as a compound which (partly or entirely) is chemically trans-formed to $YO_2$ during the inventive process.

As regards $YO_2$ and/or precursors thereof employed in the method of the present application according to which the zeolitic material is obtainable and/or obtained, there is no particular restriction as to the one or more elements for which Y stands, provided that said element is a tetravalent element and that it is comprised in the zeolitic material having an MFI, MEL, and/or MWW-type framework structure crystallized in step (2). In particular, within the meaning of the present invention, $YO_2$ is at least partially and preferably entirely comprised in the MFI, MEL, and/or MWW-type framework structure of the zeolitic material as structure-building element, as opposed to non-framework elements which can be present in the pores and cavities formed by the framework structure and typical for zeolitic materials in general. As mentioned in the foregoing, Y may stand for any conceivable tetravalent element, Y standing either for a single or several tetravalent elements. Preferred tetravalent elements according to the present invention include Si, Sn, Ti, Zr, Ge, as well as any mixture of two or more thereof. According to preferred embodiments of the present invention, Y stands for Si.

In preferred embodiments of the method of the present application according to which the zeolitic material is obtainable and/or obtained, wherein Y stands for Si or for a combination of Si with one or more further tetravalent elements, the source for $SiO_2$ preferably provided in step (1) can also be any conceivable source. Thus, by way of example, any type of silicas and/or silicates and/or silica derivatives may be used, wherein preferably the one or more sources for $YO_2$ comprises one or more compounds selected from the group consisting of fumed silica, silica hydrosols, reactive amorphous solid silicas, silica gel, silicic acid, water glass, sesquisilicate, disilicate, colloidal silica, pyrogenic silica, silicic acid esters, or mixtures of any two or more of the afore-mentioned compounds may equally be used. Alternatively, or in addition to one or more of the aforementioned sources of $SiO_2$, elemental silicon may also be employed. According to particularly preferred embodiments, the one or more sources for $YO_2$ used in step (1) of the method of the present application according to which the zeolitic material is obtainable and/or obtained are selected from the group consisting of fumed silica, silica hydrosols, reactive amorphous solids, reactive amorphous sold silicas, silica gel, colloidal silica, pyrogenic silica, tetraalkoxy silanes, including mixtures of any two or more thereof. According to said particularly preferred embodiments, it is further preferred that the one or more sources for $YO_2$ are selected from the group consisting of fumed silica, reactive amorphous solid silicas, silica gel, pyrogenic silica, tetraalkoxy silanes, and mixtures of two or more thereof, wherein more preferably the one or more sources for $YO_2$ are selected from the group consisting of fumed silica, tetraalkoxy silanes, as well as mixtures of two or more thereof, wherein even more preferably according to the method of the present application according to which the zeolitic material is obtainable and/or obtained, the one or more sources for $YO_2$ comprises one or more tetraalkoxy silanes.

As regards the silicic acid esters which may be used according to particular and preferred embodiments of the present invention, said one or more esters preferably have the composition $$Si(OR)_{4-x}(OR')_x$$

wherein x is 0, 1, 2, 3 or 4, may be used as $SiO_2$ source, where R and R' may be different from one another and may each be hydrogen, $C_1$-$C_8$-alkyl, for example methyl, ethyl, n-propyl, isopropyl, n-butyl, isobutyl, tert-butyl, pentyl, hexyl, heptyl or octyl, $C_4$-$C_8$-cycloalkyl, such as cyclobutyl, cyclopentyl, cyclohexyl, cycloheptyl or cyclooctyl, aryl, alkylaryl or arylalkyl, or where R and R' may be identical and may each be hydrogen, $C_1$-$C_8$-alkyl, for example methyl, ethyl, n-propyl, isopropyl, n-butyl, isobutyl, tert-butyl, pentyl, hexyl, heptyl or octyl, $C_4$-$C_8$-cycloalkyl, such as cyclobutyl, cyclopentyl, cyclohexyl, cycloheptyl or cyclooctyl, aryl, alkylaryl or arylalkyl.

According to a preferred embodiment of the method of the present application according to which the zeolitic material is obtainable and/or obtained, the one or more sources for $YO_2$ and in particular for $SiO_2$ comprises a compound of the general composition $$Si(OR)_4$$

or of the general composition $$Si(OR)_3(OR')$$

where R' is hydrogen and R is $C_1$-$C_8$-alkyl, for example methyl, ethyl, n-propyl, isopropyl, n-butyl, isobutyl, tert-butyl, pentyl, hexyl, heptyl or octyl.

According to particularly preferred embodiments wherein the one or more sources for $YO_2$ and in particular for $SiO_2$ comprises one or more tetraalkoxysilanes, it is further preferred that said one or more sources comprises one or more compounds of the general composition $$Si(OR)_4$$

wherein R is $C_1$-$C_8$-alkyl, for example methyl, ethyl, n-propyl, isopropyl, n-butyl, isobutyl, tert-butyl, pentyl, hexyl, heptyl or octyl, more preferably methyl, ethyl, n-propyl, isopropyl, n-butyl, isobutyl or tert-butyl, more preferably methyl, ethyl, n-propyl or isopropyl, more preferably methyl or ethyl, particularly preferably ethyl.

According to the method of the present application according to which the zeolitic material is obtainable and/or obtained, the mixture provided in step (1) further comprises one or more sources for $X_2O_3$, wherein X is a trivalent element. As regards the elements which may be employed as the trivalent element X comprised in the one or more sources for $X_2O_3$ provided in step (1), there is no particular restriction according to the present invention as to which elements or element mixtures may be employed, provided that a zeolitic material having an MFI, MEL, and/or MWW-type framework structure comprising $YO_2$ and $X_2O_3$ as framework elements may be obtained by crystallization in step (2). As mentioned in the foregoing, according to preferred embodiments of the present invention, X is selected from the group consisting of Al, B, In, Ga, and mixtures of two or more thereof, wherein preferably X is Al and/or B. According to particularly preferred embodiments of the present invention, X comprises Al, wherein even more preferably X is Al. As for $YO_2$ comprised in the zeolitic material having an MFI, MEL, and/or MWW-type framework structure, within the meaning of the present invention, $X_2O_3$ is also at least partially and preferably entirely comprised in the framework structure of the zeolitic material as structure-building element as opposed to non-framework elements which can be present in the pores and cavities formed by the framework structure and typical for zeolitic materials in general.

According to particularly preferred embodiments of the method of the present application according to which the zeolitic material is obtainable and/or obtained, wherein X stands for Al or for a combination of Al with one or more further trivalent elements, the source for $Al_2O_3$ preferably provided in step (1) can also be any conceivable source. In principle, any conceivable compounds which permit the preparation of the zeolitic material according to the method of the present application according to which the zeolitic material is obtainable and/or obtained may be used as the aluminum source. Thus, by way of example, the one or more sources for $Al_2O_3$ may comprise one or more compounds selected from aluminum, aluminum alkoxides, alumina, aluminates, and aluminum salts. In the process according to the present invention, the use of aluminum nitrate, aluminum sulfate or a trialkoxyaluminate of the composition $Al(OR)_3$ or a mixture of two or more of these compounds as aluminum source is particularly preferred. Regarding the trialkoxyaluminates of the composition $Al(OR)_3$, the radicals R may be identical or different from one another and are $C_1$-$C_8$-alkyl, for example methyl, ethyl, n-propyl, isopropyl, n-butyl, isobutyl, tert-butyl, pentyl, hexyl, heptyl or octyl, $C_4$-$C_8$-cycloalkyl, such as cyclobutyl, cyclopentyl, cyclohexyl, cycloheptyl or cyclooctyl, aryl, alkylaryl or arylalkyl. According to particularly preferred embodiments of the method of the present application according to which the zeolitic material is obtainable and/or obtained, the aluminum source used is aluminum sulfate. As regards the aluminum salts preferably employed, these may be used in their dehydrated form and/or as one or more hydrates or hydrated forms thereof.

As regards the amount in which the one or more sources for $YO_2$ and $X_2O_3$ may be provided in step (1) of the method of the present application according to which the zeolitic material is obtainable and/or obtained, no particular restriction applies provided that a zeolitic material having an MFI, MEL, and/or MWW-type framework structure comprising $YO_2$ and $X_2O_3$ may be crystallized in step (2). Same applies accordingly with respect to the relative amounts of the one or more sources for $YO_2$ and $X_2O_3$ which may be employed for preparing the mixture in step (1) such that in principle, no particular restriction applies with respect to the $YO_2$:$X_2O_3$ molar ratio which may be calculated for the mixture prepared in step (1) based on the respective amounts of the one or more sources for $YO_2$ and $X_2O_3$. Thus, by way of example, relative to the amount of the one or more sources for $YO_2$ provided in the mixture of step (1), the $YO_2$:$X_2O_3$ molar ratio of the mixture may range anywhere from 10 to 1,500, wherein preferably molar ratios are provided comprised in the range of from 30 to 1,200, more preferably from 50 to 900, more preferably from 70 to 700, more preferably from 80 to 500, and even more preferably of from 90 to 300. According to particularly preferred embodiments, the $YO_2$:$X_2O_3$ molar ratio of the mixture provided in step (1) is comprised in the range of from 100 to 250.

Therefore, embodiments of the method of the present application according to which the zeolitic material is obtainable and/or obtained are preferred wherein the $YO_2$:$X_2O_3$ molar ratio of the mixture prepared in step (1) ranges from 10 to 1,500.

According to alternatively preferred embodiments of the method of the present application according to which the zeolitic material is obtainable and/or obtained, however, the $YO_2$:$X_2O_3$ molar ratio of the mixture may range anywhere from 10 to 300, wherein preferably molar ratios are provided comprised in the range of from 30 to 220, more preferably from 50 to 180, more preferably from 70 to 150, more preferably from 90 to 120, and even more preferably of from 95 to 105. According to further embodiments of the method of the present application according to which the zeolitic material is obtainable and/or obtained which are alternatively preferred, the $YO_2$:$X_2O_3$ molar ratio of the mixture may range anywhere from 50 to 500, wherein preferably molar ratios are provided comprised in the range of from 100 to 400, more preferably from 150 to 350, more preferably from 200 to 300, more preferably from 220 to 280, and even more preferably of from 240 to 260.

According to the method of the present application according to which the zeolitic material is obtainable and/or obtained, the mixture provided in step (1) further comprises one or more solvents. In principle, there is no particular restriction according to the present invention neither with respect to the type and/or number of the one or more solvents, nor with respect to the amount in which they may be used in the inventive process provided that a zeolitic material having an MFI, MEL, and/or MWW-type framework structure may be crystallized in step (2). According to the method of the present application according to which the zeolitic material is obtainable and/or obtained, it is however preferred that the one or more solvents comprise one or more polar solvents, wherein the one or more polar solvents are preferably selected from the group consisting of alkanols, water, and mixtures of two or more thereof. According to particularly preferred embodiments, the one or more solvents comprise one or more polar solvents selected from the group consisting of methanol, ethanol and/or propanol, iso-propanol, water, and mixtures of two or more thereof, and more preferably from the group consisting of methanol, ethanol, water, and mixtures of two or more thereof. According to the method of the present application according to which the zeolitic material is obtainable and/or obtained is, however, further preferred that the one or more solvents and in particular the one or more polar solvents comprise water, and more preferably, distilled water, wherein according to particularly preferred embodiments distilled water is used as the only solvent in the mixture provided in step (1) and crystallized in step (2).

Therefore, embodiments of the method of the present application according to which the zeolitic material is obtainable and/or obtained are preferred, wherein the one or more solvents comprise one or more polar solvents, wherein the one or more polar solvents are preferably selected from the group consisting of alkanols, water, and mixtures of two or more thereof.

According to preferred embodiments of the method of the present application according to which the zeolitic material is obtainable and/or obtained, the mixture provided in step (1) and crystallized in step (2) further comprises one or more organotemplates. In principle, according to the present invention, there is no particular restriction neither with respect to the number nor with respect to the type of the one or more organotemplates which may be used therein provided that a zeolitic material having an MFI, MEL, and/or MWW-type framework structure is crystallized in step (2) from the mixture obtained in step (1). It is, however, preferred according to the method of the present application according to which the zeolitic material is obtainable and/or obtained that the one or more organotemplates comprise one or more compounds selected from the group consisting of tetraalkylammonium and alkenyltrialkylammonium compounds. As regards the alkyl moieties which may be comprised in the tetraalkylammonium and alkenyltrialkylammonium compounds, again no particular restriction applies in this respect provided that a zeolitic material having an MFI, MEL, and/or MWW-type framework structure may be crystallized in step (2). Accordingly, any conceivable alkyl moieties including combinations of two or more alkyl moieties may be contained in the respective one or more tetraalkylammonium and/or one or more alkenyltrialkylammonium compounds wherein preferably the alkyl moieties are selected from the group consisting of $C_1$-$C_8$-alkyl, more preferably from the group consisting of $C_1$-$C_6$-alkyl, more preferably $C_1$-$C_5$-alkyl, and more preferably from the group consisting of $C_1$-$C_4$-alkyl. According to particularly preferred embodiments of the present invention, the alkyl moieties respectfully comprised in the one or more tetraalkylammonium and/or alkenyltrialkylammonium compounds is selected from the group consisting of $C_1$-$C_3$-alkyl.

As concerns the alkenyl moiety contained in the alkenyltrialkylammonium cation of the one or more alkenyltrialkylammonium compounds preferably comprised among the one or more organotemplates, again, no particular restriction applies in this respect provided that a zeolitic material having an MFI, MEL, and/or MWW-type framework structure may be crystallized in step (2). According to particularly preferred embodiments of the present invention, however, the alkenyl moiety of the alkenyltrialkylammonium cation is selected from the group consisting of $C_2$-$C_6$-alkenyl, more preferably from the group consisting of $C_2$-$C_5$-alkenyl, more preferably $C_2$-$C_4$-alkenyl, and even more preferably from the group consisting of $C_2$-$C_3$-alkenyl. According to particularly preferred embodiments thereof, the alkenyl moiety of the alkenyltrialkylammonium cation comprised in the one or more alkenyltrialkylammonium compounds preferably comprised among the one or more organotemplates is 2-propene-1-yl, 1-propene-1-yl, or 1-propene-2-yl, wherein according to particularly preferred embodiments thereof, the alkenyl moiety is 2-propene-1-yl or 1-propene-1-yl.

Therefore, embodiments of the method of the present application according to which the zeolitic material is obtainable and/or obtained are preferred, wherein the mixture in step (1) further comprises one or more organotemplates, the one or more organotemplates preferably comprising one or more compounds selected from the group consisting of tetraalkylammonium and alkenyltrialkylammonium compounds.

According to yet further preferred embodiments of the method of the present application according to which the zeolitic material is obtainable and/or obtained, wherein the one or more organotemplates preferably comprised in the mixture prepared in step (1) comprises one or more tetraalkylammonium compounds, it is preferred that said compounds are selected from the group consisting of tetraethylammonium compounds, triethylpropylammonium compounds, diethyldipropylammonium compounds, ethyltripropylammonium compounds, tetrapropylammonium compounds, and mixtures of two or more thereof, wherein it is particularly preferred that the one or more organotemplates comprises one or more tetrapropylammonium compounds.

Likewise, as regards particularly preferred embodiments of the method of the present application according to which the zeolitic material is obtainable and/or obtained, wherein the one or more organotemplates preferably comprised in the mixture prepared in step (1) comprise one or more alkenyltrialkylammonium compounds, it is particularly preferred that these are selected from the group consisting of N—($C_2$-$C_5$)-alkenyl-tri-($C_1$-$C_5$)-alkylammonium compounds, and more preferably are selected from the group consisting of N—($C_2$-$C_4$)-alkenyl-tri-($C_1$-$C_4$)-alkylammonium compounds, more preferably from the group consisting of N—($C_2$-$C_3$) alkenyl-tri-($C_2$-$C_4$) alkylammonium compounds, wherein even more preferably these are selected from the group consisting of N-(2-propene-1-yl)-tri-n-propylammonium compounds, N-(1-propene-1-yl)-tri-n-propylammonium compounds, N-(1-propene-2-yl)-tri-n-propylammonium compounds, including mixtures of two or more thereof. According to particularly preferred embodiments thereof, the one or more alkenyltrialkylammonium compounds preferably comprised in the mixture prepared in step (1) is selected from the group consisting of N-(2-propene-1-yl)-tri-n-propylammonium compounds, N-(1-propene-1-yl)-tri-n-propylammonium compounds, and mixtures of two or more thereof.

As regards the one or more tetraalkylammonium and/or alkenyltrialkylammonium compounds further added to the mixture prepared in step (1) according to particularly preferred embodiments of the method of the present application according to which the zeolitic material is obtainable and/or obtained, said one or more compounds are accordingly provided in the form of a salt. As regards the counterion to the one or more tetraalkylammonium and/or alkenyltrialkylammonium cations contained in said one or more compounds, again no particular restriction applies according to the present invention provided that an MFI, MEL, and/or MWW-type framework structure may be crystallized in step (2) of the method of the present application according to which the zeolitic material is obtainable and/or obtained. Thus, any conceivable counterion to said one or more cations may be employed for providing the one or more tetraalkylammonium and/or alkenyltrialkylammonium compounds. Thus, by way of example, the one or more counterions to the one or more tetraalkylammonium and/or alkenyltrialkylammonium salts may comprise one or more anions selected from the group consisting of chloride, fluoride, bromide, carbonate, hydrogen carbonate, hydroxide, nitrate, phosphate, hydrogen phosphate, dihydrogen phosphate, sulfate, hydrogen sulfate, acetate, formate, oxalate, cyanate, and mixtures of two or more thereof, more preferably from the group consisting of chloride, fluoride, bromide, hydrogen carbonate, hydroxide, nitrate, dihydrogen phosphate, hydrogen sulfate, acetate, formate, oxalate, and combinations of two or more thereof, wherein even more preferably the one or more counterions comprise one or more anions selected from the group consisting of chloride, bromide, hydroxide, nitrate, and combinations of two or more thereof.

According to particularly preferred embodiments of the present invention, the one or more tetraalkylammonium and/or alkenyltrialkylammonium salts preferably added to the mixture prepared in step (1) and crystallized in step (2) of the method of the present application according to which the zeolitic material is obtainable and/or obtained are, independently from one another, a hydroxide and/or a halide salt, and more preferably a salt selected from the group consisting of hydroxide, chloride, bromide, and mixtures of two or more thereof, wherein even more preferably the salts comprise one or more hydroxides. Thus, according to particularly preferred embodiments of the method of the present application according to which the zeolitic material is obtainable and/or obtained, wherein the one or more organotemplates comprises one or more tetraalkylammonium compounds, it is particularly preferred that said one or more organotemplates comprises tetrapropylammonium hydroxide and/or chloride, and even more preferably tetrapropylammonium hydroxide. Likewise, according to particularly preferred embodiments of the method of the present application according to which the zeolitic material is obtainable and/or obtained, wherein the one or more organotemplates preferably added to the mixture prepared in step (1) comprises one or more alkenyltrialkylammonium compounds, it is particularly preferred that the one or more organotemplates comprises N-(2-propene-1-yl)-tri-n-propylammonium and/or N-(1-propene-1-yl)-tri-n-propylammonium hydroxide and/or chloride, and even more preferably N-(2-propene-1-yl)-tri-n-propylammonium hydroxide and/or N-(1-propene-1-yl)-tri-n-propylammonium hydroxide.

As regards the amount in which the one or more organotemplates are preferably comprised in the mixture prepared in step 1 of the method of the present application according to which the zeolitic material is obtainable and/or obtained according to which one or more organotemplates are preferably provided for crystallizing a zeolitic material having an MFI, MEL, and/or MWW-type framework structure, no particular restriction applies. Thus, by way of example, the molar ratio of the total amount of the one or more organotemplates of the mixture obtained in step (1) to $YO_2$ may range anywhere from 1:0.1-1:30, wherein preferably the molar ratio ranges from 1:0.5-1:20, more preferably from 1:1-1:15, more preferably from 1:3-1:10, and more preferably from 1:4-1:7. According to particularly preferred embodiments thereof, the molar ratio of the total amount of the one or more organotemplates to $YO_2$ ranges from 1:5-1:5.6.

Therefore, embodiments of the method of the present application according to which the zeolitic material is obtainable and/or obtained are preferred, wherein the molar ratio of the total amount of the one or more organotemplates of the mixture obtained in step (1) to $YO_2$ ranges from 1: (0.1-30).

According to the method of the present application according to which the zeolitic material is obtainable and/or obtained, it is further preferred that the mixture according to step (1) comprises one or more sources for $OH^-$ for crystallizing an MFI, MEL, and/or MWW-type framework structure in step (2). As regards the particular type of source or sources for $OH^-$ which may be employed in the inventive process, no particular restriction applies provided that $OH^-$ anions may be directly and/or indirectly generated in the mixture prepared in step (1) and crystallized in step (2) of the method of the present application according to which the zeolitic material is obtainable and/or obtained. Within the meaning of the present invention, $OH^-$ anions are indirectly provided by any chemical reaction leading to the generation of $OH^-$ anions such as e.g. a reaction of a Lewis base with water, wherein a protonated form of the base and $OH^-$ are generated by chemical reaction of the former.

According to the present invention, the one or more sources for $OH^-$ preferably further comprised in the mixture according to step (1) preferably comprise one or more sources directly containing $OH^-$ and in particular one or more Broensted bases, wherein even more preferably said one or more sources for OH⁻ comprise one or more hydroxides of an organotemplate salt further comprised in the mixture prepared in step (1) according to any of the particular or preferred embodiments of the method of the present application according to which the zeolitic material is obtainable and/or obtained. Thus, according to a particularly preferred embodiment thereof, said one or more sources for OH⁻ preferably comprise one or more hydroxides selected from the group consisting of tetraalkylammonium and/or alkenyltrialkylammonium hydroxides, and more preferably one or more hydroxides selected from the group consisting of tetraethylammonium hydroxide, triethylpropylammonium hydroxide, diethyldipropylammonium hydroxide, ethyltripropylammonium hydroxide, tetrapropylammonium hydroxide, N-(2-propene-1-yl)-tri-n-propylammonium hydroxide, N-(1-propene-1-yl)-tri-n-propylammonium hydroxide, N-(1-propene-2-yl)-tri-n-propylammonium hydroxide, and mixtures of two or more thereof, wherein even more preferably the one or more hydroxides are selected from the group consisting of tetrapropylammonium hydroxide, N-(2-propene-1-yl)-tri-n-propylammonium hydroxide, N-(1-propene-1-yl)-tri-n-propylammonium hydroxide, and mixtures of two or more thereof. According to particularly preferred embodiments thereof, the one or more sources for OH⁻ comprise tetrapropylammonium hydroxide, wherein even more preferably the one or more sources for OH⁻ is tetrapropylammonium hydroxide.

Therefore, embodiments of the method of the present application according to which the zeolitic material is obtainable and/or obtained are preferred, wherein the mixture according to step (1) further comprises one or more sources for OH⁻, wherein said one or more sources for OH⁻ preferably comprises a hydroxide of an organotemplate salt, more preferably one or more hydroxides selected from the group consisting of tetraalkylammonium and/or alkenyltrialkylammonium hydroxides.

As concerns the amount of OH⁻ which may be comprised in the mixture prepared in step (1) of the method of the present application according to which the zeolitic material is obtainable and/or obtained, no particular restriction applies according to the present invention provided that a zeolitic material having MFI, MEL, and/or MWW-type framework structure may be crystallized in step (2) of the inventive process. Thus, by way of example, the OH⁻:YO₂ molar ratio of the mixture obtained in step (1) according to said preferred embodiments may range anywhere from 0.01 to 5, wherein preferably the OH⁻:YO₂ molar ratio ranges from 0.05 to 2, more preferably from 0.1 to 1, more preferably from 0.12 to 0.5, and more preferably from 0.15 to 0.3. According to particularly preferred embodiments of the method of the present application according to which the zeolitic material is obtainable and/or obtained, the OH⁻:YO₂ molar ratio of the mixture obtained in step (1) according to particular embodiments of the present invention ranges from 0.18 to 0.2.

In step (1) according to the method of the present application according to which the zeolitic material is obtainable and/or obtained, the mixture can be prepared by any conceivable means, wherein mixing by agitation is preferred, preferably by means of stirring.

As regards the crystallization performed in step (2) of the method of the present application according to which the zeolitic material is obtainable and/or obtained, no particular restriction applies according to the present invention as to the actual means employed for allowing the crystallization of a zeolitic material having an MFI, MEL, and/or MWW-type framework structure from the mixture obtained in step (1). Thus, any suitable means may be employed, wherein it is preferred that the crystallization is achieved by heating of the mixture of step (1). According to said preferred embodiments, again no particular restriction applies with respect to the temperature at which said crystallization in step (2) may be achieved, wherein it is preferred that the crystallization is conducted under heating at a temperature comprised in the range of from 80 to 250° C., more preferably from 100 to 220° C., more preferably from 120 to 200° C., more preferably from 140 to 180° C., and more preferably from 145 to 175° C. According to particularly preferred embodiments of the method of the present application according to which the zeolitic material is obtainable and/or obtained, the preferred heating of the mixture provided in step (1) in step (2) for the crystallization of a zeolitic material having an MFI, MEL, and/or MWW-type framework structure is conducted at a temperature comprised in the range of from 150 to 170° C.

Therefore, embodiments of the method of the present application according to which the zeolitic material is obtainable and/or obtained are preferred, wherein the crystallization in step (2) involves heating of the mixture, preferably at a temperature ranging from 80 to 250° C.

Concerning the heating preferably employed at step (2) of the method of the present application according to which the zeolitic material is obtainable and/or obtained as means for the crystallization of the zeolitic material having an MFI, MEL, and/or MWW-type framework structure, said heating may in principle be conducted under any suitable pressure provided that crystallization is achieved. In preferred embodiments of the present invention, the mixture according to step (1) is subjected in step (2) to a pressure which is elevated with regard to normal pressure. The term "normal pressure" as used in the context of the present invention relates to a pressure of 101,325 Pa in the ideal case. However, this pressure may vary within boundaries known to the person skilled in the art. By way of example, this pressure can be in the range of from 95,000 to 106,000 or of from 96,000 to 105,000, or of from 97,000 to 104,000, or of from 98,000 to 103,000, or of from 99,000 to 102,000 Pa.

In preferred embodiments of the method of the present application according to which the zeolitic material is obtainable and/or obtained, wherein a solvent is present in the mixture according to step (1), it is furthermore preferred that heating in step (2) is conducted under solvothermal conditions, meaning that the mixture is crystallized under autogenous pressure of the solvent which is used. This may for example be conducted by heating the mixture obtained in step (1) in an autoclave or other crystallization vessel suited for generated solvothermal conditions. In particularly preferred embodiments, wherein the solvent comprises water, and preferably distilled water, heating in step (2) is accordingly preferably conducted under hydrothermal conditions.

Therefore, embodiments of the method of the present application according to which the zeolitic material is obtainable and/or obtained are preferred, wherein the crystallization in step (2) is conducted under solvothermal conditions, preferably under hydrothermal conditions.

The apparatus which can be used in the method of the present application according to which the zeolitic material is obtainable and/or obtained for crystallization is not particularly restricted, provided that the desired parameters for the crystallization process can be realized, in particular with respect to the preferred embodiments requiring particular crystallization conditions. In the preferred embodiments conducted under solvothermal conditions, any type of autoclave or digestion vessel can be used.

Furthermore, as regards the period in which the preferred heating in step (2) of the method of the present application according to which the zeolitic material is obtainable and/or obtained is conducted for crystallizing the zeolitic material, there is again no particular restriction in this respect provided that the period of heating is suitable for achieving crystallization of a zeolitic material having an MFI, MEL, and/or MWW-type framework structure. Thus, by way of example, heating may be performed for a period of at least 3 hours, wherein preferably the period of heating may range anywhere from 6 hours to 15 days, more preferably from 9 hours to 10 days, more preferably from 12 hours to 7 days, more preferably from 15 hours to 5 days, more preferably from 18 hours to 4 days, and more preferably from 21 hours to 3 days. According to particularly preferred embodiments, heating in step (2) of the inventive process is conducted for a period of from 1 to 2 days.

Therefore, embodiments of the method of the present application according to which the zeolitic material is obtainable and/or obtained are preferred, wherein the crystallization in step (2) involves heating of the mixture for at least 3 h.

According to preferred embodiments of the method of the present application according to which the zeolitic material is obtainable and/or obtained, wherein the mixture is heated in step (2), said heating may be conducted during the entire crystallization process or during only one or more portions thereof, provided that a zeolitic material is crystallized. Preferably, heating is conducted during the entire duration of crystallization.

Further regarding the means of crystallization in step (2) of the method of the present application according to which the zeolitic material is obtainable and/or obtained, it is principally possible according to the present invention to perform said crystallization either under static conditions or by means of agitating the mixture. According to embodiments involving the agitation of the mixture, there is no particular restriction as to the means by which said agitation may be performed such that any one of vibrational means, rotation of the reaction vessel, and/or mechanical stirring of the reaction mixture may be employed to this effect wherein according to said embodiments it is preferred that agitation is achieved by stirring of the reaction mixture. According to alternatively preferred embodiments, however, crystallization is performed under static conditions, i.e. in the absence of any particular means of agitation during the crystallization process.

In general, the method of the present application according to which the zeolitic material is obtainable and/or obtained can optionally comprise further steps for the workup and/or further physical and/or chemical transformation of the zeolitic material crystallized in step (2) from the mixture provided in step (1). The crystallized material can for example be subject to any sequence of isolation and/or washing procedures, wherein the zeolitic material obtained from crystallization in step (2) is preferably subject to at least one isolation and at least one washing procedure.

Isolation of the crystallized product can be achieved by any conceivable means. Preferably, isolation of the crystallized product can be achieved by means of filtration, ultrafiltration, diafiltration, centrifugation and/or decantation methods, wherein filtration methods can involve suction and/or pressure filtration steps. According to preferred embodiments of the method of the present application according to which the zeolitic material is obtainable and/or obtained, it is preferred that the reaction mixture is first adjusted to a pH comprised in the range of from 5 to 9, preferably of 6 to 8, more preferably of 6.5 to 7.8, and more preferably of 7 to 7.6 prior to isolation. Within the meaning of the present invention, pH values preferably refer to those values as determined via a standard glass electrode.

With respect to one or more optional washing procedures, any conceivable solvent can be used. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol, such as water and methanol or water and ethanol or water and propanol or water and methanol and ethanol or water and methanol and propanol or water and ethanol and propanol or water and methanol and ethanol and propanol. Water or a mixture of water and at least one alcohol, preferably water and ethanol, is preferred, distilled water being very particularly preferred as the only washing agent.

Preferably, the separated zeolitic material is washed until the pH of the washing agent, preferably the washwater, is in the range of from 6 to 8, preferably from 6.5 to 7.5.

Furthermore, the method of the present application according to which the zeolitic material is obtainable and/or obtained can optionally comprise one or more drying steps. In general, any conceivable means of drying can be used. In general the drying procedure may include any suitable stationary or continuous drying procedures such as the use of a band dryer. Dry-milling and spinflash procedures may also be mentioned as possible alternatives. Drying procedures preferably include heating and/or applying vacuum to the zeolitic material. In envisaged embodiments of the method of the present application according to which the zeolitic material is obtainable and/or obtained, one or more drying steps may also involve spray drying, such as may be achieved by spray granulation of the zeolitic material.

In embodiments of the method of the present application according to which the zeolitic material is obtainable and/or obtained which comprise at least one drying step, the drying temperatures are preferably in the range of from 25° C. to 150° C., more preferably of from 60 to 140° C., more preferably of from 70 to 130° C. and even more preferably in the range of from 75 to 125° C. The durations of drying are preferably in the range of from 2 to 24 h, more preferably in the range of 2.5 to 10 hours, more preferably of from 3 to 7 h, and even more preferably of from 3.5 to 5 h.

According to alternative embodiments of the method of the present application according to which the zeolitic material is obtainable and/or obtained which are preferred, the zeolitic material crystallized in step (2) is directly subject to at least one step of drying, preferably to spray drying and or spray granulation, without isolating, washing, or drying of the zeolitic material beforehand. Directly subjecting the mixture obtained from step (2) of the method of the present application according to which the zeolitic material is obtainable and/or obtained to a spray drying or spray granulation stage has the advantage that isolation and drying is performed in a single stage. Consequently, according to this embodiment of the present invention, an even more preferred method of the present application according to which the zeolitic material is obtainable and/or obtained is provided wherein not only removal of organotemplate compounds is avoided, but also the number of post-synthesis workup steps is minimized, as a result of which the zeolitic material can be obtained from a highly simplified method.

In general, the optional washing and/or isolation and/or ion-exchange procedures comprised in the method of the present application according to which the zeolitic material is obtainable and/or obtained can be conducted in any conceivable order and repeated as often as desired.

In addition to one or more of the aforementioned work-up steps which may be conducted after step (2) and prior to step (3) of the method of the present application according to which the zeolitic material is obtainable and/or obtained, according to further preferred embodiments, in addition to the one or more optional drying steps or in place of said one or more drying steps, the optionally washed zeolitic material is subject to one or more steps of calcination. According to the present invention, said one or more steps of calcination are particularly preferred with respect to particular embodiments of the method of the present application according to which the zeolitic material is obtainable and/or obtained, wherein the mixture prepared in step (1) further comprises one or more organotemplates for removing said organotemplates after the synthesis of the zeolitic material having an MFI, MEL, and/or MWW-type framework structure. According to said preferred embodiments wherein one or more calcination steps are performed after step (2) and prior to step (3) of the inventive process, no particular restriction applies neither with respect to the repetition and in particular the number of repetitions of the calcination step which may be performed, nor with respect to the temperature employed in the calcination procedure nor with respect to the duration of the calcination procedure. According to the particular embodiments of the method of the present application according to which the zeolitic material is obtainable and/or obtained, wherein one or more organotemplates are further comprised in the mixture prepared in step (1), it is preferred that the conditions of the calcination and in particular the temperature and/or duration and/or number of repetitions of the calcination step is chosen such that the one or more organotemplates are substantially removed from the porous structure of the zeolitic material having an MFI, MEL, and/or MWW-type framework structure.

Within the meaning of the present invention, the term "substantially" and in particular the use of said term with respect to the amount of said one or more organotemplates which may at most remain in the porous structure of the zeolitic material after calcination thereof designates residual amounts of carbon and/or nitrogen originating from said one or more organotemplates which may at most remain in the porous structure of the zeolitic material. More specifically, a zeolitic material having been crystallized in step (2) of the method of the present application according to which the zeolitic material is obtainable and/or obtained in the presence of one or more organotemplates is substantially free thereof within the meaning of the present invention in cases where the carbon and/or nitrogen content thereof is of 1.0 wt.-% or less based on 100 wt.-% of $YO_2$ contained in the framework structure of the zeolitic material having an MFI, MEL, and/or MWW-type framework structure, and preferably an amount of 0.5 wt.-% or less, more preferably of 0.2 wt.-% or less, more preferably of 0.1 wt.-% or less, more preferably of 0.05 wt.-% or less, more preferably of 0.01 wt.-% or less, more preferably of 0.005 wt.-% or less, and more preferably of 0.001 wt.-% or less based on 100 wt.-% of $YO_2$ in the zeolitic material.

As regards the one or more calcination steps according to preferred embodiments of the method of the present application according to which the zeolitic material is obtainable and/or obtained, the temperature of the calcination procedure employed therein may range anywhere from 300 to 850° C., wherein preferably the calcination in step (2d) ranges from 350 to 700° C., and more preferably from 400 to 600° C. According to particularly preferred embodiments of the method of the present application according to which the zeolitic material is obtainable and/or obtained, the calcination in step (2d) is conducted at a temperature in the range of 450 to 550° C. As regards the duration of the one or more calcination steps according to step (2d) of the method of the present application according to which the zeolitic material is obtainable and/or obtained, there is again no particular restriction in this respect such that the calcination may be conducted for a duration ranging anywhere from 1 to 80 hours, wherein preferably the duration of the calcination according to any of the particular and preferred embodiments described in the present application ranges from 2 to 24 h during which the temperature of calcination is maintained, more preferably from 2.5 to 12 h, more preferably from 3 to 10 h, more preferably from 3.5 to 8 h, and more preferably from 4 to 7 h. According to particularly preferred embodiments of the method of the present application according to which the zeolitic material is obtainable and/or obtained further comprising a calcination procedure, the duration thereof ranges from 4.5 to 6 h, during which the chosen temperature of calcination is maintained.

As regards the number of times the calcination procedure in step (2d) may be performed, it is preferred that the calcination procedure is conducted one to three times in step (2d), wherein more preferably the calcination procedure is conducted once or twice, wherein according to particularly preferred embodiments the calcination procedure is performed once in step (2d) of the method of the present application according to which the zeolitic material is obtainable and/or obtained.

According to the present invention it is further preferred that the zeolitic material is subject to a hydrothermal treatment step (2e). In general, there is no particular restriction as to how the hydrothermal treatment is conducted, provided that the treatment leads to a change in the zeolitic materials physical and/or chemical properties, wherein it is particularly preferred that the hydrothermal treatment leads to a reduction in the zeolitic material's hydrophobicity.

Thus, in principle, the preferred hydrothermal treatment step may be conducted under any suitable conditions, and in particular any suitable pressure and temperature. According to the present invention it is however preferred that the hydrothermal treatment is conducted under autogenous pressure, which may for example be achieved by using an autoclave or any suitable pressure digestion vessel.

As regards the temperature at which the hydrothermal treatment in step (2e) is conducted, again, any suitable temperature may be employed, wherein it is preferred that the hydrothermal treatment in step (2e) is conducted under heating, and preferably at a temperature ranging from 80 to 250° C., more preferably from 100 to 220° C., more preferably from 120 to 200° C., more preferably from 140 to 190° C., and more preferably from 160 to 185° C. According to the present invention it is however particularly preferred that the hydrothermal treatment in step (2e) is conducted at a temperature comprised in the range of from 170 to 180° C.

With respect to the duration of the hydrothermal treatment step, and in particular the duration of heating according to any of the preferred and particularly embodiments of the inventive process, again no particular restriction applies provided that the duration is sufficient for leading to a change in the zeolitic material's physical and/or chemical properties and in particular to it's hydrophobicity under that chosen conditions, in particular with respect to the chosen temperature and pressure. Thus, by way of example, the duration of the hydrothermal treatment may range anywhere from 2 to 72 h, wherein preferably the treatment in step (2e) is conducted for a duration ranging from 4 to 48 h, more preferably from 8 to 36 h, and more preferably from 12 to 30 h. According to the present invention it is particularly preferred that the hydrothermal treatment in step (2e) is conducted for a period ranging from 18 to 24 h.

Concerning the effect of the hydrothermal treatment preferably conducted according to step (2e), there is no particular restriction as to the changes in physical and/or chemical properties of the zeolitic material which may be achieved, wherein it is particularly preferred that the conditions of hydrothermal treatment according to the preferred and particularly preferred embodiments of the inventive process in particular with respect to temperature, pressure, and duration lead to an increase in the zeolitic material's hydrophobicity. Thus, according to the present invention it is preferred that the zeolitic material obtained in step (2e) displays a decreased water uptake relative to the zeolitic material prior to the treatment in step (2e). Accordingly, as regards the specific water uptake of the zeolitic material obtained in step (2e), there is in principle no? restriction according to the aforementioned preferred embodiments of the present invention provided that the zeolitic material's hydrophobicity is increased, i.e. that the water uptake of the zoelitic material decreases as a result of the treatment in step (2e). Thus, in general, the water uptake of the zeolitic material obtained in step (2e) is not particularly restricted, such that the water uptake of the material obtained in said step may by way of example display a water uptake of 10.0 wt.-% or less, wherein preferably the hydrothermally treated zeolitic material obtained in step (2e) preferably displays a water uptake of 7.4 wt.-% or less, more preferably of 6.2 wt.-% or less, more preferably of 6.0 wt.-% or less, more preferably of 5.0 wt.-% or less, more preferably of 4.5 wt.-% or less, more preferably of 4.2 wt.-% or less, more preferably of 3 wt.-% or less, and more preferably of 2.2 wt.-% or less. According to the present invention it is particularly preferred that the hydrothermally treated zeolitic material obtained in step (2e) displays a water uptake of 2 wt.-% or less, and more preferably of 1.5 wt.-% or less.

Therefore, in general, it is preferred according to the inventive process that the catalyst provided in step (ii) and more preferably the zeolitic material having an MFI, MEL, and/or MWW-type framework structure comprising $YO_2$ and $X_2O_3$, wherein Y is a tetravalent element, and X is a trivalent element comprised in the catalyst displays a water uptake of 10.0 wt.-% or less, more preferably of 7.4 wt.-% or less, more preferably of 6.2 wt.-% or less, more preferably of 6.0 wt.-% or less, more preferably of 5.0 wt.-% or less, more preferably of 4.5 wt.-% or less, more preferably of 4.2 wt.-% or less, more preferably of 3 wt.-% or less, and more preferably of 2.2 wt.-% or less, more preferably of 2 wt.-% or less, and more preferably of 1.5 wt.-% or less. In particular, this applies irrespective of whether the material is obtained according to any of the preferred and particularly preferred embodiments of the inventive process including a step (2e) of subjecting the zeolitic material to a hydrothermal treatment. Preferably, however, the catalyst and in particular the zeolitic material comprised in the catalyst employed in step (ii) displaying any one of the preferred and particularly preferred water uptake is obtained according to any one of the particular and preferred embodiments of the inventive process including a step (2e) of subjecting the zeolitic material having an MFI, MEL, and/or MWW-type framework structure comprising $YO_2$ and $X_2O_3$, wherein Y is a tetravalent element, and X is a trivalent element to a hydrothermal treatment.

Within the meaning of the present invention, the water uptake of a material and in particular of a zeolitic material as defined in any of the particular and preferred embodiments of the present invention expressed in wt.-% preferably refers to the water uptake of a material at 85 wt.-% relative humidity (RH) expressed in increase in weight compared to the dry sample, i.e. the weight of the sample measured at 0% RH. According to the present invention it is preferred that the weight of the sample measured at 0% RH refers to the sample from which residual moisture has been removed by heating the sample to 100° C. (heating ramp of 5° C./min) and holding it for 6 h under a nitrogen flow. According to the present invention it is particularly preferred that the water uptake of a material as defined for any of the particular and preferred embodiments of the inventive process refers to the water uptake of a material and in particular of a zeolitic material at 85% RH as obtained according to the procedure for the measurement of the water adsorption/desorption isotherms as described in the experimental section of the present application.

Therefore, embodiments of the method of the present application according to which the zeolitic material is obtainable and/or obtained are preferred, wherein after step (2) the process further comprises (2a) adjusting the pH of the product mixture obtained in (2) to a pH in the range of 5 to 9, preferably of 6 to 8, more preferably of 6.5 to 7.8, and more preferably of 7 to 7.6;

and/or (2b) isolating the zeolitic material from the product mixture obtained in (2), preferably by filtration, ultrafiltration, diafiltration, centrifugation and/or decantation methods;

and/or (2c) washing the zeolitic material;

and/or (2d) drying and/or calcining the zeolitic material;

and/or (2e) subjecting the zeolitic material to a hydrothermal treatment.

As regards the form in which the zeolitic material may be employed in the inventive process, no particular restriction applies, provided that at least one oxygenate may be converted to at least one olefin. Thus, by way of examples, the zeolitic material may be employed in the form of a powder, a spray powder or a spray granulate obtained from above-described separation techniques, e.g. decantation, filtration, centrifugation, or spraying.

According to preferred embodiments of the inventive process, however, the zeolitic material obtainable and/or obtained according to a method as defined in the present application is further processed to give one or more moldings.

Thus, according to particularly preferred embodiments of the inventive process for the conversion of oxygenates to olefins, the catalyst comprises a molding comprising a zeolitic material obtainable and or obtained according to the method as defined in the present application, and in particular according to any of the particular and preferred embodiments thereof.

In general, the molding preferably comprised in the catalyst of the inventive process may comprise any conceivable compounds in addition to the zeolitic material obtainable and/or obtained according to a method as defined in the present application, provided that at least one oxygenate may be converted to at least one olefin.

In the context of the present invention, it is preferred to use at least one suitable binder material in the production of the molding. In this preferred embodiment, it is more preferred to prepare a mixture of the zeolitic material obtainable and/or obtained according to a method as defined in the present application and the at least one binder material.

Accordingly, the present invention also describes a process for the production of the molding preferably comprised in the catalyst of the inventive process, said molding containing the zeolitic material obtainable and/or obtained according to a method as defined in the present application as described above, said process for the production of the molding comprising the step of
  (A) preparation of a mixture containing a zeolitic material obtainable and/or obtained according to a method as defined in the present application, and at least one binder material.

Suitable binder materials are in general all compounds which impart adhesion and/or cohesion between the particles of the zeolitic material which are to be bound, which adhesion and cohesion are over and above the physisorption which may be present without a binder material. Examples of such binder materials are metal oxides, such as $SiO_2$, $Al_2O_3$, $TiO_2$, $ZrO_2$ or MgO or clays or mixtures of two or more of these compounds.

As $Al_2O_3$ binder materials, clay minerals and naturally occurring or synthetic aluminas, for example alpha-, beta-, gamma-, delta-, eta-, kappa-, chi- or theta-alumina and the inorganic or organometallic precursor compounds thereof, for example gibbsite, bayerite, boehmite, pseudoboehmite or trialkoxyaluminates, for example aluminum triisopropylate, are in particular suitable. Further preferred binder materials are amphiphilic compounds having a polar and a nonpolar moiety, and graphite. Further binder materials are, for example, clays, such as montmorillonites, kaolins, bentonites, halloysites, dickites, nacrites or anaxites.

These binder materials may be used as such. It is also possible in the context of the present invention to use compounds from which the binder is formed in at least one further step in the production of the moldings. Examples of such binder material precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate.

In the context of the present invention, binder materials which either completely or partly comprise $SiO_2$ or are a precursor of $SiO_2$ from which $SiO_2$ is formed in at least one further step in the production of the moldings are very particularly preferred. In this context, both colloidal silica and wet process silica and dry process silica can be used. These are very particularly preferably amorphous silica, wherein the size of the silica particles is in the range of from 5 to 100 nm and the surface area of the silica particles is in the range of from 50 to 500 $m^2/g$.

Colloidal silica, preferably as an alkaline and/or ammoniacal solution, more preferably as an ammoniacal solution, is commercially available, inter alia, as Ludox®, Syton®, Nalco® or Snowtex®. Wet process silica is commercially available, inter alia, as Hi-Sil®, Ultrasil®, Vulcasil®, Santocel®, Valron-Estersil®, Tokusil® or Nipsil®. Dry process silica is commercially available, inter alia, as Aerosil®, Reolosil®, Cab-O-Sil®, Fransil® or ArcSilica®. Inter alia, an ammoniacal solution of colloidal silica is preferred in the context of the present invention.

The present invention also describes a process for the production of the molding preferably comprised in the catalyst of the inventive process, wherein the binder material employed according to (A) is $SiO_2$-containing or -forming binder material. Accordingly, the present invention also describes a process for the production of the molding, wherein the binder material is a colloidal silica.

The binder materials are preferably used in an amount which leads to the finally resulting moldings, whose binder content is up to 80, more preferably from 5 to 80, more preferably from 10 to 70, more preferably from 10 to 60, more preferably from 15 to 50, more preferably from 15 to 45, particularly preferably from 15 to 40, % by weight, based in each case on the total weight of the finally resulting molding.

The mixture of binder material or precursor for a binder material and the zeolitic material can be mixed with at least one further compound for further processing and for forming a plastic mass. Inter alia, pore formers are preferred here. Pore formers which may be used in the process according to the present invention are all compounds which, with regard to the prepared molding, provide a certain pore size, a certain pore size distribution and/or a certain pore volume.

Preferably used pore formers in the process according to the present invention are polymers which are dispersible, suspendable or emulsifiable in water or in aqueous solvent mixtures. Preferred polymers here are polymeric vinyl compounds, for example polyalkylene oxides, such as polyethylene oxides, polystyrene, polyacrylates, polymethacrylates, polyolefins, polyamides and polyesters, carbohydrates, such as cellulose or cellulose derivatives, for example methylcellulose, or sugar or natural fibers. Further suitable pore formers are, for example, pulp or graphite.

If pore formers are used in the preparation of the mixture according to (A), the polymer content of the mixture according to (A) is preferably in the range of from 5 to 90, more preferably from 15 to 75, particularly preferably from 25 to 55, % by weight, based in each case on the amount of zeolitic material in the mixture according to (A). If it is desirable for the pore size distribution to be achieved, a mixture of two or more pore formers may also be used.

In a particularly preferred embodiment of the process for the production of the molding preferably comprised in the catalyst of the inventive process, as described below, the pore formers are removed in a step (E) by calcination to give the porous molding. According to a preferred embodiment of the process according to the present invention, moldings which have pores in the range of at least 0.6, preferably from 0.6 to 0.8, particularly preferably from more than 0.6 to 0.8, ml/g, as determined according to DIN 66134, are obtained.

The specific surface area of the molding preferably comprised in the catalyst of the inventive process, as determined according to DIN 66131, is in general at least 250 $m^2/g$, preferably at least 290 $m^2/g$, particularly preferably at least 300 $m^2/g$. For example, the specific surface area may be from 250 to 400 $m^2/g$ or from 290 to 450 $m^2/g$ or from 300 to 500 $m^2/g$.

Accordingly, the molding preferably comprised in the catalyst of the inventive process preferably displays a specific surface area of at least 250 m²/g, containing pores having a pore volume of at least 0.6 ml/g.

In the preparation of the mixture according to (A), at least one pasting agent is added in a likewise preferred embodiment of the process according to the present invention. Pasting agents which may be used are all compounds suitable for this purpose. These are preferably organic, in particular hydrophilic, polymers, for example cellulose, cellulose derivatives, such as methylcellulose, starch, such as potato starch, wallpaper paste, polyacrylates, polymethacrylates, polyvinyl alcohol, polyvinylpyrrolidone, polyisobutene, polyethyleneglycol or polytetrahydrofuran. In particular, compounds which also act as pore formers can accordingly be used as pasting agents. In a particularly preferred embodiment of the process according to the present invention, as described below, these pasting agents are removed in a step (E) by calcination to give the porous molding.

According to a further embodiment of the present invention, at least one acidic additive is introduced during the preparation of the mixture according to (A). Organic acidic compounds can be removed by calcination in the preferred step (E), as described below, are very particularly preferred. Carboxylic acids, for example formic acid, oxalic acid and/or citric acid, are particularly preferred. It is also possible to use two or more of these acidic compounds.

The order of addition of the components of the mixture according to (A) which contains the zeolitic material obtainable and/or obtained according to a method as defined in the present application is not critical. It is possible both first to add the at least one binder material, subsequently the at least one pore former, the at least one acidic compound and finally the at least one pasting agent and it is possible to interchange the sequence with regard to the at least one binder material, the at least one pore former, the at least one acidic compound and the at least one pasting agent.

After the addition of the binder material to the zeolite-containing solid, to which optionally at least one of the compounds described above had already been added, the mixture according to (A) is as a rule homogenized for from 10 to 180 min. Inter alia, kneaders, edge mills or extruders are particularly preferably used for the homogenization. The mixture is preferably kneaded. On an industrial scale, treatment in an edge mill is preferred for homogenization.

Accordingly, the present invention also describes a process for the production of the molding preferably comprised in the catalyst of the inventive process, said process for the production of the molding comprising the steps
 (A) preparation of a mixture containing a zeolitic material obtainable and/or obtained according to a method as defined in the present application, and at least one binder material;
 (B) kneading of the mixture.

In the homogenization, as a rule temperatures of from about 10° C. to the boiling point of the pasting agent and atmospheric or slightly superatmospheric pressure are employed. Subsequently at least one of the compounds described above can be optionally added. The mixture thus obtained is homogenized, preferably kneaded, until an extrudable plastic mass has formed. The homogenized mixture is molded according to a more preferred embodiment of the present invention.

In the context of the present invention, preferred shaping methods are those in which the molding is effected by extrusion in conventional extruders, for example to give extrudates having a diameter of, preferably, from 1 to 10 mm, particularly preferably from 2 to 5 mm. Such extrusion apparatuses are described, for example, in Ullmann's Enzyklopädie der Technischen Chemie, 4th Edition, Vol. 2, page 295 et seq., 1972. In addition to the use of an extruder, a ram extruder may likewise preferably be used for the molding.

In principle, however, all known and/or suitable kneading and molding apparatuses and methods can be used for the shaping. Examples of these include:
 (a) bricketting, i.e. mechanical pressing with or without addition of additional binder material;
 (b) pelleting, i.e. compacting by circular and/or rotational movements;
 (c) sintering, i.e. the material to be molded is subjected to a thermal treatment.

For example, the shaping can be selected from the following group, wherein the combination of at least two of these methods is explicitly included: bricketting by means of a ram press, roll press, ring-roll press, bricketting without binder; pelleting, melting, spinning techniques, deposition, foaming, spray-drying; combustion in a shaft furnace, convection furnace, travelling grate, rotary kiln, edge mill.

The compacting may take place at ambient pressure or at superatmospheric pressure, for example at from 1 to several hundred bar. Furthermore, the compacting may take place at ambient temperature or at a temperature higher than the ambient temperature, for example at from 20 to 300° C. If drying and/or combustion are part of the shaping step, temperatures of up to 1,500° C. are conceivable. Finally, the compacting may take place in the ambient atmosphere or in a controlled atmosphere. Controlled atmospheres are, for example, inert gas atmospheres or reducing and/or oxidizing atmospheres.

Accordingly, the present invention also describes a process for the production of the molding preferably comprised in the catalyst of the inventive process, said process for the production of the molding comprising the steps
 (A) preparation of a mixture containing a zeolitic material obtainable and/or obtained according to a method as defined in the present application, and at least one binder material;
 (B) kneading of the mixture;
 (C) molding of the kneaded mixture to give at least one molding.

The shape of the moldings produced according to the process can be chosen as desired. In particular, inter alia spheres, oval shapes, cylinders or tablets are possible.

In the context of the present invention, the molding is particularly preferably carried out by extrusion of the kneaded mixture obtained according to (B), more preferably substantially cylindrical extrudates having a diameter in the range of from 1 to 20 mm, preferably from 1 to 10 mm, more preferably from 2 to 10 mm, and particularly preferably from 2 to 5 mm, being obtained as extrudates.

In the context of the present invention, step (C) is preferably followed by at least one drying step. This at least one drying step is effected at temperatures in general in the range of from 80 to 160° C., preferably from 90 to 145° C., particularly preferably from 100 to 130° C., wherein the duration of drying generally is 6 hours or more, for example in the range of from 6 to 24 hours. However, depending on the moisture content of the material to be dried, shorter drying times, for example about 1, 2, 3, 4 or 5 hours, are also possible.

Before and/or after the drying step, the preferably obtained extrudate can, for example, be milled. Preferably, granules or chips having a particle diameter of from 0.1 to 5 mm, in particular from 0.5 to 2 mm, are obtained.

Accordingly, the present invention also describes a process for the production of the molding preferably comprised in the catalyst of the inventive process, said process for the production of the molding comprising the steps (A) preparation of a mixture containing a zeolitic material obtainable and/or obtained according to a method as defined in the present application, and at least one binder material;
(B) kneading of the mixture;
(C) molding of the kneaded mixture to give at least one molding;
(D) drying of the at least one molding.

In the context of the present invention, step (D) is preferably followed by at least one calcination step. The calcination is carried out at a temperature in general in the range of from 350 to 750° C., preferably from 450 to 600° C.

The calcination can be effected under any suitable gas atmosphere, air and/or lean air being preferred. Furthermore, the calcination is preferably carried out in a muffle furnace, a rotary kiln and/or a belt calcination furnace, wherein the duration of calcination generally is 1 hour or more, for example in the range of from 1 to 24 or from 3 to 12 h. Accordingly, it is possible in the process according to the present invention, for example, to calcine the moldings once, twice or more often for in each case at least one hour, for example in each case in the range of from 3 to 12 h, wherein the temperatures during the calcination step can remain the same or can be changed continuously or discontinuously. If calcination is effected twice or more often, the calcination temperatures in the individual steps may be different or identical.

Accordingly, the present invention also relates to a process for the production of the molding preferably comprised in the catalyst of the inventive process, said process for the production of the molding comprising the steps (A) preparation of a mixture containing a zeolitic material obtainable and/or obtained according to a method as defined in the present application, and at least one binder material;
(B) kneading of the mixture;
(C) molding of the kneaded mixture to give at least one molding;
(D) drying of the at least one molding;
(E) calcination of the at least one dried molding.

After the calcination step, the calcined material can, for example, be comminuted. Preferably, granules or chips having a particle diameter of from 0.1 to 5 mm, in particular from 0.5 to 2 mm, are obtained.

Before and/or after the drying and/or before and/or after the calcination, the at least one molding can be treated with a concentrated or dilute Broenstedt acid or with a mixture of two or more Broenstedt acids. Suitable acids are, for example, hydrochloric acid, sulfuric acid, phosphoric acid, nitric acid or carboxylic acids, dicarboxylic acids or oligo- or polycarboxylic acids, such as nitrilotriacetic acid, sulfosalicylic acid or ethylenediaminotetraacetic acid.

Preferably, this at least one treatment with at least one Broenstedt acid is followed by at least one drying step and/or at least one calcination step, which in each case is carried out under the conditions described above.

According to a further preferred embodiment of the process according to the present invention, the catalyst extrudates can be subjected to a steam treatment for better hardening, after which once again preferably drying is effected at least once and/or calcination is effected at least once. For example, after at least one drying step and at least one subsequent calcination step, the calcined molding is subjected to steam treatment and then once again dried at least once and/or calcined at least once.

The moldings obtained according to the process have hardnesses which are in general in the range of from 2 to 40 N, preferably in the range of from 5 to 40 N, particularly preferably from 10 to 40 N.

In the present invention, the hardness described above was determined on an apparatus from Zwick, type BZ2.5/TS1S with a preliminary force of 0.5 N, a feed velocity under the preliminary force of 10 mm/min and a subsequent test velocity of 1.6 mm/min. The apparatus had a fixed turntable and a freely movable punch with built-in blade of 0.3 mm thickness. The movable punch with the blade was connected to a load cell for force pick-up and, during the measurement, moved toward the fixed turntable on which the catalyst molding to be investigated was present. The test apparatus was controlled by means of a computer which registered and evaluated the measured results. The value obtained is the mean value of the measurements for 10 catalyst moldings in each case. The catalyst moldings had a cylindrical geometry, wherein their average length corresponds to about twice to three times the diameter, and were loaded with the blade of 0.3 mm thickness with increasing force until the molding had been cut through. The blade was applied to the molding perpendicularly to the longitudinal axis of the molding. The force required for this purpose is the cutting hardness (unit N).

Figure 1A:
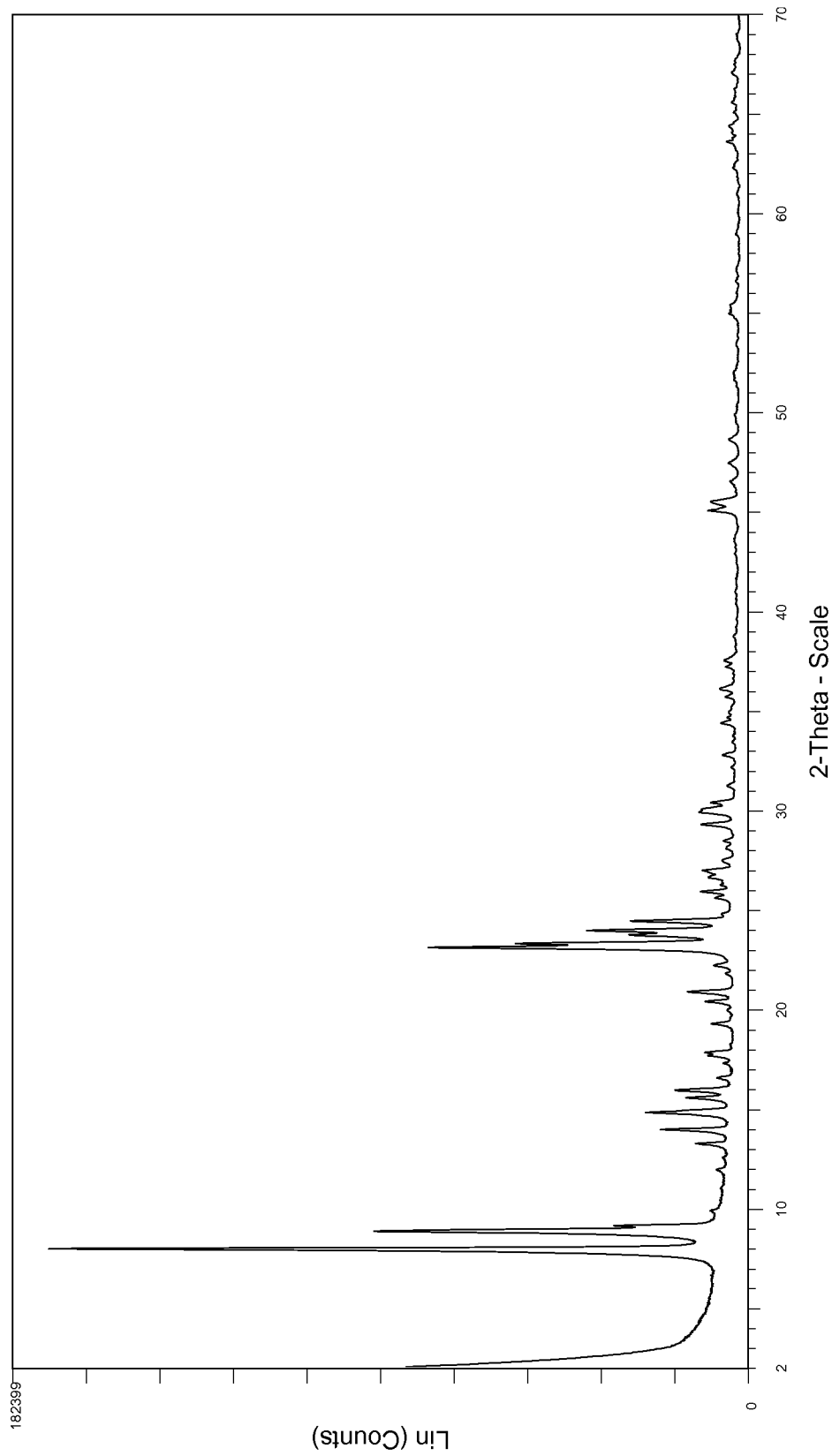
FIGS. 1A, 2A, 3A, 4A, 5A, 6A, and 7A show the X-ray diffraction patterns (measured using Cu K alpha-1 radiation) of the crystalline material obtained according to Reference Examples 1-7, respectively. In the respective figures, the angle 2 theta in ° is shown along the abscissa and the intensity in counts is plotted along the ordinate.

The present invention includes the following embodiments, wherein these include the specific combinations of embodiments as indicated by the respective interdependencies defined therein:

1. Process for the conversion of oxygenates to olefins comprising
   (i) providing a gas stream comprising one or more oxygenates; and
   (ii) contacting the gas stream with a catalyst;
   wherein the catalyst comprises a zeolitic material having an MFI, MEL, and/or MWW-type framework structure comprising $YO_2$ and $X_2O_3$, wherein Y is a tetravalent element, and X is a trivalent element,
   said zeolitic material being obtainable and/or obtained according to a method comprising (1) preparing a mixture comprising one or more sources for $YO_2$, one or more sources for $X_2O_3$, and one or more solvents; and (2) crystallizing the mixture obtained in step (1) to obtain a zeolitic material having an MFI, MEL and/or MWW-type framework structure;

wherein the mixture crystallized in step (2) contains 3 wt.-% or less of the one or more elements M based on 100 wt.-% of $YO_2$, wherein M stands for sodium.

2. The process of embodiment 1, wherein the mixture crystallized in step (2) contains 1 wt.-% or less of the one or more elements M based on 100 wt-% of $YO_2$.

3. The process of embodiment 1 or 2, wherein the gas stream provided in step (i) contains one or more oxygenates selected from the group consisting of aliphatic alcohols, ethers, carbonyl compounds, and mixtures of two or more thereof.

4. The process of any of embodiments 1 to 3, wherein the gas stream provided in step (i) contains from 30 to 100 vol.-% of oxygenates based on the total volume of the gas stream.

5. The process of any of embodiments 1 to 4, wherein the gas stream provided in step (i) contains 60 vol.-% or less of water based on the total volume of the gas stream.

6. The process of any of embodiments 1 to 5, wherein contacting of the gas stream with the catalyst in step (ii) is performed at a temperature in the range of 200 to 700° C.

7. The process of any of embodiments 1 to 6, wherein contacting of the gas stream with the catalyst in step (ii) is performed at a pressure in the range of 0.1 to 10 bar.

8. The process of embodiment 7, wherein the process is at least in part performed in a continuous mode.

9. The process of any of embodiments 1 to 8, wherein the weight hourly space velocity (WHSV) of the gas stream in step (ii) ranges from 0.5 to 50 $h^{-1}$.

10. The process of any of embodiments 1 to 9, wherein 95% by weight or more of the primary particles of the zeolitic material have a diameter of less than or equal to 1 μm.

11. The process of any of embodiments 1 to 10, wherein 90% or more of the primary particles of the zeolitic material are spherical.

12. The process of any of embodiments 1 to 11, wherein 95% by weight or more of the primary particles of the zeolitic material have a diameter of from 5 to 800 nm.

13. The process of any of embodiments 1 to 12, wherein M stands for sodium and potassium.

14. The process of any of embodiments 1 to 13, wherein the zeolitic material displays a $YO_2:X_2O_3$ atomic ratio of from 10 to 1,500.

15. The process of any of embodiments 1 to 14, wherein the tetravalent element Y is selected from the group consisting of Si, Sn, Ti, Zr, Ge, and mixtures of two or more thereof.

16. The process of any of embodiments 1 to 15, wherein the trivalent element X is selected from the group consisting of Al, B, In, Ga, and mixtures of two or more thereof.

17. The process of any of embodiments 1 to 16, wherein the zeolitic material comprises ZSM-5.

18. The process of any of embodiments 1 to 17, wherein the BET surface area of the zeolitic material determined according to DIN 66131 ranges from 200 to 900 $m^2/g$.

19. The process of any of embodiments 1 to 18, wherein the $YO_2:X_2O_3$ molar ratio of the mixture prepared in step (1) ranges from 10 to 1,500.

20. The process of any of embodiments 1 to 19, wherein the one or more solvents provided in step (1) comprise one or more polar solvents.

21. The process of any of embodiments 1 to 20, wherein the mixture in step (1) further comprises one or more organotemplates.

22. The process of embodiment 21, wherein the one or more organotemplates comprises one or more tetraalkylammonium compounds selected from the group consisting of tetraethylammonium compounds, triethylpropylammonium compounds, diethyldipropylammonium compounds, ethyltripropylammonium compounds, tetrapropylammonium compounds, and mixtures of two or more thereof.

23. The process of embodiment 21 or 22, wherein the one or more organotemplates comprises one or more alkenyltrialkylammonium compounds selected from the group consisting of N—$(C_2$-$C_5)$alkenyl-tri-$(C_1$-$C_5)$alkylammonium compounds.

24. The process of any of embodiments 21 to 23, wherein the molar ratio of the total amount of the one or more organotemplates of the mixture obtained in step (1) to $YO_2$ ranges from 1:(0.1-30).

25. The process of any of embodiments 1 to 24, wherein the mixture according to step (1) further comprises one or more sources for $OH^-$.

26. The process of embodiment 25, wherein the $OH^-:YO_2$ molar ratio of the mixture obtained in step (1) ranges from 0.01 to 5.

27. The process of any of embodiments 1 to 26, wherein the crystallization in step (2) involves heating of the mixture.

28. The process of any of embodiments 1 to 27, wherein the crystallization in step (2) is conducted under solvothermal conditions.

29. The process of embodiment 27 or 28, wherein the crystallization in step (2) involves heating of the mixture for at least 3 h.

30. The process of any of embodiments 1 to 29, wherein after step (2) the process further comprises (2a) adjusting the pH of the product mixture obtained in (2) to a pH in the range of 5 to 9;

and/or (2b) isolating the zeolitic material from the product mixture obtained in (2);

and/or (2c) washing the zeolitic material;

and/or (2d) drying and/or calcining the zeolitic material;

and/or (2e) subjecting the zeolitic material to a hydrothermal treatment.

31. The process of any of embodiments 1 to 30, wherein the calcination in step (2d) is conducted at a temperature in the range of 300 to 850° C.

32. The process of embodiment 30 or 31, wherein the hydrothermal treatment in step (2e) is conducted under autogenous pressure.

33. The process of any of embodiments 30 to 32, wherein the hydrothermal treatment in step (2e) is conducted using an aqueous solvent system, wherein preferably the aqueous solvent system consists of water, preferably of distilled water.

34. The process of any of embodiments 30 to 33, wherein the hydrothermal treatment in step (2e) is conducted under heating, and preferably at a temperature ranging from 80 to 250° C., more preferably from 100 to 220° C., more preferably from 120 to 200° C., more preferably from 140 to 190° C., more preferably from 160 to 185° C., and more preferably from 170 to 180° C.

35. The process of any of embodiments 30 to 34, wherein the hydrothermal treatment in step (2e) is conducted for a duration ranging from 2 to 72 h, preferably from 4 to 48 h, more preferably from 8 to 36 h, more preferably from 12 to 30 h, and more preferably from 18 to 24 h.

36. The process of any of embodiments 30 to 35, wherein the hydrothermally treated zeolitic material obtained in step (2e) displays a water uptake of 10.0 wt.-% or less, preferably of 7.4 wt.-% or less, more preferably of 6.2 wt.-% or less, more preferably of 6.0 wt.-% or less, more preferably of 5.0 wt.-% or less, more preferably of 4.5 wt.-% or less, more preferably of 4.2 wt.-% or less, more preferably of 3 wt.-% or less, more preferably of 2.2 wt.-% or less, more preferably of 2 wt.-% or less, and more preferably of 1.5 wt.-% or less.

EXAMPLES

Determination of the Crystallinity

The crystallinity of the zeolitic materials in the present examples was determined by XRD analysis, wherein the crystallinity of a given material is expressed relative to a reference zeolitic material wherein the reflecting surfaces of the two zeolitic materials are compared. The reference zeolitic materials were commercial H-ZSM-5 at an $SiO_2/Al_2O_3$ ratio of 100 or 250. The determination of the crystallinities was performed on a D8 Advance series 2 diffractometer from Bruker AXS. The diffractometer was configured with an opening of the divergence aperture of 0.1° and a Lynxeye detector. The samples as well as the reference zeolitic material were measured in the range from 21° to 25° (2 Theta). After baseline correction, the reflecting surfaces were determined by making use of the evaluation software EVA (from Bruker AXS). The ratios of the reflecting surfaces are given as percentage values.

FT-IR Measurements

The IR measurements in the present examples were performed on a Nicolet 6700 spectrometer. The zeolitic materials were pressed into a self-supporting pellet without the use of any additives. The pellet was introduced into a high vacuum cell placed into the IR instrument. Prior to the measurement the sample was pretreated in high vacuum (10-5 mbar) for 3 h at 300° C. The spectra were collected after cooling the cell to 50° C. The spectra were recorded in the range of 4000 $cm^{-1}$ to 1400 $cm^{-1}$ at a resolution of 2 $cm^{-1}$. The obtained spectra were represented by a plot having on the x axis the wavenumber ($cm^{-1}$) and on the y axis the absorbance (arbitrary units). For the quantitative determination of the band heights and the ratio between the bands a baseline correction was carried out. Changes in the 3000 to 3900 $cm^{-1}$ region were analyzed and for comparing multiple samples, the band at 1880±5 $cm^{-1}$ was taken as reference.

Water Adsorption/Desorption Measurements

Water adsorption/desorption isotherms in the present examples were performed on a VTI SA instrument from TA Instruments following a step-isotherm program. The experiment consisted of a run or a series of runs performed on a sample material that has been placed on the microbalance pan inside of the instrument. Before the measurement was started, the residual moisture of the sample was removed by heating the sample to 100° C. (heating ramp of 5° C./min) and holding it for 6 h under a nitrogen flow. After the drying program, the temperature in the cell was decreased to 25° C. and kept constant during the measurement. The microbalance was calibrated, and the weight of the dried sample was balanced (maximum mass deviation 0.01 wt.-%). Water uptake of a sample was measured as the increase in weight compared to the dry sample. First, an adsorption curve was measured by increasing the relative humidity (RH) (expressed as weight-% water in the atmosphere inside of the cell) to which the sample was exposed and measuring the water uptake by the sample as equilibrium. The RH was increased with a step of 10% from 5% to 85% and at each step the system controlled the RH and monitored the weight of the sample until reaching the equilibrium conditions after the sample and recording the weight uptake. The total adsorbed water of the sample was taken after the sample was exposed to the 85 weight-% RH. During the desorption measurement, the RH was decreased from 85 weight-% to 5 weight-% with a step of 10% and the change in the weight of the sample (water uptake) was monitored and recorded.

Determination of the Crush Strength of the Moldings

The crush strength in the present examples is to be understood as determined via a crush strength test machine Z2.5/TS1S, supplier Zwick GmbH & Co., D.89070 Ulm, Germany. As to the fundamentals of this machine and its operation, reference is made to the respective instructions handbook "Register 1: Betriebsanleitung/Sicherheitshandbuch für die Material-Prüfmaschine Z2.5/TS1S", version 1.5, December 2001 by Zwick GmbH & Co. Technische Dokumentation, August-Nagel-Strasse 11, D-89079 Ulm, Germany. With said machine, a given (final) strand as prepared in Reference Examples 8 to 14, having a diameter of 2.5 mm, is subjected to an increasing force via a plunger having a diameter of 3 mm until the strand is crushed. The force at which the strand crushes is referred to as the crushing strength of the strand. The machine is equipped with a fixed horizontal table on which the strand is positioned. A plunger which is freely movable in vertical direction actuates the strand against the fixed bed table. The apparatus was operated with a preliminary force of 0.5 N, a shear rate under preliminary force of 10 mm/min and a subsequent testing rate of 1.6 mm/min. The vertically movable plunger was connected to a load cell for force pick-up and, during the measurement, moved toward the fixed turntable on which the molding (strand) to be investigated is positioned, thus actuating the strand against the table. The plunger was applied to the strands perpendicularly to their longitudinal axis. Controlling the experiment was carried out by means of a computer which registered and evaluated the results of the measurements. The values obtained are the mean value of the measurements for 25 strands in each case.

Reference Example 1

Synthesis of ZSM-5 Zeolite at an $SiO_2:Al_2O_3$ Molar Ratio of 100

Tetraethylorthosilicate (757 g) was stirred in a four-necked flask. Water (470 g) and tetrapropylammonium hydroxide (40 wt % in water, 366 g) were added. The mixture was stirred for 60 minutes during which the temperature rose to 60° C. This was due to the hydrolysis of tetraethyllorthosilicate resulting in the formation of ethanol. The ethanol was removed via distillation until a sump temperature of 95° C. was reached. Thereby 817 g of ethanol were removed from the mixture. The mixture was then allowed to cool to 40° C. while stirring, 817 g of water were added and the resulting gel was filled into an autoclave. A solution of aluminum sulfate octadecahydrate (24.2 g) and water (40 g) were added to the autoclave. The autoclave was closed and heated to 170° C.

After stirring the gel at 170° C. for 48 h the autoclave was cooled to ambient temperature and the mixture was removed. It was treated with nitric acid (10 wt % in water, 173 g) until a pH value of 7.3 was reached. The resulting suspension was filtered. The filter cake was washed three times with water (1,000 mL each), dried (4 h, 120° C.) and calcined (5 h, 500° C.), to afford 217 g of ZSM-5. The size of the primary particles as determined by SEM was in the range of from 100 to 200 nm.

Elemental Analysis:

|    |         |
|----|---------|
| Si | 43.5 wt.-% |
| Al | 0.87 wt.-% |
| Na | <100 ppm |
| K  | <100 ppm |

Thus, according to the chemical analysis, the calcined material displayed an $SiO_2:Al_2O_3$ molar ratio of 96.

FIG. 1A shows the XRD of the crystalline product obtained from the synthesis of Example 1, displaying the line pattern typical for the MFI framework structure. The crystallinity as determined according to Reference Example 1 was 98%.

Figure 1B:
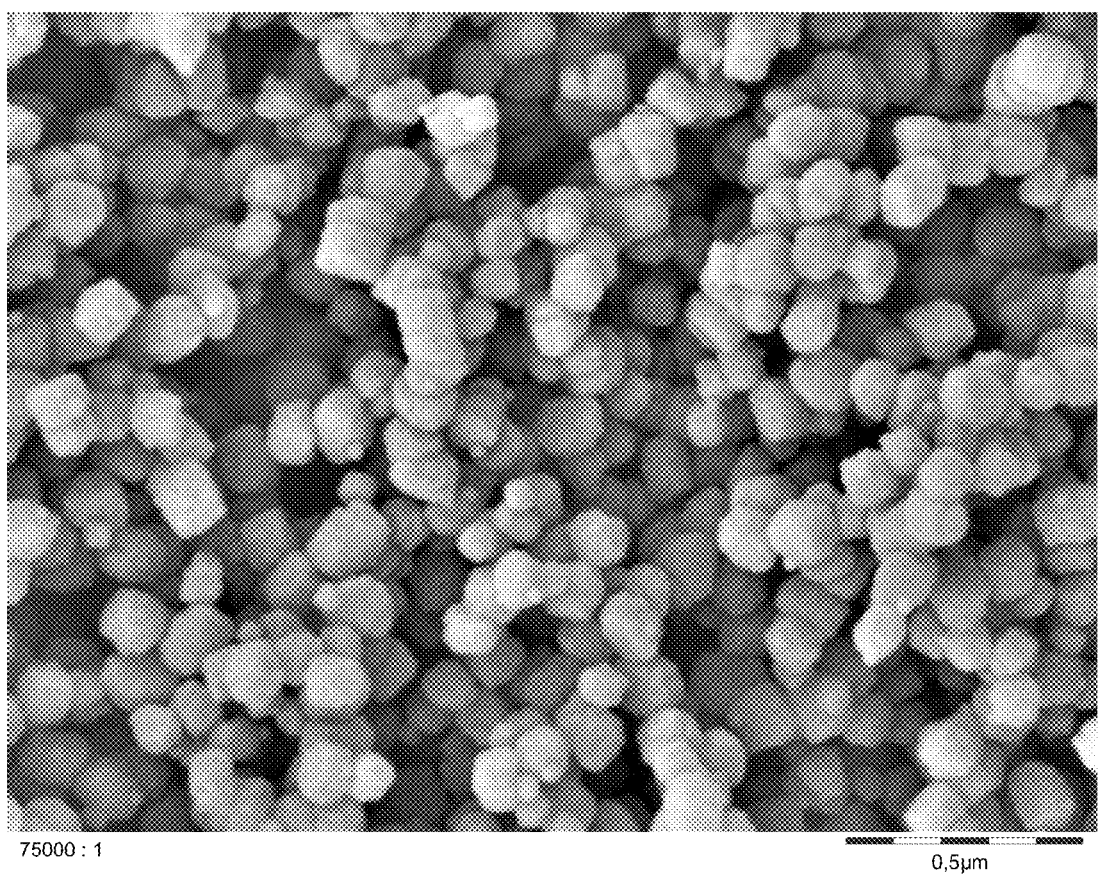
FIGS. 1B, 2B, 3B, 4B, and 6B respectively show a scanning electron micrograph (SEM) of the ZSM-5 powder which was obtained according to Reference Examples 1-4, and 6, respectively, using a magnification of 75,000:1 as indicated at the lower left hand corner of the image. At the lower right hand corner of the SEM micrographs, a unit length corresponding to 0.5 µm in the image is indicated as a checkered bar with 5 subunits of 0.1 µm, respectively.

FIG. 1B shows the electron micrograph of the product as obtained from SEM at a magnification of $75 \times 10^4$. As may be taken from the micrograph, practically only spherical primary particles are observed even at this high degree of magnification, wherein the size of the primary particles was determined to lie in the range of from 100-170 nm.

The material displayed a BET surface area of 426 m$^2$/g. The pore volume was determined to be 0.17 cm$^3$/g at $p/p_0$=0.302 and the median pore width to be 0.58 nm as respectively determined via Argon adsorption using the Horvath-Kawazoe method. The total intrusion volume determined according to Hg porosimetry according to DIN 66133 was 1.24 ml/g (milliliter/gram), the respective total pore area 40.5 m$^2$/g.

Temperature programmed desorption of ammonia afforded values of 0.43 mmol/g when conducted at 152° C. and of 0.24 mmol/g when conducted at 378° C.

The material had a water uptake of 6.3 wt. % at a relative humidity of 85%.

Figure 1C:
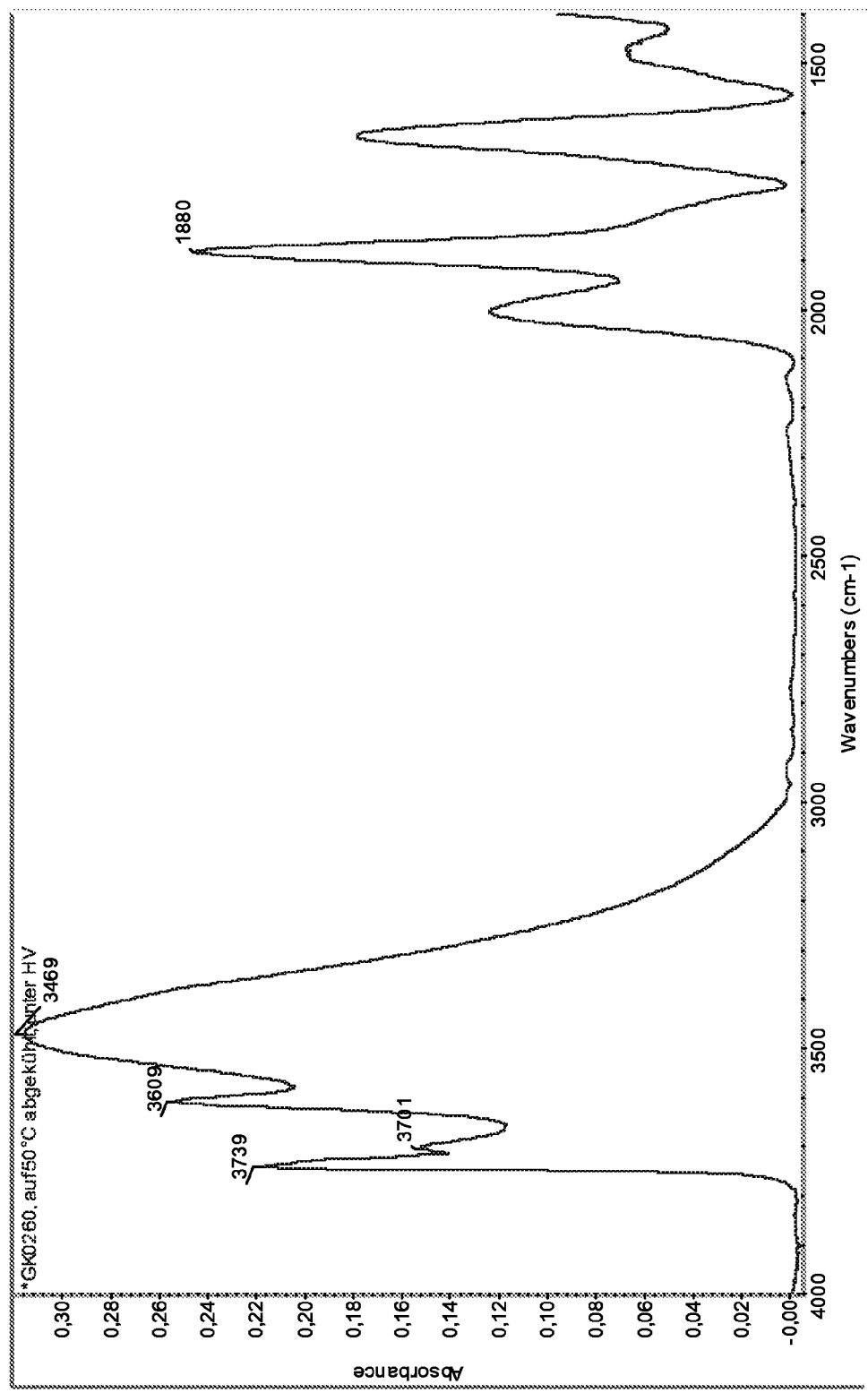
FIGS. 1C, 2C, 4C, 5B, 6C, and 7B respectively show the IR spectra of the crystalline material obtained according to Reference Examples 1-7. In the respective figures, the wavenumbers in $cm^{-1}$ is plotted along the abscissa and the absorbance in arbitrary units is plotted along the ordinate.

FIG. 1C shows the IR-OH bands of the sample obtained according to Reference Example 1. The band regions along with the band heights are as follows:

| Region of OH band | Assignment | Band Height |
|---|---|---|
| 3739 cm$^{-1}$ | external acid sites, i.e. "surface silanol" | 0.22 |
| 3701 cm$^{-1}$ | Lewis acid sites from extraframework Al | 0.16 |
| 3609 cm$^{-1}$ | Lewis acid sites from extraframework Al | 0.26 |
| 3469 cm$^{-1}$ | internal Broensted acid sites, i.e. "silanol nests" | 0.32 |

Accordingly, the IR-band ratio of the absorbance intensity for the silanol nests to the surface silanol amounts to 1.45.

Reference Example 2

Synthesis of ZSM-5 Zeolite at an $SiO_2:Al_2O_3$ Molar Ratio of 250

Tetraethylorthosilicate (757 kg) was stirred in a vessel. Water (470 kg) and tetrapropylammonium hydroxide (40 wt % in water, 333 kg) were added. The mixture was stirred for 60 minutes during which the temperature rose to 60° C. This was due to the hydrolysis of tetraethylorthosilicate resulting in the formation of ethanol. The ethanol was removed via distillation until a sump temperature of 95° C. was reached. Thereby 832 kg of ethanol were removed from the mixture. 832 kg of water and a solution of aluminum sulfate octadecahydrate (9.4 kg) and water (20 kg) were added to the vessel. The vessel was closed and heated to 150° C.

After stirring the gel at 150° C. for 24 h the autoclave was cooled to ambient temperature and the mixture was removed. It was treated with nitric acid (10 wt % in water) until a pH value of 7.1 was reached. The resulting suspension was filtered. The filter cake was washed with water and dried (120° C.). The dry powder was ground and subsequently calcined (5 h, 500° C.).

Elemental Analysis:

|    |         |
|----|---------|
| Si | 43.5 wt.-% |
| Al | 0.36 wt.-% |
| Na | <100 ppm |
| K  | <100 ppm |

Thus, according to the chemical analysis, the calcined material displayed an $SiO_2:Al_2O_3$ molar ratio of 233.

Figure 2A:
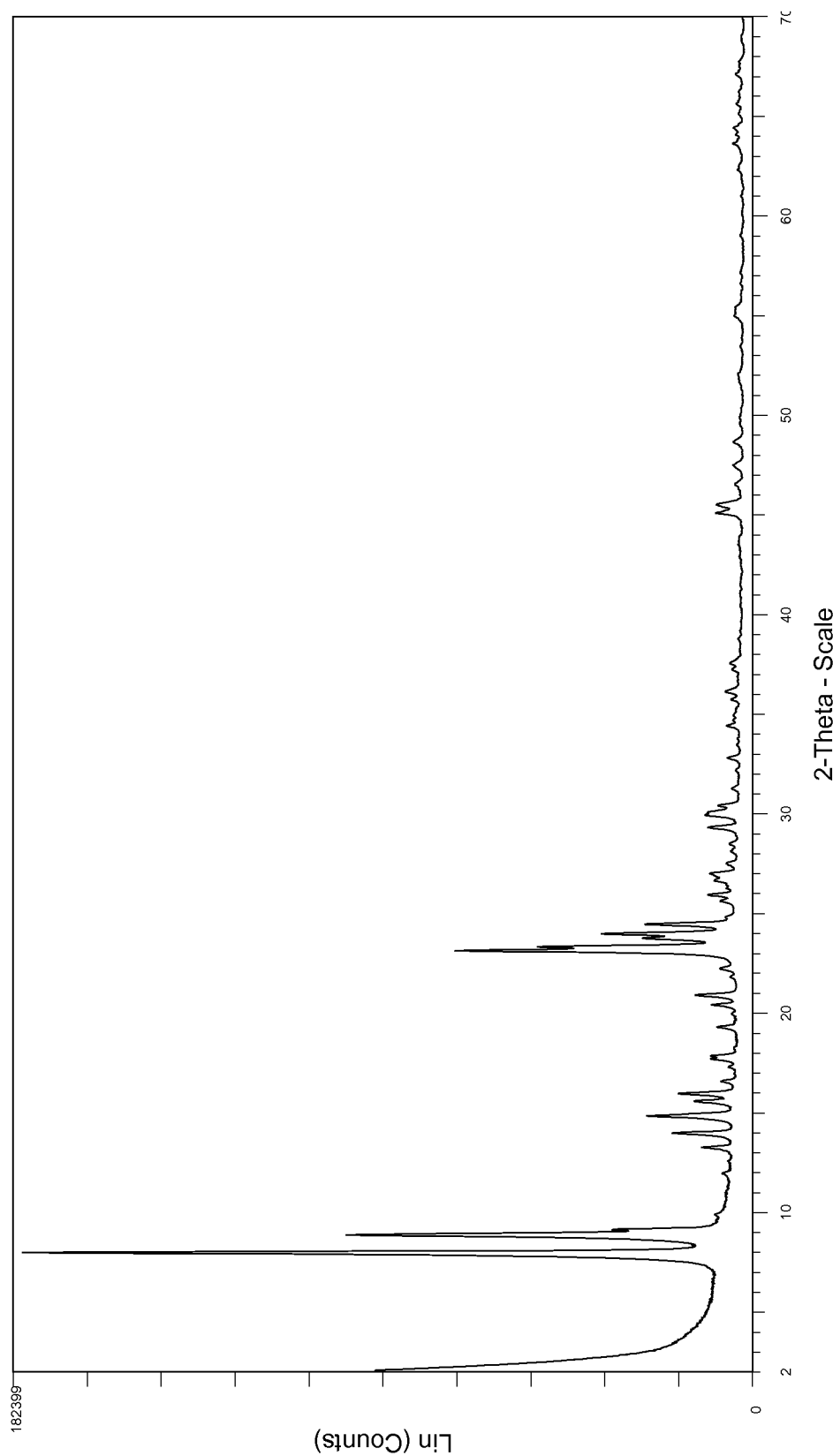
Figure 2B:
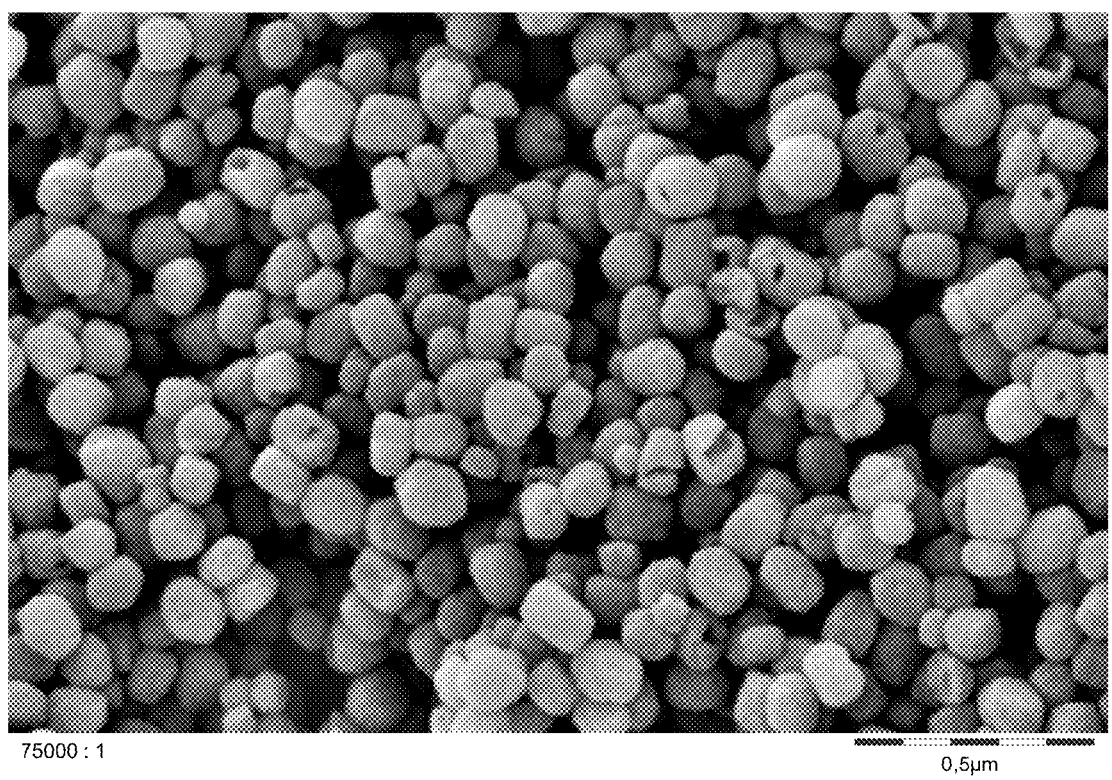

FIG. 2A shows the XRD of the crystalline product obtained from the synthesis of Reference Example 2, displaying the line pattern typical for the MFI framework structure. The crystallinity as determined according to Reference Example 1 was 96%. FIG. 2B shows the electron micrograph of the product as obtained from SEM at a magnification of $75 \times 10^4$. As may be taken from the micrograph, practically only spherical primary particles are observed even at this high degree of magnification, wherein the size of the primary particles was determined to lie in the range of from 50-150 nm.

The material displayed a BET surface area of 441 m$^2$/g. The pore volume was determined to be 0.18 cm$^3$/g at $p/p_0$=0.301 and the median pore width to be 0.54 nm as respectively determined via Argon adsorption using the Horvath-Kawazoe method. The total intrusion volume determined according to Hg porosimetry according to DIN 66133 was 1.45 ml/g (milliliter/gram), the respective total pore area 71.3 m$^2$/g.

Temperature programmed desorption of ammonia (NH$_3$-TPD) afforded values of 0.24 mmol/g when conducted at 107° C. and of 0.12 mmol/g when conducted at 343° C.

The material had a water uptake of 7.1 wt. % at a relative humidity of 85%.

Figure 2C:
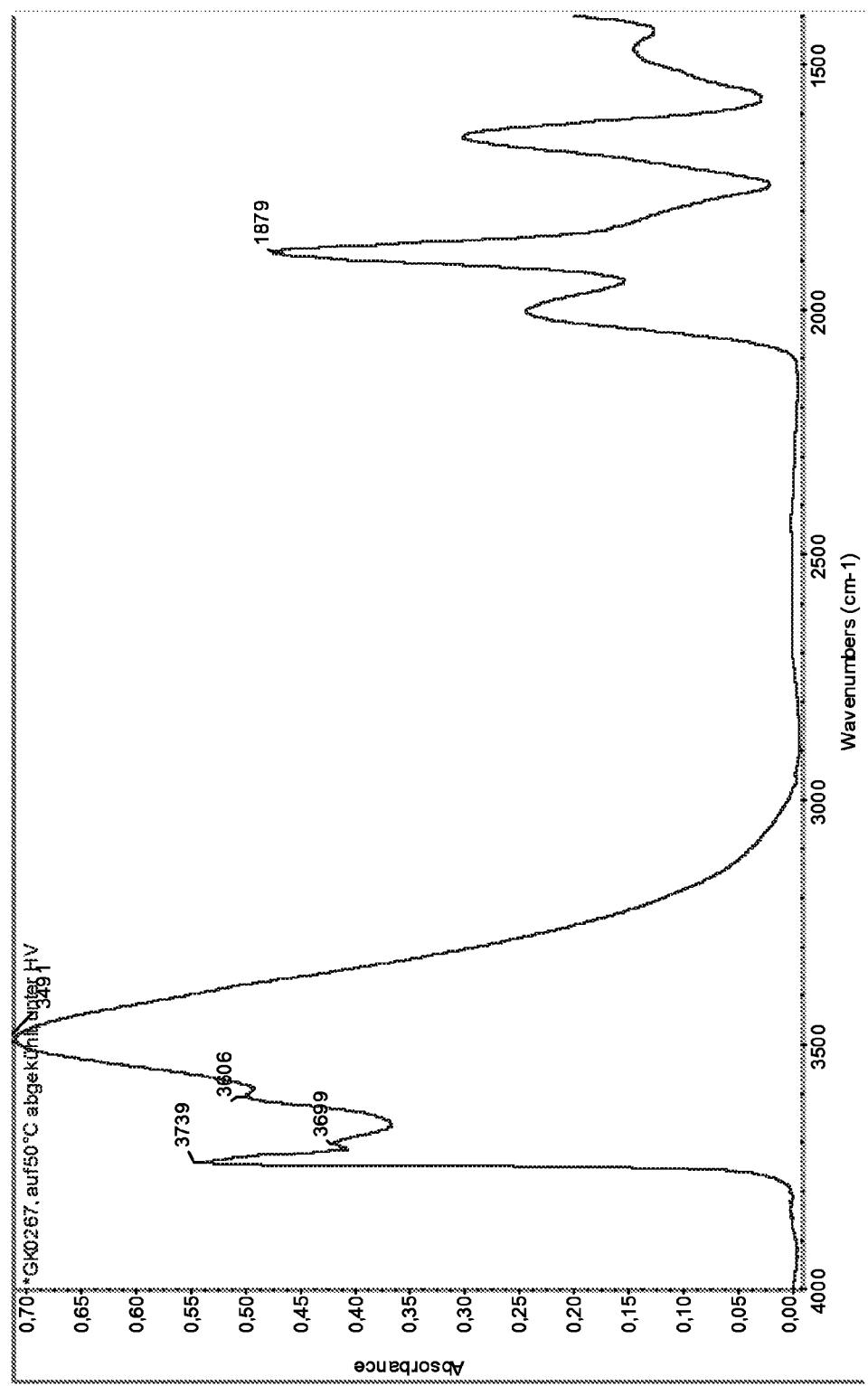

FIG. 2C shows the IR-OH bands of the sample obtained according to Reference Example 2. The band regions along with the band heights are as follows:

| Region of OH band | Assignment | Band Height |
|---|---|---|
| 3739 cm$^{-1}$ | external acid sites, i.e. "surface silanol" | 0.55 |
| 3699 cm$^{-1}$ | Lewis acid sites from extraframework Al | 0.43 |
| 3606 cm$^{-1}$ | Lewis acid sites from extraframework Al | 0.52 |
| 3491 cm$^{-1}$ | internal Broensted acid sites, i.e. "silanol nests" | 0.75 |

Accordingly, the IR-band ratio of the absorbance intensity for the silanol nests to the surface silanol amounts to 1.36.

Reference Example 3

Synthesis of ZSM-5 Zeolite at an $SiO_2:Al_2O_3$ Molar Ratio of 320

Tetraethylorthosilicate (757 g) was stirred in a four-necked flask. Water (470 g) and tetrapropylammonium hydroxide (40 wt % in water, 333 g) were added. The mixture was stirred for 60 minutes during which the temperature rose to 60° C. This was due to the hydrolysis of tetraethyllorthosilicate resulting in the formation of ethanol. The ethanol was removed via distillation until a sump temperature of 95° C. was reached. Thereby 805 g of ethanol were removed from the mixture. The mixture was then allowed to cool to 40° C. while stirring, 805 g of water were added and the resulting gel was filled into an autoclave. A solution of aluminum sulfate octadecahydrate (7.6 g) and water (25 g) were added to the autoclave. The autoclave was closed and heated to 170° C.

After stirring the gel at 170° C. for 24 h the autoclave was cooled to ambient temperature and the mixture was removed. It was treated with nitric acid (10 wt % in water, 203 g) until a pH value of 7.6 was reached. The resulting suspension was filtered. The filter cake was washed three times with water (1000 mL each), dried (4 h, 120° C.) and calcined (5 h, 500° C.), thus affording 222 g of calcined zeolite ZSM-5.

Elemental Analysis:

| Si | 44 wt.-% |
|----|----------|
| Al | 0.26 wt.-% |
| Na | <100 ppm |
| K  | <100 ppm |

Thus, according to the chemical analysis, the calcined material displayed an $SiO_2:Al_2O_3$ molar ratio of 325.

Figure 3A:
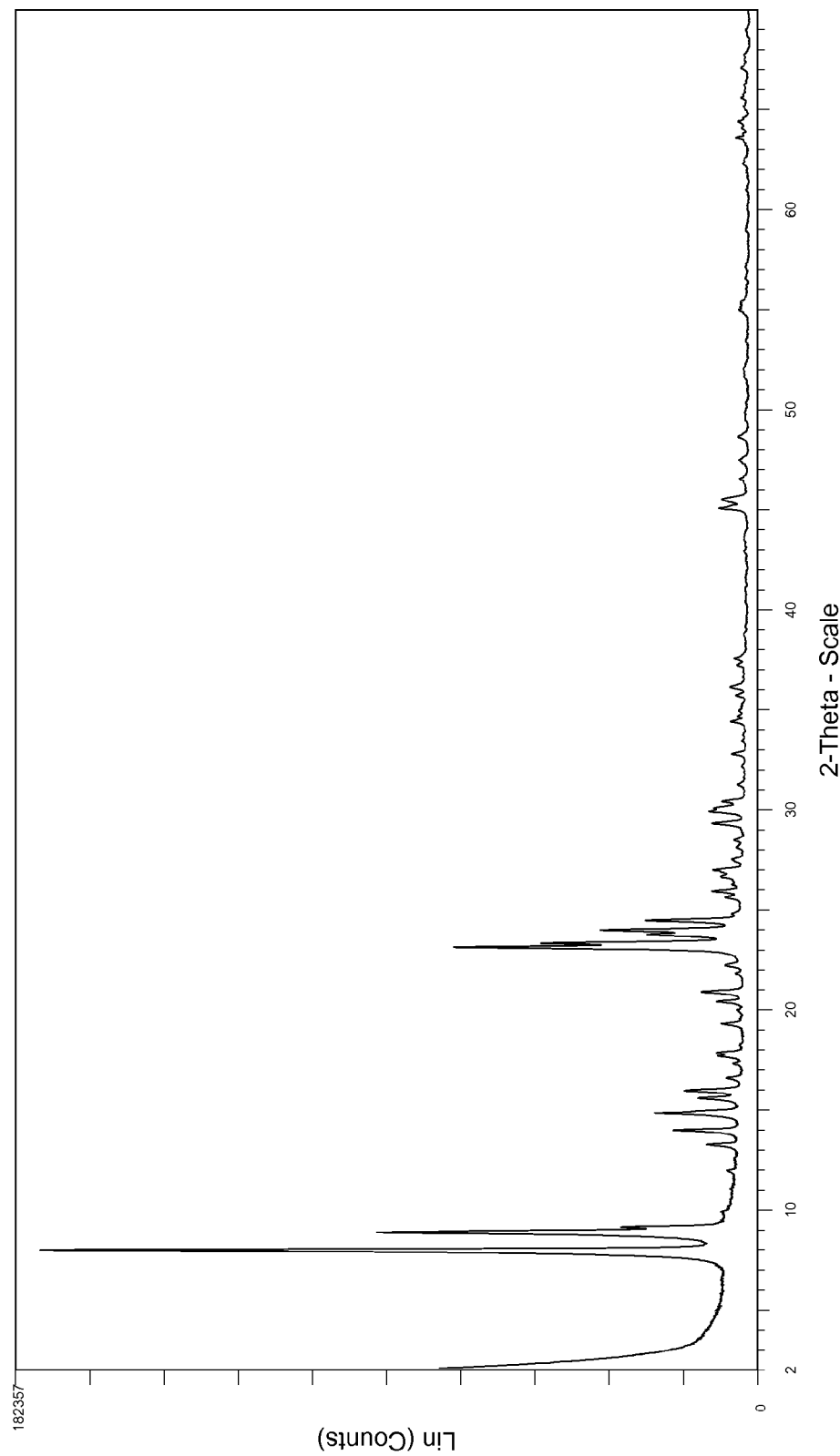
Figure 3B:
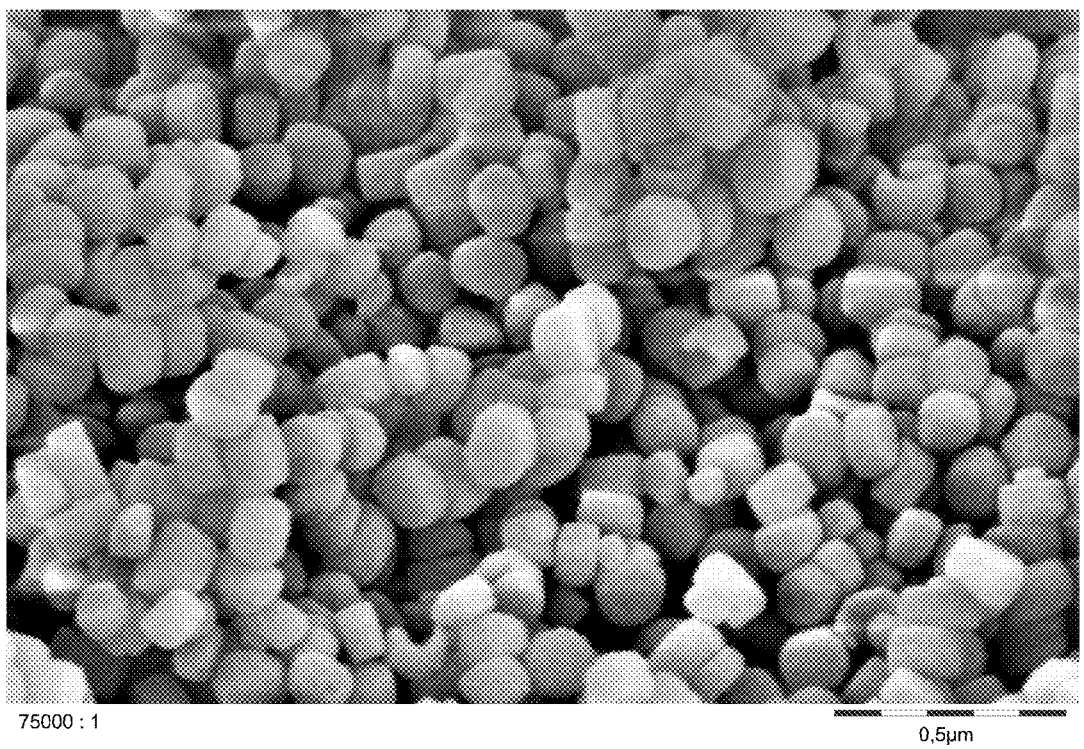

FIG. 3A shows the XRD of the crystalline product obtained from the synthesis of Example 1, displaying the line pattern typical for the MFI framework structure. FIG. 3B shows the electron micrograph of the product as obtained from SEM at a magnification of 75×10$^4$. As may be taken from the micrograph, practically only spherical primary particles are observed even at this high degree of magnification, wherein the size of the primary particles was determined to lie in the range of from 100-200 nm.

The material displayed a BET surface area of 442 m$^2$/g. The pore volume was determined to be 0.18 cm$^3$/g at $p/p_0$=0.301 and the median pore width to be 0.58 nm as respectively determined via Argon adsorption using the Horvath-Kawazoe method. Temperature programmed desorption of ammonia ($NH_3$-TPD) afforded values of 0.19 mmol/g when conducted at 108° C. and of 0.067 mmol/g when conducted at 340° C.

Reference Example 4

Water-Treatment of ZSM-5 Zeolite at an $SiO_2:Al_2O_3$ Molar Ratio of 100

Starting from the calcined powder obtained according to Reference Example 1, a post-treatment stage was performed as follows:

100 g of the calcined zeolitic powder obtained according to Reference Example 1 were suspended in 2000 g of deionized water. The mixture was filled in a vessel and the vessel was closed (pressure-tight). Then, the mixture was heated to a temperature of 145° C. within 1.5 h and kept at this temperature under autogenous pressure (about 4 bar) for 8 h. The water-treated powder was subjected to filtration and washed with deionized water. The obtained filter cake was dried at 120° C. for 4 h. Subsequently, the dried material was heated under air to a temperature of 500° C. within 4 h and kept at this temperature for 5 h. The yield thereafter was 85 g.

The thus obtained water-treated zeolitic powder had a Si content of 45 wt. %, an Al content of 0.87 wt. % which correspond to an $SiO_2:Al_2O_3$ molar ratio of 99.

Figure 4A:
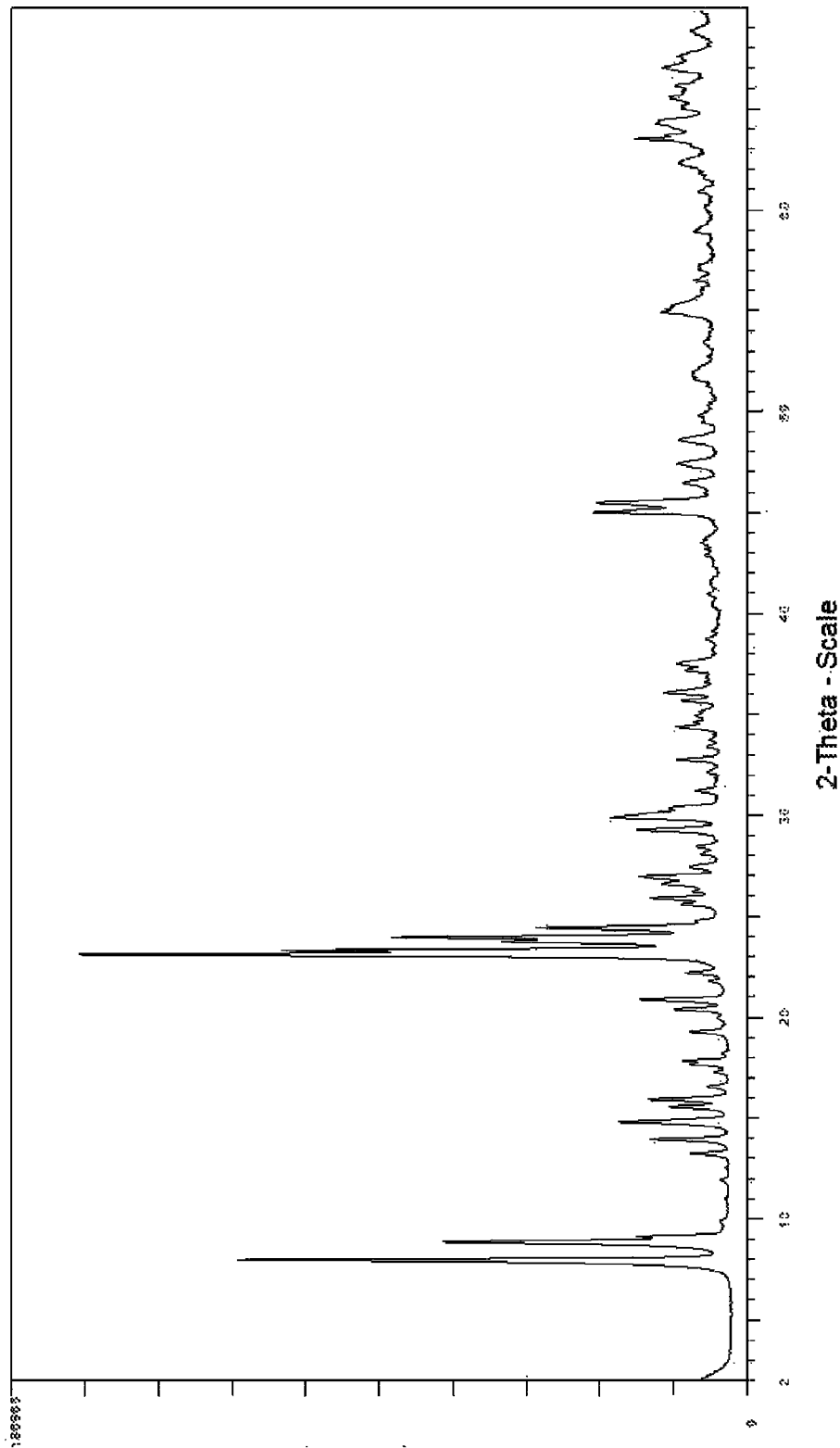

The degree of crystallization determined via XRD was 101-114%. The XRD of the material is shown in FIG. 4A. Thus, the inventive water treatment caused an increase from a value of 98% (cf. Reference Example 1) to a value of 101-114%.

Figure 4B:
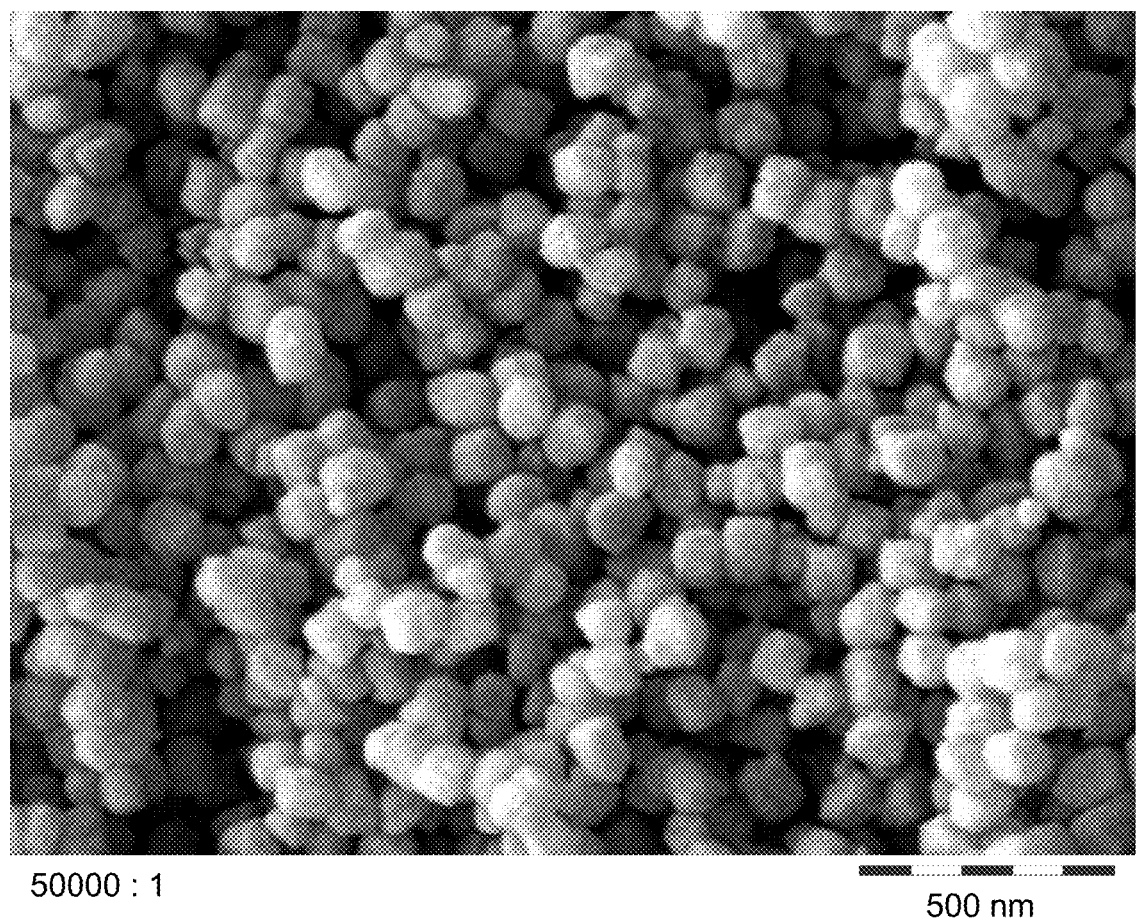

FIG. 4B shows the electron micrograph of the product as obtained from SEM at a magnification of 50×10$^4$. As may be taken from the micrograph, practically only spherical primary particles are observed even at this high degree of magnification, wherein the size of the primary particles was determined to lie in the range of from 70-150 nm.

The powder had a multipoint BET specific area determined via nitrogen adsorption at 77 K according to DIN 66133 of 427 m$^2$/g. The pore volume was determined to be 0.17 cm$^3$/g at $p/p_0$=0.281 and the median pore width to be 0.51 nm as respectively determined via Argon adsorption using the Horvath-Kawazoe method. The total intrusion volume determined according to Hg porosimetry according to DIN 66133 was 1.11 ml/g (milliliter/gram), the respective total pore area 40.7 m$^2$/g.

The total amount of adsorbed water as determined was 3.8-4.1 wt. % (compared to 6.3 wt. % of the starting material as described in Reference Example 1). Therefore, it is clearly shown that the inventive water treatment increases the hydrophobicity of the powder.

Figure 4C:
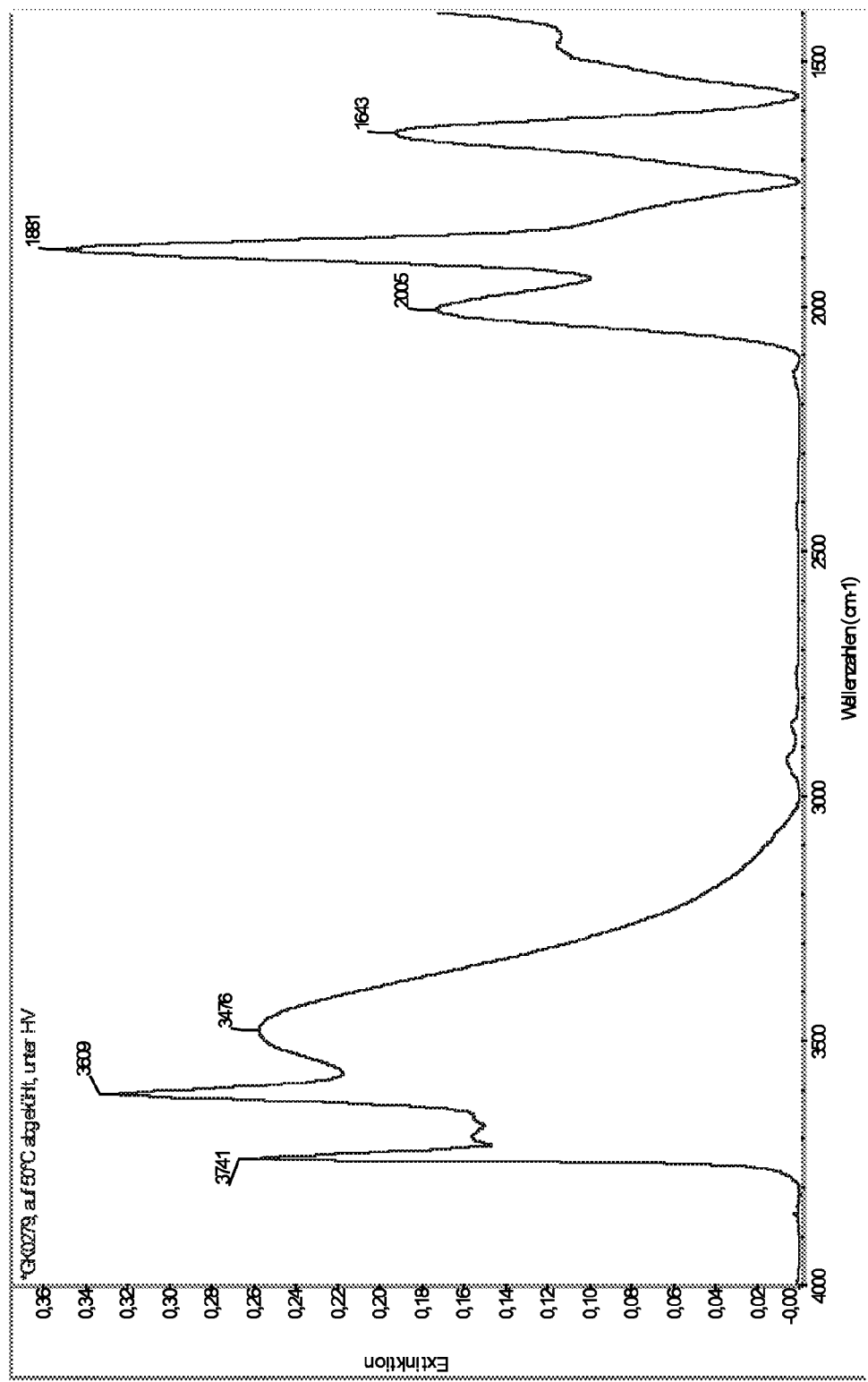

The IR spectrum of the powder obtained according to Reference Example 4 is shown in FIG. 4C. The band regions of the powder according to Reference Example 4 along with the band heights are as follows:

| Region of OH band | Assignment | Band Height |
|---|---|---|
| 3741 cm$^{-1}$ | external acid sites, i.e. "surface silanol" | 0.26 |
| ~3700 cm$^{-1}$ | Lewis acid sites from extraframework Al | value too low to be measured |
| 3609 cm$^{-1}$ | Lewis acid sites from extraframework Al | 0.32 |
| 3476 cm$^{-1}$ | internal Broensted acid sites, i.e. "silanol nests" | 0.26 |

Accordingly, the IR-band ratio of the absorbance intensity for the silanol nests to the surface silanol amounts to 1.00.

Reference Example 5

Water-Treatment of ZSM-5 Zeolite at an $SiO_2:Al_2O_3$ Molar Ratio of 100 According to Procedure in US2007/0135637A1

Starting from the calcined powder obtained according to Reference Example 1, a post-treatment stage was performed as follows:

132 g of the calcined zeolitic powder obtained according to Reference Example 1 were suspended in 1300 g of deionized water. The mixture was filled in a vessel and the vessel was closed (pressure-tight). Then, the mixture was heated to a temperature of 175° C. and kept at this temperature under autogenous pressure for 24 h. The water-treated powder was subjected to filtration and washed once with 500 mL deionized water. The obtained filter cake was dried at 120° C. for 16 h. Subsequently, the dried material was heated under air to a temperature of 500° C. and kept at this temperature for 5 h. The yield thereafter was 125 g.

The thus obtained water-treated zeolitic powder had a Si content of 45 wt. %, an Al content of 0.90 wt. % which correspond to an $SiO_2:Al_2O_3$ molar ratio of 96.

Figure 5A:
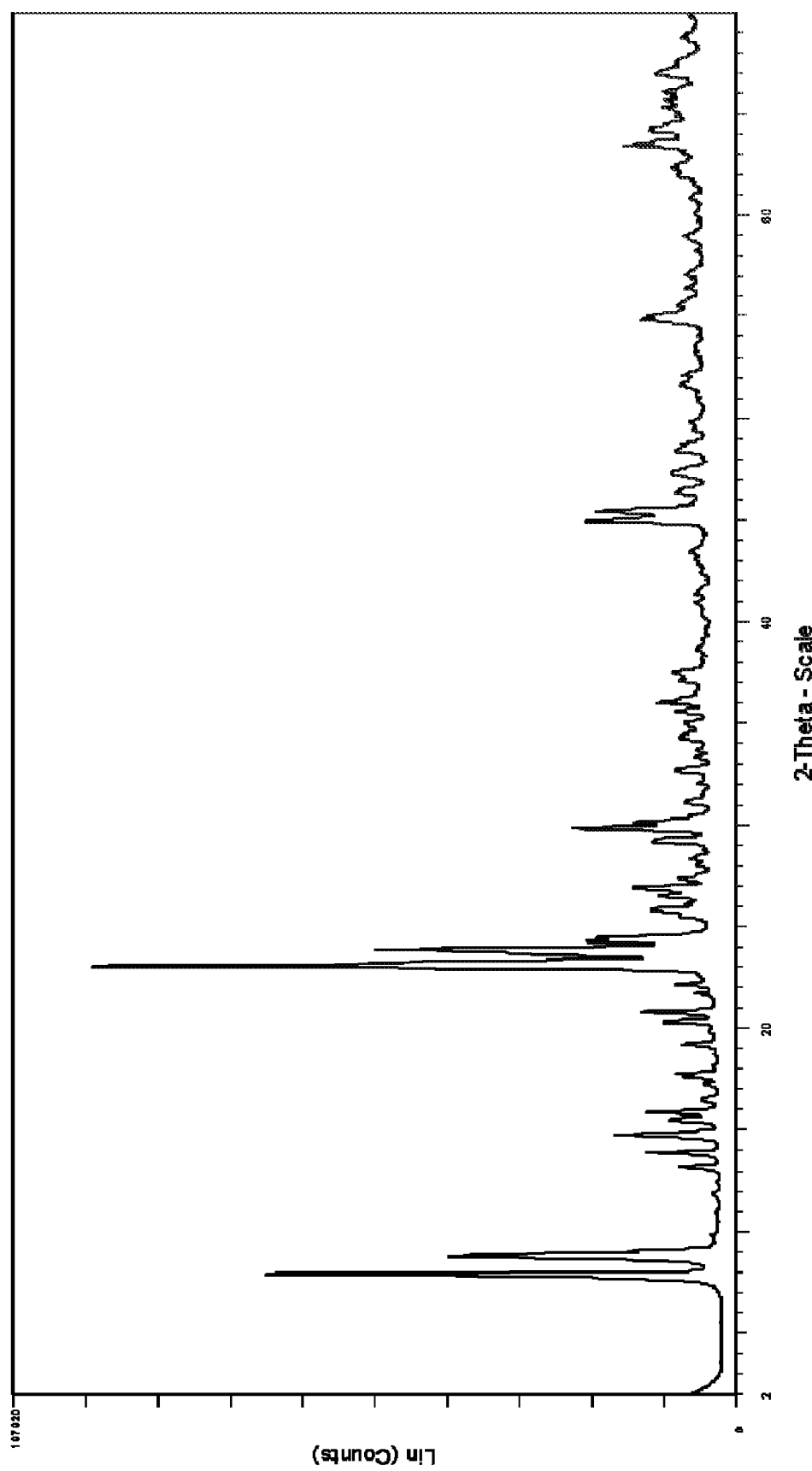

The degree of crystallization determined via XRD was 103%. The XRD of the material is shown in FIG. 5A.

The powder had a multipoint BET specific area determined via nitrogen adsorption at 77 K according to DIN 66131 of 430 m²/g. The pore volume was determined to be 0.15 cm³/g at $p/p_0$=0.256 and the median pore width to be 0.56 nm as respectively determined via Argon adsorption using the Horvath-Kawazoe method. The total intrusion volume determined according to Hg porosimetry according to DIN 66133 was 1.19 ml/g (milliliter/gram), the respective total pore area 45.8 m²/g.

The material had a water uptake of 3.3 wt. % at a relative humidity of 85%.

Figure 5B:
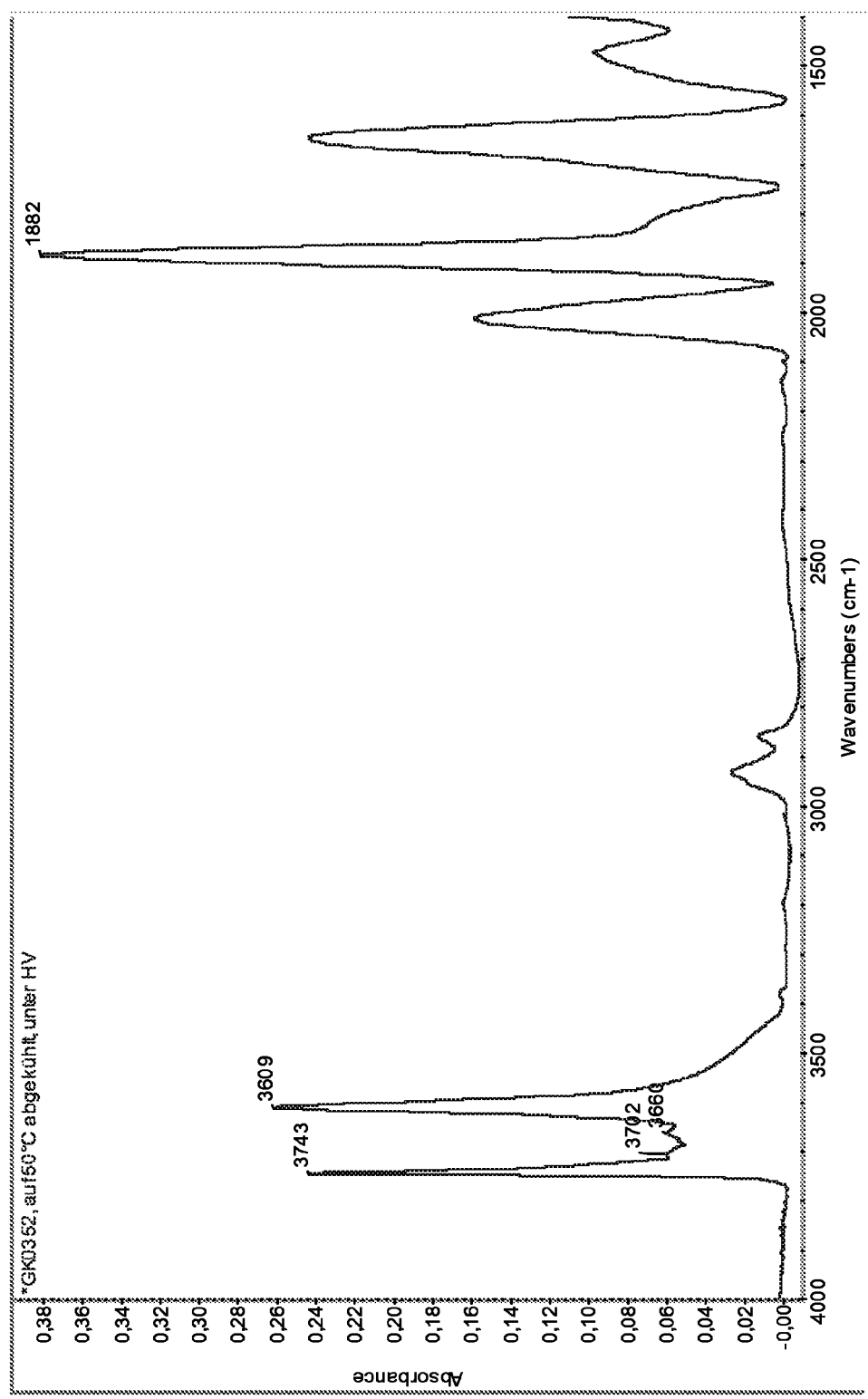

FIG. 5B shows the IR-OH bands of the sample obtained according to Reference Example 5. The band regions along with the band heights are as follows:

| Region of OH band | Assignment | Band Height |
|---|---|---|
| 3743 cm⁻¹ | external acid sites, i.e. "surface silanol" | 0.24 |
| 3702 cm⁻¹ | Lewis acid sites from extraframework Al | 0.06 |
| 3660 cm⁻¹ | Lewis acid sites from extraframework Al | 0.06 |
| 3609 cm⁻¹ | internal Broensted acid sites, i.e. "silanol nests" | 0.26 |

Accordingly, the IR-band ratio of the absorbance intensity for the silanol nests to the surface silanol amounts to 1.08.

Reference Example 6

Water-Treatment of ZSM-5 Zeolite at an $SiO_2:Al_2O_3$ Molar Ratio of 250

Starting from the calcined powder obtained according to Reference Example 2, a post-treatment stage was performed as follows:

100 g of the calcined zeolitic powder obtained according to Reference Example 2 were suspended in 2000 g of deionized water. The mixture was filled in a vessel and the vessel was closed (pressure-tight). Then, the mixture was heated to a temperature of 145° C. within 1.5 h and kept at this temperature under autogenous pressure (about 8 bar) for 8 h. The water-treated powder was subjected to filtration and washed with deionized water. The obtained filter cake was dried at 120° C. for 4 h. Subsequently, the dried material was heated under air to a temperature of 500° C. within 4 h and kept at this temperature for 5 h. The yield thereafter was 100 g.

The thus obtained water-treated zeolitic powder had a Si content of 46 wt. %, an Al content of 0.43 wt. % which correspond to an $SiO_2:Al_2O_3$ molar ratio of 206.

Figure 6A:
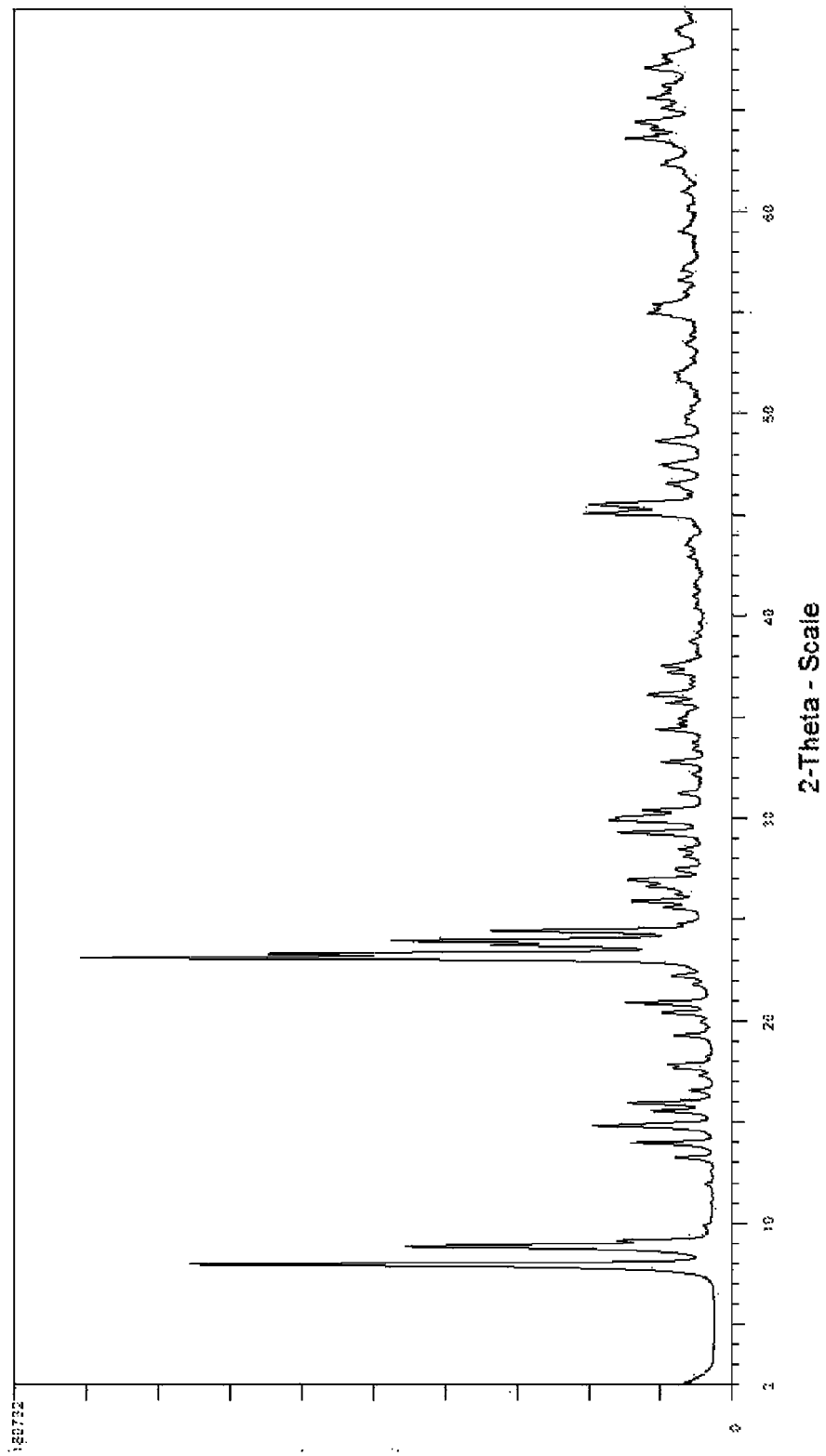
Figure 6B:
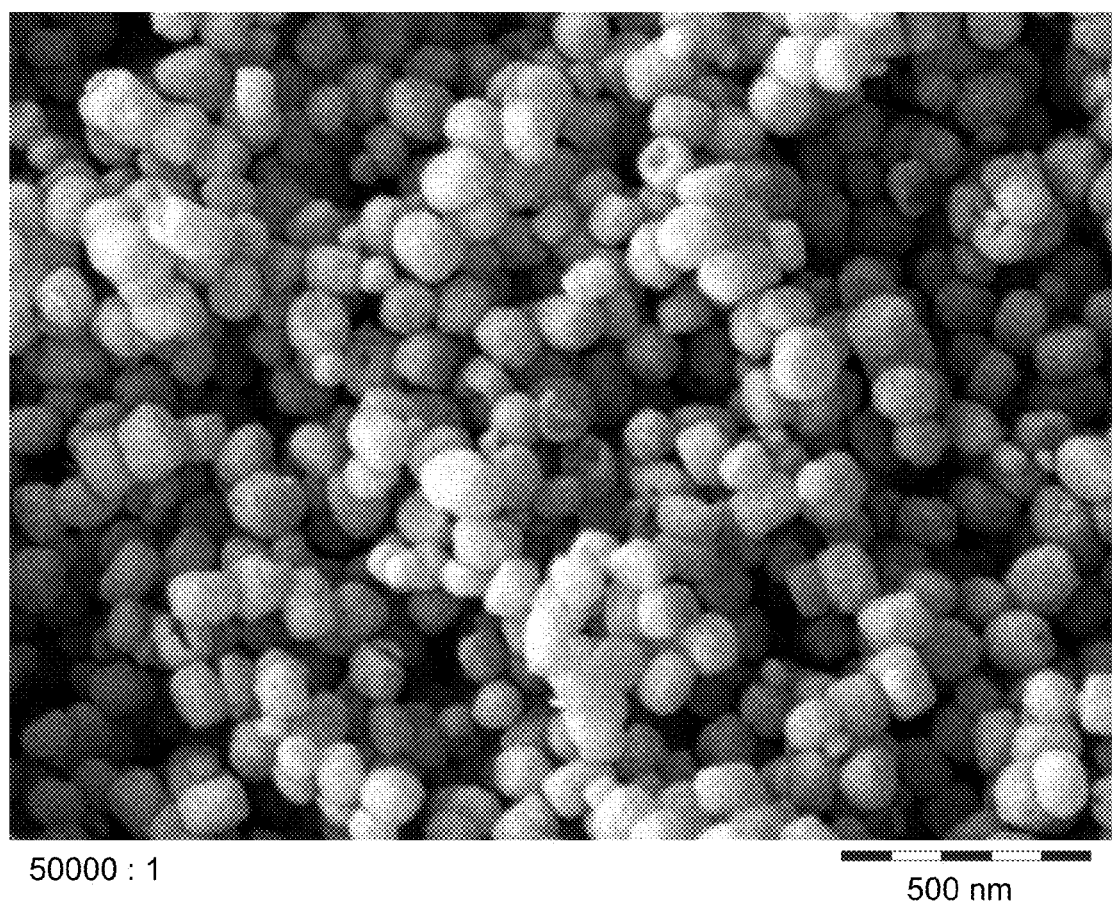

The degree of crystallization determined via XRD was 115-118%. The XRD of the material is shown in FIG. 6A. Thus, the inventive water treatment caused a considerable increase from a value of 96% (cf. Example 1) to a value of 115-118%. FIG. 6B shows the electron micrograph of the product as obtained from SEM at a magnification of 50×10⁴. As may be taken from the micrograph, practically only spherical primary particles are observed even at this high degree of magnification, wherein the size of the primary particles was determined to lie in the range of from 70-170 nm.

The powder had a multipoint BET specific area determined via nitrogen adsorption at 77 K according to DIN 66133 of 438 m²/g. The pore volume was determined to be 0.18 cm³/g at $p/p_0$=0.281 and the median pore width to be 0.54 nm as respectively determined via Argon adsorption using the Horvath-Kawazoe method. The total intrusion volume determined according to Hg porosimetry according to DIN 66133 was 1.13 ml/g (milliliter/gram), the respective total pore area 46.9 m²/g.

The total amount of adsorbed water as determined was 4.0-4.2 wt. % (compared to 7.1 wt. % of the starting material as described in Reference Example 2). Therefore, it is clearly shown that the inventive water treatment increases the hydrophobicity of the powder.

Figure 6C:
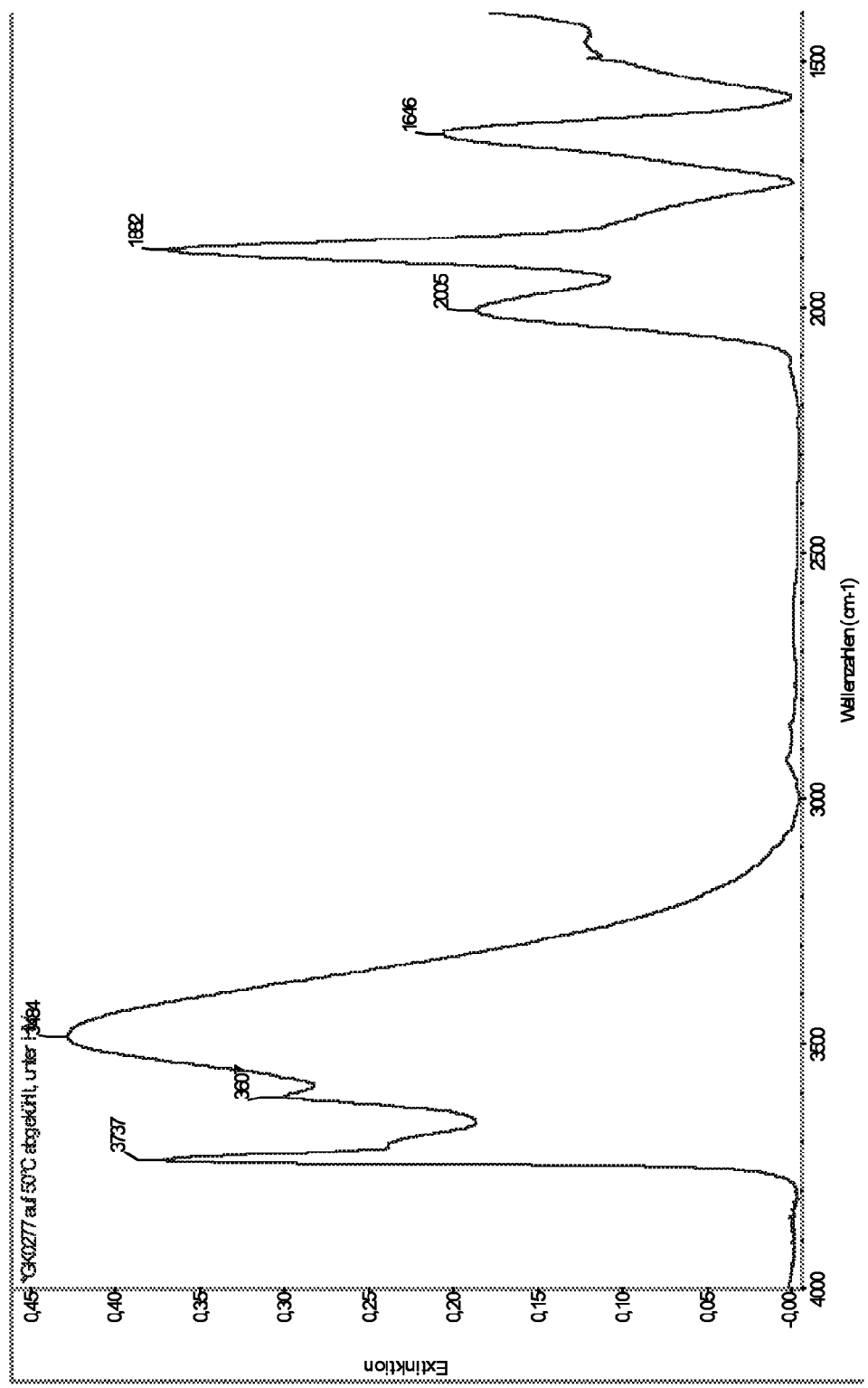

The IR spectrum of the powder according to Reference Example 6 is shown in FIG. 6C. The band regions of the powder according to Reference Example 6 along with the band heights are as follows:

| Region of OH band | Assignment | Band Height |
|---|---|---|
| 3737 cm⁻¹ | external acid sites, i.e. "surface silanol" | 0.37 |
| ~3700 cm⁻¹ | Lewis acid sites from extraframework Al | value too low to be measured |
| 3607 cm⁻¹ | Lewis acid sites from extraframework Al | 0.30 |
| 3484 cm⁻¹ | internal Broensted acid sites, i.e. "silanol nests" | 0.43 |

Accordingly, the IR-band ratio of the absorbance intensity for the silanol nests to the surface silanol amounts to 1.16.

Reference Example 7

Water-Treatment of ZSM-5 Zeolite at an $SiO_2:Al_2O_3$ Molar Ratio of 250 According to Procedure in US2007/0135637A1

Starting from the calcined powder obtained according to Reference Example 2, a post-treatment stage was performed as follows:

132 g of the calcined zeolitic powder obtained according to Reference Example 2 were suspended in 1300 g of deionized water. The mixture was filled in a vessel and the vessel was closed (pressure-tight). Then, the mixture was heated to a temperature of 175° C. and kept at this temperature under autogenous pressure (about 8.1 bar) for 24 h. The water-treated powder was subjected to filtration and washed once with 500 mL deionized water. The obtained filter cake was dried at 120° C. for 16 h. Subsequently, the dried material was heated under air to a temperature of 500° C. and kept at this temperature for 5 h. The yield thereafter was 128 g.

The thus obtained water-treated zeolitic powder had a Si content of 45 wt. %, an Al content of 0.39 wt. % which correspond to an $SiO_2:Al_2O_3$ molar ratio of 222.

Figure 7A:
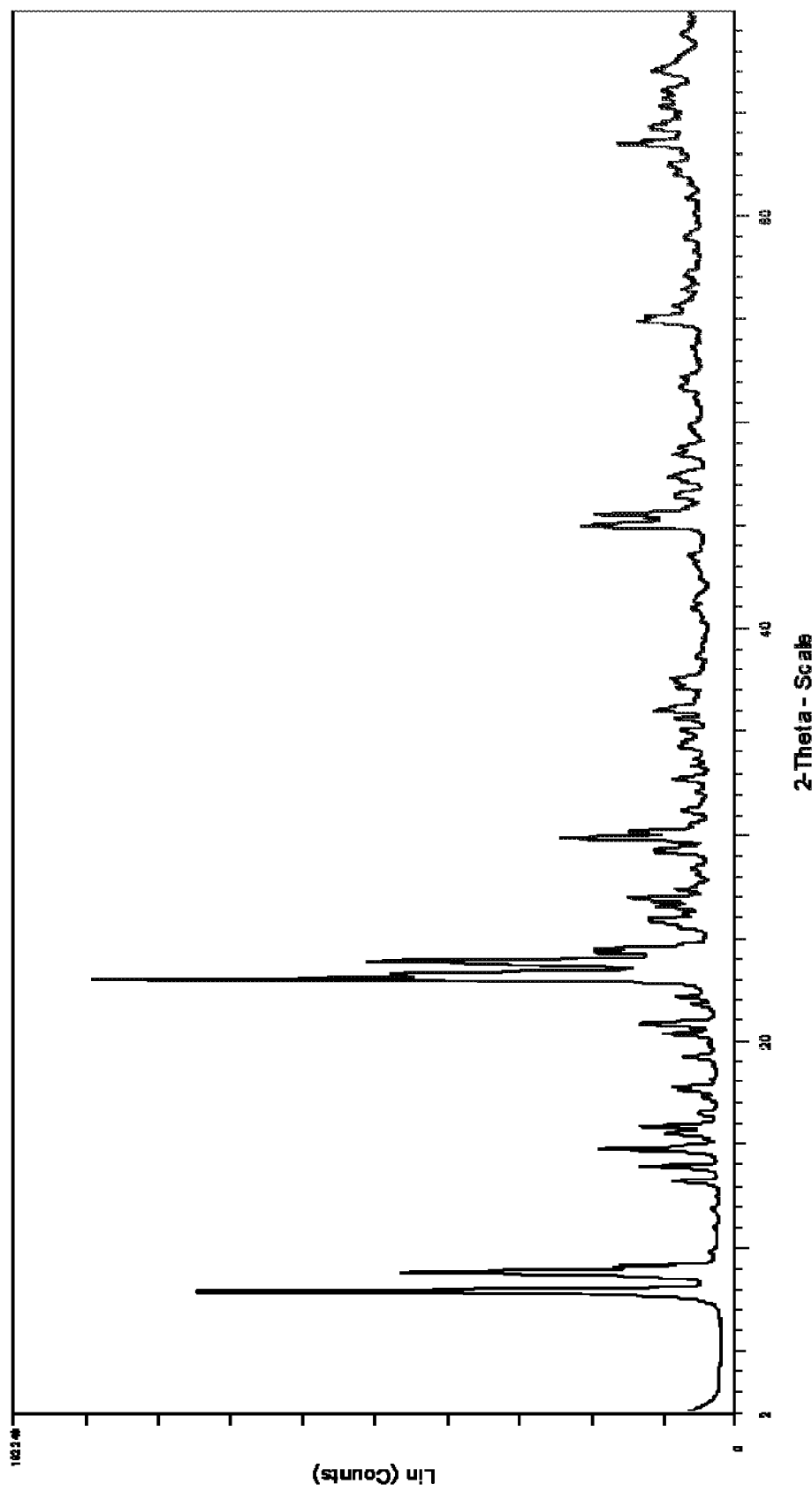

The degree of crystallization determined via XRD was 104%. The XRD of the material is shown in FIG. 7A.

The powder had a multipoint BET specific area determined via nitrogen adsorption at 77 K according to DIN 66131 of 386 m²/g. The pore volume was determined to be 0.15 cm$^3$/g at p/p$_0$=0.255 and the median pore width to be 0.57 nm as respectively determined via Argon adsorption using the Horvath-Kawazoe method.

The total intrusion volume determined according to Hg porosimetry according to DIN 66133 was 1.11 ml/g (milliliter/gram), the respective total pore area 47.6 m$^2$/g.

The material had a water uptake of 2.2 wt. % at a relative humidity of 85%.

Figure 7B:
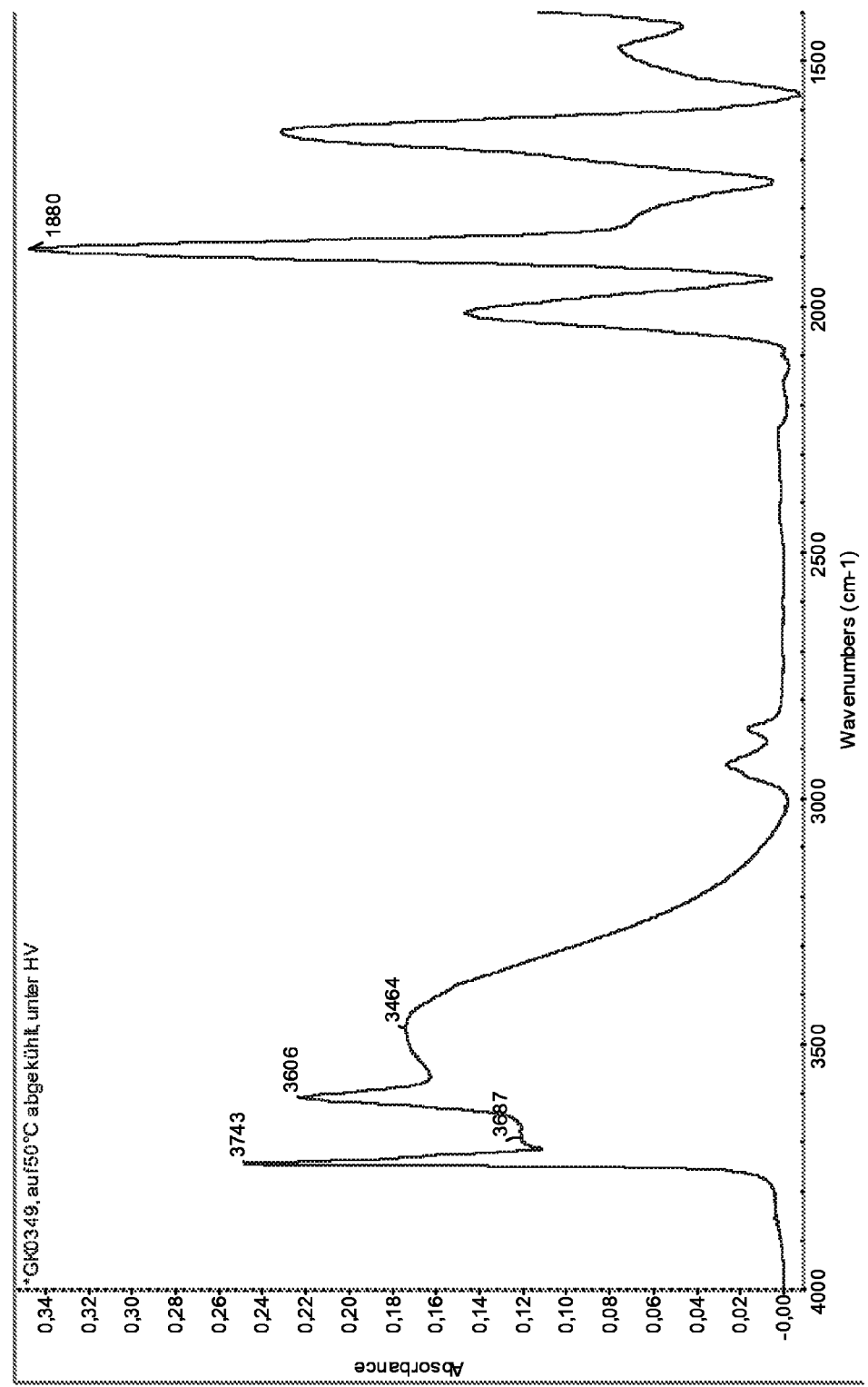

FIG. 7B shows the IR-OH bands of the sample obtained according to Reference Example 7. The band regions along with the band heights are as follows:

| Region of OH band | Assignment | Band Height |
|---|---|---|
| 3743 cm$^{-1}$ | external acid sites, i.e. "surface silanol" | 0.25 |
| 3687 cm$^{-1}$ | Lewis acid sites from extraframework Al | 0.12 |
| 3606 cm$^{-1}$ | Lewis acid sites from extraframework Al | 0.22 |
| 3464 cm$^{-1}$ | internal Broensted acid sites, i.e. "silanol nests" | 0.17 |

Accordingly, the IR-band ratio of the absorbance intensity for the silanol nests to the surface silanol amounts to 0.68.

Reference Example 8

Shaping of ZSM-5 Zeolite from Reference Example 1

ZSM-5 powder (100 g) obtained from Reference Example 1 was mixed with Pural SB (86.5 g), formic acid (2.6 g in 20 mL water) and Walocel (5 g). The masses of the raw materials were chosen in a way as to yield a zeolite-to-binder ratio of 60:40 in the resulting calcined shaped bodies. The mixture was homogenized in a kneading machine by the addition of water (100 g). The obtained plastic mixture was formed to strands (Ø2.5 mm) using a strand press (pressure ~100 bar). The strands were dried (16 h, 120° C.) and calcined (4 h, 500° C.), thus obtaining extrudates having a cutting hardness of 11.1 N.
Elemental Analysis:

| Si | 25.6 wt.-% |
|---|---|
| Al | 19.6 wt.-% |

The BET surface area of the extrudates was determined to 362 m$^2$/g, and the pore volume as obtained by Hg-Porosimetry to 0.46 cm$^3$/g, the respective total pore area 117.0 m$^2$/g.

Reference Example 9

Shaping of ZSM-5 Zeolite from Reference Example 2

ZSM-5 powder (100 g) obtained from Reference Example 2 was mixed with Pural SB (86.5 g), formic acid (2.6 g in 20 mL water) and Walocel (5 g). The masses of the raw materials were chosen in a way as to yield a zeolite-to-binder ratio of 60:40 in the resulting calcined shaped bodies. The mixture was homogenized in a kneading machine by the addition of water (83 g). The obtained plastic mixture was formed to strands (Ø2.5 mm) using a strand press (pressure ~100 bar). The strands were dried (16 h, 120° C.) and calcined (4 h, 500° C.), thus obtaining extrudates having a cutting hardness of 21.6 N.
Elemental Analysis:

| Si | 25.7 wt.-% |
|---|---|
| Al | 19.1 wt.-% |

The BET surface area of the extrudates was determined to 374 m$^2$/g, and the pore volume as obtained by Hg-Porosimetry to 0.36 cm$^3$/g, the respective total pore area 119.5 m$^2$/g.

Reference Example 10

Shaping of ZSM-5 Zeolite from Reference Example 3

ZSM-5 powder (100 g) obtained from Reference Example 3 was mixed with Pural SB (91.4 g), formic acid (2.7 g in 10 mL water) and Walocel (5 g). The masses of the raw materials were chosen in a way as to yield a zeolite-to-binder ratio of 60:40 in the resulting calcined shaped bodies. The mixture was homogenized in a kneading machine by the addition of water (90 g). The obtained plastic mixture was formed to strands (Ø2.5 mm) using a strand press (pressure ~125 bar). The strands were dried (16 h, 120° C.) and calcined (4 h, 500° C.), thus obtaining extrudates having a cutting hardness of 8.8 N.
Elemental Analysis:

| Si | 24.7 wt.-% |
|---|---|
| Al | 20.0 wt.-% |

The BET surface area of the extrudates was determined to 335 m$^2$/g, and the pore volume as obtained by Hg-Porosimetry to 0.65 cm$^3$/g.

Reference Example 11

Shaping of Water-Treated ZSM-5 Zeolite at an SiO$_2$:Al$_2$O$_3$ Ratio of 100 from Reference Example 4

Water-treated ZSM-5 powder (88.2 g) from Reference Example 4 was mixed with Pural SB (80.6 g), formic acid (2.4 g in 20 mL water) and Walocel (4.4 g). The masses of the raw materials were chosen in a way as to yield a zeolite-to-binder ratio of 60:40 in the resulting calcined shaped bodies. The mixture was homogenized in a kneading machine by the addition of water (75 g). The obtained plastic mixture was formed to strands (Ø2.5 mm) using a strand press (pressure ~130 bar). The strands were dried (16 h, 120° C.) and calcined (4 h, 500° C.). They were split to 1.6-2.0 mm fractions using a sieving machine equipped with two steel balls (Ø2 cm, 258 g/ball) prior to application in the conversion of methanol to olefins.

The obtained extrudates had a Si content of 25.3 wt. %, an Al content of 20.9 wt. % and a multipoint BET specific area determined via nitrogen adsorption at 77 K according to DIN 66133 of 362 m$^2$/g.

The crush strength of the moldings as determined according to the method using a crush strength test machine Z2.5/TS1S as described above was 6.4 N.

The total intrusion volume determined according to Hg porosimetry according to DIN 66133 was 0.69 mL/g (milliliter/gram), the respective total pore area 121.7 m$^2$/g.

Reference Example 12

Shaping of Water-Treated ZSM-5 Zeolite at an $SiO_2:Al_2O_3$ Ratio of 250 from Reference Example 6

Water-treated ZSM-5 powder (87 g) from Reference Example 6 was mixed with Pural SB (79.5 g), formic acid (2.4 g in 20 mL water) and Walocel (4.4 g). The masses of the raw materials were chosen in a way as to yield a zeolite-to-binder ratio of 60:40 in the resulting calcined shaped bodies. The mixture was homogenized in a kneading machine by the addition of water (75 g). The obtained plastic mixture was formed to strands (Ø2.5 mm) using a strand press (pressure ~100 bar). The strands were dried (16 h, 120° C.) and calcined (4 h, 500° C.). They were split to 1.6-2.0 mm fractions using a sieving machine equipped with two steel balls (Ø2 cm, 258 g/ball) prior to application in the conversion of methanol to olefins.

The obtained extrudates had a Si content of 25.1 wt. %, an Al content of 21.1 wt. % and a multipoint BET specific area determined via nitrogen adsorption at 77 K according to DIN 66133 of 362 $m^2/g$.

The crush strength of the moldings as determined according to the method using a crush strength test machine Z2.5/TS1S as described above was 8.9 N.

The total intrusion volume determined according to Hg porosimetry according to DIN 66133 was 0.52 mL/g (milliliter/gram), the respective total pore area 126.1 $m^2/g$.

Reference Example 13

Shaping of ZSM-5 Zeolite Water-Treated According to US2007/0135637A1 at an $SiO_2:Al_2O_3$ Molar Ratio of 100 from Reference Example 5

Water treated material from Reference Example 5 was shaped using the same procedure as in Reference Example 11.

Reference Example 14

Shaping of ZSM-5 Zeolite Water-Treated According to US2007/0135637A1 at an $SiO_2:Al_2O_3$ Molar Ratio of 250 from Reference Example 7

Water treated material from Reference Example 7 was shaped using the same procedure as in Reference Example 12.

Comparative Example 1

Shaping of a Commercial ZSM-5 Zeolite with an $SiO_2:Al_2O_3$ Molar Ratio of 100

For comparison to the inventive materials, the procedure of Reference Example 8 was repeated using a commercial ZSM-5 zeolite (PZ/2-100 H from ZEOCHEM®) having an $SiO_2:Al_2O_3$ molar ratio of 100. Analysis of the zeolitic material prior to conducting the procedure afforded a BET surface area of 412 $m^2/g$. The pore volume was determined to be 0.16 $cm^3/g$ at $p/p_0=0.304$ and the median pore width to be 0.55 nm as respectively determined via Argon adsorption using the Horvath-Kawazoe method. Temperature programmed desorption of ammonia ($NH_3$-TPD) afforded values of 0.41 mmol/g when conducted at 161° C. and of 0.25 mmol/g when conducted at 355° C. The size of the primary particles of the commercial ZSM-5 zeolite as determined by SEM were shown to lie in the range of from 200-500 nm.

After repeating the procedure of Reference Example 8 using the commercial ZSM-5 zeolite, the extrudates which were obtained were shown to have a cutting hardness of 26.4 N.

Elemental Analysis:

| | |
|---|---|
| Si | 25.9 wt.-% |
| Al | 19.7 wt.-% |

The BET surface area of the extrudates was determined to 310 $m^2/g$, and the pore volume as obtained by Hg-Porosimetry to 0.36 $cm^3/g$.

Example 8

Catalyst Testing in the Conversion of Methanol to Olefins

The extrudates obtained from Reference Examples 8-14, and Comparative Example 1 were respectively split to 1.6-2.0 mm fractions using a sieving machine equipped with two steel balls (Ø2 cm, 258 g/ball) for providing the respective catalyst sample. 2 g of each catalyst sample was then respectively diluted with 23 g of silicon carbide for affording the respective catalyst charge used in testing.

Methanol was evaporated, mixed with nitrogen to afford a gas stream containing 75 vol.-% methanol and 25 vol.-% nitrogen. Methanol in the gas stream was then converted to dimethylether in a heated pre-reactor (275° C.) charged with alumina split (34 mL). The resulting stream was then converted in a continuously operated, electrically heated tubular reactor that was charged with the respective zeolite catalyst (2 g, diluted with 23 g of SiC) to be tested. The MTO reaction was conducted at a temperature of 450-500° C. at a pressure (absolute) of 1-2 bar and at a weight hourly space velocity of 6 $h^{-1}$ based on the volume of methanol in the initial gas stream. The reaction was interrupted after the methanol conversion rate had fallen below 97%. The gaseous product mixture was analyzed by on-line gas chromatography, the results of which are displayed in the table below.

TABLE

Average selectivities and operation time at a methanol conversion rate of >97%.

| | Ref. Ex. 8 | Ref. Ex. 11 | Ref. Ex. 13 | Ref. Ex. 9 | Ref. Ex. 12 | Ref. Ex. 14 | Ref. Ex. 10 | Comp. Ex. 1 |
|---|---|---|---|---|---|---|---|---|
| $SiO_2:Al_2O_3$ ratio zeolite | 96 | 99 | 96 | 233 | 206 | 222 | 325 | 103 |
| water treatment zeolite | no | yes | yes | no | yes | yes | no | no |

TABLE-continued

Average selectivities and operation time at a methanol conversion rate of >97%.

| | Ref. Ex. 8 | Ref. Ex. 11 | Ref. Ex. 13 | Ref. Ex. 9 | Ref. Ex. 12 | Ref. Ex. 14 | Ref. Ex. 10 | Comp. Ex. 1 |
|---|---|---|---|---|---|---|---|---|
| water adsorp. zeolite [%] | 6.3 | 3.8-4.1 | 3.3 | 7.1 | 4.0-4.2 | 2.2 | n.a. | n.a. |
| IR band ratio of zeolite | 1.45 | 1.00 | 1.08 | 1.36 | 1.16 | 0.68 | n.a. | n.a. |
| operation time | 26.0 | 58.0 | 111 | 15.0 | 51.0 | 294 | 21 | 20.7 |
| selectivity [%]: | | | | | | | | |
| Ethylene | 9.9 | 9.4 | 8.3 | 9.6 | 8.4 | 7.9 | 7.3 | 9.4 |
| Propylene | 22.6 | 24.8 | 32.4 | 26.7 | 30.7 | 34.9 | 24.5 | 22.0 |
| Butylene | 11.9 | 13.6 | 18.7 | 17.3 | 19.9 | 23.7 | 16.9 | 12.4 |
| $C_4$-paraffins | 12.2 | 7.9 | 4.7 | 8.6 | 5.2 | 3.7 | 6.2 | 8.3 |
| $C_{5+}$ (mixture) | 13.3 | 15.8 | 19.8 | 15.1 | 18.6 | 20.0 | 29.3 | 26.9 |
| Aromatics | 21.6 | 18.3 | 10.0 | 16.2 | 12.4 | 6.7 | 11.4 | 14.5 |
| light gas | 8.4 | 10.3 | 6.2 | 6.5 | 4.8 | 3.1 | 4.4 | 6.6 |

As may be taken from the results for the inventive process employing extrudates according to Reference Example 8, the use of a sodium-free procedure for the production of the zeolitic material contained in the catalyst used in the process affords a considerably improved catalyst lifetime compared to the same process employing a catalyst according to Comparative Example 1. Said pronounced improvement is all the more surprising considering the comparable silica to alumina ratios of the zeolitic materials, as well as their comparable selectivities in the conversion of methanol to olefins, and in particular to propylene and butylene.

Furthermore, as may be taken from the results for the inventive process employing extrudates according to Reference Examples 9 and 10, upon increase of the silica to alumina ratio in the zeolitic material obtained from a sodium-free procedure, it has unexpectedly been found that a considerable increase in the selectivities for propylene and butylene may be achieved. In particular, as may be observed by comparing the results obtained according to the inventive process employing a catalyst according to Reference Example 10 with the results obtained according to Comparative Example 1, it has surprisingly been found that a clear and sustained increase in $C_3$- and $C_4$-olefin selectivities may be achieved by the inventive process, even though the lifetime of the catalyst according to Reference Example 10 in a process according to the present invention is comparable to a process employing an extrudate as obtained from Comparative Example 1.

Far more surprisingly, however, as may be taken from the results for the inventive process employing extrudates according to Reference Examples 11-14, the use of a water treatment procedure for increasing the hydrophobicity of the zeolitic materials leads to a considerable increase in the selectivities for both propylene and butylene, wherein the higher the hydrophobicity of the water-treated materials, i.e. the lower the water adsorption of the zeolitic material, the greater the increase in both $C_3$- and $C_4$-olefin selectivities which may be observed. Furthermore, a tremendous increase in the lifetime of the catalyst is observed when applying catalysts with a higher hydrophobicity wherein again the higher the hydrophobicity of the water-treated materials, the greater the increase in catalyst lifetime which is observed in the inventive process.

The invention claimed is:

1. A process for the conversion of oxygenates to olefins comprising
(i) providing a gas stream comprising one or more oxygenates; and
(ii) contacting the gas stream with a catalyst at conditions effective to convert the oxygenates to olefins; wherein the catalyst comprises a zeolitic material having an MFI, MEL, and/or MWW framework structure comprising $YO_2$ and $X_2O_3$, wherein Y is a tetravalent element, and X is a trivalent element, said zeolitic material prepared by a process comprising
(1) preparing a mixture comprising one or more sources for $YO_2$, one or more sources for $X_2O_3$, and one or more solvents;
(2) heating the mixture obtained in step (1) to obtain a product mixture including the zeolitic material, wherein the zeolitic material contains 3 wt.-% or less of one or more elements M, based on 100 wt.-% of $YO_2$, wherein M in as alkali or alkaline earth element;
isolating the zeolitic material from the product mixture obtained in (2); and
subjecting the zeolitic material to a hydrothermal treatment under autogenous pressure; wherein the provided gas stream of step (i) includes from 30 to 70 vol. % of oxygenates, and from 30 to 60 vol. % water, based on the total volume the gas stream.

2. The process of claim 1, wherein the zeolitic material obtained in step (2) contains 1 wt.-% or less of the one or more elements M.

3. The process of claim 1, wherein the gas stream provided in step (i) contains one or more oxygenates selected from the group consisting of aliphatic alcohols, ethers, carbonyl compounds, and mixtures of two or more thereof.

4. The process of claim 1, wherein the gas stream provided in step (i) contains from 30 to 100 vol.-% of oxygenates based on the total volume of the gas stream.

5. The process of claim 1, wherein the gas stream provided in step (i) contains 60 vol.-% or less of water based on the total volume of the gas stream.

6. The process of claim 1, wherein contacting of the gas stream with the catalyst in step (ii) is performed at a temperature in the range of 200 to 700° C., and a pressure in the range of 0.1 to 10 bar.

7. The process of claim 1, wherein the process is at least in part performed in a continuous mode, and the weight hourly space velocity (WHSV) of the gas stream in step (ii) ranges from 0.5 to 50 $h^{-1}$.

8. The process of claim 1, wherein at least 95% by weight of the zeolitic material has a diameter of less than or equal to 1 μm.

9. The process of claim 1, wherein at least 90% of the zeolitic material is spherical, and at least 95% by weight of the zeolitic material has a diameter of from 5 to 800 nm.

10. The process of claim 1, wherein the zeolitic material includes a $YO_2:X_2O_3$ atomic ratio of from 10 to 1,500.

11. The process of claim 1, wherein the tetravalent element V is selected from the group consisting of Si, Sn, Ti, Zr, Ge, and any one mixture thereof.

12. The process of claim 1, wherein the trivalent element X is selected from the group consisting of Al, B, In, Ga, and any one mixture thereof.

13. The process of claim 1, wherein the zeolitic material comprises ZSM-5.

14. The process of claim 1, wherein the BET surface area of the zeolitic material determined according to DIN 66131 ranges from 200 to 900 m$^2$/g.

15. The process of claim 1, wherein the $YO_2: X_2O_3$ molar ratio of the mixture prepared in step (1) ranges from 10 to 1,500.

16. The process of claim 1, wherein the one or more solvents provided in step (1) comprise one or more polar solvents.

17. The process of claim 1, wherein the mixture in step (1) further comprises one or more organotemplates.

18. The process of claim 17, wherein the one or more organotemplates comprises one or more tetraalkylammonium compounds selected from the group consisting of tetraethylammonium compounds, triethylpropylammonium compounds, diethyldipropylammonium compounds, ethyltripropylammonium compounds, tetrapropylammonium compounds, and mixtures of two or more thereof.

19. The process of claim 17, wherein the one or more organotemplates comprises one or more alkenyltrialkylammonium compounds selected from the group consisting of N—($C_2$-$C_5$)alkenyl-tri-($C_1$-$C_5$)alkylammonium compounds.

20. The process of claim 17, wherein the molar ratio of the total amount of the one or more organotemplates of the mixture obtained in step (1) to $YO_2$ ranges from 1:(0.1-30).

21. The process of claim 1, wherein the mixture according to step (1) further comprises one or more sources for OH$^-$.

22. The process of claim 21, wherein the OH$^-$:$YO_2$ molar ratio of the mixture obtained in step (1) ranges from 0.01 to 5.

23. The process of claim 1, wherein the crystallization in step (2) is conducted under solvothermal conditions.

24. The process of claim 1, wherein the heating the mixture is for at least 3 h.

25. The process of claim 1, Wherein after step (2) the process further comprises
adjusting the pH of the product mixture obtained in (2) to a pH in the range of 5 to 9; and/or
washing the zeolitic material; and/or
calcining the zeolitic material.

26. The process of claim 25, wherein the calcining of the zeolitic material is conducted at a temperature in the range of 300 to 850° C.

27. The process of claim 1, wherein the hydrothermal treatment is conducted in water.

28. The process of claim 1, wherein the hydrothermal treatment is conducted under heating at a temperature range of from 80 to 250° C.

29. The process of claim 1, wherein the hydrothermal treatment is conducted for a duration ranging from 2 to 72 h.

30. The process of claim 1, wherein the hydrothermally treated zeolitic material comprises a water uptake of 10.0 wt.-% or less, at 85% humidity and 25° C.

31. A process for the conversion of oxygenates to olefins, the process comprising
(i) providing a gas stream comprising one or more oxygenates; and
(ii) contacting the gas stream with a catalyst at conditions effective to convert the oxygenates to olefins at a temperature in a range from 200 to 700° C., and at a pressure in a range of 0.1 to 10 bar, the catalyst comprising a zeolitic material comprising $SiO_2$ and $Al_2O_3$ with an atomic ratio of 90 to 300, respectively
said zeolitic material prepared by a process comprising:
preparing a mixture comprising one or more sources for $SiO_2$, one or more sources for $Al_2O_3$, and one or more polar solvents;
heating the mixture obtained in step (1) to obtain a product mixture including the zeolitic material having an MFI, MEL and/or MWW framework structure, and 1 wt.-% or less of sodium, based on 100 wt.-% of $SiO_2$;
isolating the zeolitic material from the product mixture; and
subjecting the zeolitic material to a hydrothermal treatment at a temperature range from 120 to 200° C., the hydrothermal treated zeolitic material having a water uptake of 4.5 wt,-% or less at 85% humidity and 25° C.

32. The process of claim 31, wherein the process of producing the zeolitic material further comprises calcining the zeolitic material after isolating the zeolitic material, the calcining conducted at a temperature in the range of 300 to 850° C.

33. The process of claim 1, wherein M includes sodium and potassium.

34. The process of claim 1, wherein M is sodium.

35. The process of claim 1, wherein the catalyst exhibits an operational lifetime that 4.2× to 19.6× greater than a similar catalyst that is not hydrothermally treated in the oxygenate to olefin process.

* * * * *